United States Patent
Karnik et al.

(10) Patent No.: US 9,381,477 B2
(45) Date of Patent: Jul. 5, 2016

(54) MICROFLUIDIC SYNTHESIS OF ORGANIC NANOPARTICLES

(75) Inventors: Rohit Karnik, Cambridge, MA (US); Frank X. Gu, Waterloo (CA); Pamela Basto, Somerville, MA (US); Chris Cannizzaro, Washington, DC (US); Alireza Khademhosseini, Cambridge, MA (US); Robert S. Langer, Newton, MA (US); Omid C. Farokhzad, Chestnut Hill, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 1320 days.

(21) Appl. No.: 12/306,249

(22) PCT Filed: Jun. 22, 2007

(86) PCT No.: PCT/US2007/071901
§ 371 (c)(1),
(2), (4) Date: Sep. 14, 2009

(87) PCT Pub. No.: WO2007/150030
PCT Pub. Date: Dec. 27, 2007

(65) Prior Publication Data
US 2010/0022680 A1 Jan. 28, 2010

Related U.S. Application Data

(60) Provisional application No. 60/805,656, filed on Jun. 23, 2006, provisional application No. 60/916,998, filed on May 9, 2007.

(51) Int. Cl.
*B01L 3/00* (2006.01)
*G01N 1/10* (2006.01)
(Continued)

(52) U.S. Cl.
CPC .......... *B01F 3/0807* (2013.01); *A61K 9/5153* (2013.01); *A61K 9/5192* (2013.01);
(Continued)

(58) Field of Classification Search
CPC .............. B01J 19/0093; B01J 2219/00164; B01J 2219/00317; B01J 2219/00418; B01J 2219/00585; B01J 2219/0059; B01J 2219/00889; B01F 13/0059; B01F 5/0646; B01F 5/0647; B01L 2300/0819; B01L 2300/0829; B01L 3/0293; B01L 3/5025; B01L 3/5027
USPC .................................. 422/500–504; 436/180
See application file for complete search history.

(56) References Cited

U.S. PATENT DOCUMENTS 3,766,774 A 10/1973 Clark
4,270,537 A 6/1981 Romaine
(Continued)

FOREIGN PATENT DOCUMENTS

CA 2453959 1/2003
CA 2649149 10/2007
(Continued)

OTHER PUBLICATIONS

U.S. Appl. No. 12/239,136, filed Sep. 26, 2008, Farokhzad, et al.
(Continued)

*Primary Examiner* — Dean Kwak
(74) *Attorney, Agent, or Firm* — Pabst Patent Group LLP

(57) ABSTRACT

The present invention provides microfluidic systems and methods for the production of particles (e.g., nanoparticles) for drug delivery. The present invention provides microfluidic devices useful for production of particles by nanoprecipitation. The present invention provides highly homogenous compositions of particles produced by inventive microfluidic devices.

21 Claims, 9 Drawing Sheets

(51) Int. Cl.
*B01F 3/08* (2006.01)
*A61K 9/51* (2006.01)
*A61K 47/48* (2006.01)
*B01F 5/04* (2006.01)
*B01F 5/06* (2006.01)
*B01F 11/00* (2006.01)
*B01F 13/00* (2006.01)
*B01J 13/04* (2006.01)
*B01J 19/00* (2006.01)
*B82Y 30/00* (2011.01)
*A61K 9/16* (2006.01)

(52) U.S. Cl.
CPC ..... *A61K47/48907* (2013.01); *A61K 47/48915* (2013.01); *B01F 5/0471* (2013.01); *B01F 5/061* (2013.01); *B01F 5/0646* (2013.01); *B01F 5/0647* (2013.01); *B01F 11/0071* (2013.01); *B01F 13/0059* (2013.01); *B01F 13/0062* (2013.01); *B01J 13/04* (2013.01); *B01J 19/0046* (2013.01); *B01J 19/0093* (2013.01); *B82Y 30/00* (2013.01); *A61K 9/1694* (2013.01); *B01F 2005/0621* (2013.01); *B01F 2005/0636* (2013.01); *B01J 2219/005* (2013.01); *B01J 2219/0059* (2013.01); *B01J 2219/0095* (2013.01); *B01J 2219/00162* (2013.01); *B01J 2219/00164* (2013.01); *B01J 2219/00459* (2013.01); *B01J 2219/00722* (2013.01); *B01J 2219/00725* (2013.01); *B01J 2219/00736* (2013.01); *B01J 2219/00822* (2013.01); *B01J 2219/00828* (2013.01); *B01J 2219/00831* (2013.01); *B01J 2219/00833* (2013.01); *B01J 2219/00889* (2013.01)

(56) References Cited

U.S. PATENT DOCUMENTS

| | | |
|---|---|---|
| 4,446,122 A | 5/1984 | Chu et al. |
| 4,596,556 A | 6/1986 | Morrow et al. |
| 4,631,211 A | 12/1986 | Houghten |
| 4,638,045 A | 1/1987 | Kohn et al. |
| 4,790,824 A | 12/1988 | Morrow et al. |
| 4,795,436 A | 1/1989 | Robinson |
| 4,806,621 A | 2/1989 | Kohn et al. |
| 4,818,542 A | 4/1989 | DeLuca |
| 4,839,416 A | 6/1989 | Orenstein |
| 4,862,851 A | 9/1989 | Washino et al. |
| 4,886,499 A | 12/1989 | Cirelli et al. |
| 4,902,615 A | 2/1990 | Freeman et al. |
| 4,904,479 A | 2/1990 | Illum |
| 4,940,460 A | 7/1990 | Casey et al. |
| 4,941,880 A | 7/1990 | Burns |
| 4,946,929 A | 8/1990 | D'Amore et al. |
| 4,959,219 A | 9/1990 | Chow |
| RE33,405 E | 10/1990 | Chu et al. |
| 4,970,299 A | 11/1990 | Bazinet et al. |
| 4,976,968 A | 12/1990 | Steiner |
| 5,010,167 A | 4/1991 | Ron et al. |
| 5,015,235 A | 5/1991 | Crossman |
| 5,019,379 A | 5/1991 | Domb et al. |
| 5,055,404 A | 10/1991 | Ueda et al. |
| 5,064,413 A | 11/1991 | McKinnon et al. |
| 5,069,936 A | 12/1991 | Yen |
| 5,093,246 A | 3/1992 | Cech et al. |
| 5,118,528 A | 6/1992 | Fessi et al. |
| 5,141,496 A | 8/1992 | Dalto et al. |
| 5,162,504 A | 11/1992 | Horoszewicz |
| 5,174,930 A | 12/1992 | Stainmesse |
| 5,175,296 A | 12/1992 | Gerster |
| 5,190,521 A | 3/1993 | Hubbard et al. |
| 5,200,181 A | 4/1993 | Soltys |
| 5,240,963 A | 8/1993 | Domb |
| 5,270,163 A | 12/1993 | Gold et al. |
| 5,312,335 A | 5/1994 | McKinnon et al. |
| 5,328,483 A | 7/1994 | Jacoby |
| 5,334,144 A | 8/1994 | Alchas et al. |
| 5,334,497 A | 8/1994 | Inaba et al. |
| 5,339,163 A | 8/1994 | Homma et al. |
| 5,342,781 A | 8/1994 | Su |
| 5,383,851 A | 1/1995 | McKinnon, Jr. et al. |
| 5,389,640 A | 2/1995 | Gerster |
| 5,399,665 A | 3/1995 | Barrera et al. |
| 5,403,750 A | 4/1995 | Braatz |
| 5,417,662 A | 5/1995 | Hjertman et al. |
| 5,449,513 A | 9/1995 | Yokoyama |
| 5,466,220 A | 11/1995 | Brenneman |
| 5,472,704 A | 12/1995 | Santus et al. |
| 5,480,381 A | 1/1996 | Weston |
| 5,500,161 A | 3/1996 | Andrianov et al. |
| 5,503,627 A | 4/1996 | McKinnon et al. |
| 5,512,600 A | 4/1996 | Mikos et al. |
| 5,514,378 A | 5/1996 | Mikos et al. |
| 5,520,639 A | 5/1996 | Peterson et al. |
| 5,527,288 A | 6/1996 | Gross et al. |
| 5,543,158 A | 8/1996 | Gref et al. |
| 5,567,588 A | 10/1996 | Gold et al. |
| 5,569,189 A | 10/1996 | Parsons |
| 5,578,325 A | 11/1996 | Domb et al. |
| 5,595,877 A | 1/1997 | Gold et al. |
| 5,599,302 A | 2/1997 | Lilley et al. |
| 5,622,699 A | 4/1997 | Ruoslahti |
| 5,649,912 A | 7/1997 | Peterson |
| 5,660,985 A | 8/1997 | Pieken et al. |
| 5,686,113 A | 11/1997 | Speaker |
| 5,696,175 A | 12/1997 | Mikos et al. |
| 5,696,249 A | 12/1997 | Gold et al. |
| 5,704,911 A | 1/1998 | Parsons |
| 5,716,404 A | 2/1998 | Vacanti et al. |
| 5,733,925 A | 3/1998 | Kunz et al. |
| 5,736,372 A | 4/1998 | Vacanti et al. |
| 5,744,155 A | 4/1998 | Friedman |
| 5,763,177 A | 6/1998 | Gold et al. |
| 5,766,635 A | 6/1998 | Spenleuhauer |
| 5,770,417 A | 6/1998 | Vacanti et al. |
| 5,786,204 A | 7/1998 | He et al. |
| 5,789,163 A | 8/1998 | Drolet et al. |
| 5,804,178 A | 9/1998 | Vacanti et al. |
| 5,817,785 A | 10/1998 | Gold et al. |
| 5,820,879 A | 10/1998 | Fernandez et al. |
| 5,837,752 A | 11/1998 | Shastri et al. |
| 5,843,653 A | 12/1998 | Gold et al. |
| 5,843,732 A | 12/1998 | Davis et al. |
| 5,853,984 A | 12/1998 | Davis et al. |
| 5,869,103 A | 2/1999 | Yah et al. |
| 5,871,747 A | 2/1999 | GengouxSedlik |
| 5,874,218 A | 2/1999 | Drolet et al. |
| 5,876,727 A | 3/1999 | Swain |
| 5,879,712 A | 3/1999 | Bomberger |
| 5,893,397 A | 4/1999 | Peterson et al. |
| 5,898,031 A | 4/1999 | Crooke |
| 5,902,599 A | 5/1999 | Anseth et al. |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken et al. |
| 5,977,089 A | 11/1999 | Arimilli et al. |
| 5,993,412 A | 11/1999 | Deily et al. |
| 6,001,577 A | 12/1999 | Gold et al. |
| 6,005,087 A | 12/1999 | Cook et al. |
| 6,007,845 A | 12/1999 | Domb et al. |
| 6,030,613 A | 2/2000 | Blumberg |
| 6,031,086 A | 2/2000 | Switzer |
| 6,039,969 A | 3/2000 | Tomai |
| 6,043,224 A | 3/2000 | Lee |
| 6,060,306 A | 5/2000 | Flatt |
| 6,083,505 A | 7/2000 | Miller |
| 6,095,148 A | 8/2000 | Shastri et al. |
| 6,107,094 A | 8/2000 | Crooke |
| 6,110,462 A | 8/2000 | Barbas et al. |
| 6,120,666 A * | 9/2000 | Jacobson et al. ............... 204/452 |
| 6,123,727 A | 9/2000 | Vacanti et al. |

(56) References Cited

U.S. PATENT DOCUMENTS

| | | | |
|---|---|---|---|
| 6,127,533 | A | 10/2000 | Cook et al. |
| 6,139,870 | A | 10/2000 | Verrecchia |
| 6,184,364 | B1 | 2/2001 | Pieken et al. |
| 6,190,913 | B1 | 2/2001 | Singh |
| 6,197,346 | B1 | 3/2001 | Mathiowitz |
| 6,225,460 | B1 | 5/2001 | Bischofberger et al. |
| 6,232,082 | B1 | 5/2001 | Ennifar |
| 6,235,313 | B1 | 5/2001 | Mathiowitz |
| 6,238,705 | B1 | 5/2001 | Liu et al. |
| 6,242,246 | B1 | 6/2001 | Gold et al. |
| 6,245,776 | B1 | 6/2001 | Skwierczynski |
| 6,254,890 | B1 | 7/2001 | Hirosue et al. |
| 6,265,608 | B1 | 7/2001 | Sumner, Jr. |
| 6,288,040 | B1 | 9/2001 | Muller |
| 6,291,673 | B1 | 9/2001 | Fuchs |
| 6,344,318 | B1 | 2/2002 | Gold et al. |
| 6,348,462 | B1 | 2/2002 | Gerster |
| 6,365,187 | B2 | 4/2002 | Mathiowitz et al. |
| 6,376,190 | B1 | 4/2002 | Gold et al. |
| 6,395,718 | B1 | 5/2002 | Slusher |
| 6,399,754 | B1 | 6/2002 | Cook |
| 6,403,779 | B1 | 6/2002 | Kawasaki et al. |
| 6,429,200 | B1 | 8/2002 | Monahan et al. |
| 6,444,782 | B1 | 9/2002 | Hamlin |
| 6,451,527 | B1 | 9/2002 | Larocca et al. |
| 6,458,539 | B1 | 10/2002 | Gold et al. |
| 6,458,543 | B1 | 10/2002 | Gold et al. |
| 6,482,594 | B2 | 11/2002 | Gold et al. |
| 6,492,554 | B2 | 12/2002 | Dalton et al. |
| 6,506,559 | B1 | 1/2003 | Fire et al. |
| 6,506,577 | B1 | 1/2003 | Deming et al. |
| 6,528,499 | B1 | 3/2003 | Kozikowski |
| 6,558,951 | B1 | 5/2003 | Tomai |
| 6,569,896 | B2 | 5/2003 | Dalton et al. |
| 6,589,562 | B1 | 7/2003 | Shefer et al. |
| 6,589,563 | B2 | 7/2003 | Prokop |
| 6,608,201 | B2 | 8/2003 | Gerster |
| 6,610,319 | B2 | 8/2003 | Tomai |
| 6,610,713 | B2 | 8/2003 | Tracey |
| 6,632,922 | B1 | 10/2003 | Deming et al. |
| 6,656,469 | B1 | 12/2003 | Svensson |
| 6,686,446 | B2 | 2/2004 | Deming et al. |
| 6,686,472 | B2 | 2/2004 | Gerster |
| 6,696,076 | B2 | 2/2004 | Tomai |
| 6,699,474 | B1 | 3/2004 | Cerny |
| 6,716,583 | B2 | 4/2004 | Gold et al. |
| 6,723,429 | B2 | 4/2004 | Bengs |
| 6,737,056 | B1 | 5/2004 | Presta |
| 6,747,156 | B2 | 6/2004 | Johansson |
| 6,767,702 | B2 | 7/2004 | Mirkin |
| 6,818,732 | B2 | 11/2004 | Deming et al. |
| 6,838,484 | B2 | 1/2005 | Steiner et al. |
| 6,875,605 | B1 | 4/2005 | Ma |
| 6,875,886 | B2 | 4/2005 | Frangioni |
| 6,902,743 | B1 | 6/2005 | Setterstrom |
| 6,932,971 | B2 | 8/2005 | Bachmann et al. |
| 6,984,393 | B2 | 1/2006 | Amsden |
| 6,995,284 | B2 | 2/2006 | Dalton et al. |
| 6,998,500 | B2 | 2/2006 | Dalton et al. |
| 7,008,411 | B1 | 3/2006 | Mandrusov et al. |
| 7,022,870 | B2 | 4/2006 | Dalton et al. |
| 7,026,500 | B2 | 4/2006 | Dalton et al. |
| 7,029,859 | B2 | 4/2006 | Thompson |
| 7,030,228 | B1 | 4/2006 | Schmitz |
| 7,056,704 | B2 | 6/2006 | Tuschl et al. |
| 7,078,196 | B2 | 7/2006 | Tuschl et al. |
| 7,097,837 | B2 | 8/2006 | Nielsen |
| 7,149,574 | B2 | 12/2006 | Yun |
| 7,163,680 | B2 | 1/2007 | Bander |
| 7,247,502 | B2 | 7/2007 | Ennifar |
| 7,250,499 | B2 | 7/2007 | Mirkin |
| 7,335,744 | B2 | 2/2008 | Liu |
| 7,363,076 | B2 | 4/2008 | Yun |
| 7,375,180 | B2 | 5/2008 | Gorden |
| 7,387,271 | B2 | 6/2008 | Noelle |
| 7,422,902 | B1 | 9/2008 | Wheeler |
| 7,427,629 | B2 | 9/2008 | Kedl |
| 7,488,792 | B2 | 2/2009 | Ruoslahti |
| 7,550,441 | B2 | 6/2009 | Farokhzad et al. |
| 7,727,969 | B2 | 6/2010 | Farokhzad et al. |
| 7,731,906 | B2 * | 6/2010 | Handique ......... B01L 3/502707 422/537 |
| 7,762,803 | B2 | 7/2010 | Nakazato |
| 7,767,803 | B2 | 8/2010 | Diener |
| 8,277,812 | B2 | 10/2012 | Iannacone |
| 8,323,698 | B2 | 12/2012 | Gu |
| 8,343,497 | B2 | 1/2013 | Shi |
| 8,343,498 | B2 | 1/2013 | Alexis |
| 8,562,998 | B2 | 10/2013 | Shi |
| 8,574,564 | B2 | 11/2013 | Renner |
| 8,637,028 | B2 | 1/2014 | Alexis |
| 2001/0012890 | A1 | 8/2001 | Thompson |
| 2002/0009466 | A1 | 1/2002 | Brayden |
| 2002/0064780 | A1 | 5/2002 | Gold et al. |
| 2002/0068091 | A1 | 6/2002 | Davis et al. |
| 2002/0086356 | A1 | 7/2002 | Tuschl et al. |
| 2002/0099036 | A1 | 7/2002 | Dalton et al. |
| 2002/0099096 | A1 | 7/2002 | Dalton et al. |
| 2002/0102613 | A1 | 8/2002 | Hogenboom |
| 2002/0106647 | A1 | 8/2002 | Segal |
| 2002/0116054 | A1 | 8/2002 | Lundell |
| 2002/0119473 | A1 | 8/2002 | Lupold |
| 2002/0119916 | A1 | 8/2002 | Hassan |
| 2002/0150578 | A1 | 10/2002 | He et al. |
| 2002/0151004 | A1 | 10/2002 | Craig |
| 2002/0153251 | A1 | 10/2002 | Sassi et al. |
| 2002/0156125 | A1 | 10/2002 | Broder et al. |
| 2002/0173495 | A1 | 11/2002 | Dalton et al. |
| 2003/0003103 | A1 | 1/2003 | Thompson |
| 2003/0003114 | A1 | 1/2003 | Pan |
| 2003/0009029 | A1 | 1/2003 | Buchholz et al. |
| 2003/0022868 | A1 | 1/2003 | Dalton et al. |
| 2003/0035804 | A1 | 2/2003 | D'Amico et al. |
| 2003/0054360 | A1 | 3/2003 | Gold et al. |
| 2003/0087301 | A1 | 5/2003 | Smith et al. |
| 2003/0099668 | A1 | 5/2003 | Bachmann |
| 2003/0108611 | A1 | 6/2003 | Bosch et al. |
| 2003/0108923 | A1 | 6/2003 | Tuschl et al. |
| 2003/0133988 | A1 | 7/2003 | Fearon |
| 2003/0134810 | A1 | 7/2003 | Springate et al. |
| 2003/0138557 | A1 | 7/2003 | Allison |
| 2003/0143184 | A1 | 7/2003 | Seo |
| 2003/0162761 | A1 | 8/2003 | Steiner et al. |
| 2003/0165478 | A1 | 9/2003 | Sokoll |
| 2003/0175950 | A1 | 9/2003 | McSwiggen |
| 2003/0219766 | A1 | 11/2003 | Raitano et al. |
| 2003/0225040 | A1 | 12/2003 | Dalton et al. |
| 2003/0228603 | A1 | 12/2003 | Cload |
| 2003/0232013 | A1 | 12/2003 | Sieckman et al. |
| 2003/0232792 | A1 | 12/2003 | Dalton et al. |
| 2003/0235619 | A1 | 12/2003 | Allen |
| 2004/0014789 | A1 | 1/2004 | Lau |
| 2004/0014975 | A1 | 1/2004 | Dalton et al. |
| 2004/0022727 | A1 | 2/2004 | Stanton |
| 2004/0022840 | A1 | 2/2004 | Nagy et al. |
| 2004/0029913 | A1 | 2/2004 | Dalton et al. |
| 2004/0043923 | A1 | 3/2004 | Parma et al. |
| 2004/0052727 | A1 | 3/2004 | Dalton et al. |
| 2004/0054190 | A1 | 3/2004 | Pomper |
| 2004/0059094 | A1 | 3/2004 | Bachmann et al. |
| 2004/0067196 | A1 | 4/2004 | Brunke et al. |
| 2004/0067503 | A1 | 4/2004 | Tan et al. |
| 2004/0067979 | A1 | 4/2004 | Dalton et al. |
| 2004/0072234 | A1 | 4/2004 | Parma et al. |
| 2004/0086544 | A1 | 5/2004 | Bezemer |
| 2004/0087810 | A1 | 5/2004 | Dalton et al. |
| 2004/0092470 | A1 | 5/2004 | Leonard et al. |
| 2004/0136961 | A1 | 7/2004 | Prokop et al. |
| 2004/0141958 | A1 | 7/2004 | Steinaa |
| 2004/0147489 | A1 | 7/2004 | Dalton et al. |
| 2004/0147550 | A1 | 7/2004 | Dalton et al. |
| 2004/0156846 | A1 | 8/2004 | Daum et al. |
| 2004/0167103 | A1 | 8/2004 | Dalton et al. |
| 2004/0192626 | A1 | 9/2004 | McSwiggen et al. |

(56) References Cited

U.S. PATENT DOCUMENTS

| | | |
|---|---|---|
| 2004/0241790 A1 | 12/2004 | Henrik et al. |
| 2004/0247680 A1 | 12/2004 | Farokhzad |
| 2004/0248088 A1 | 12/2004 | Raitano et al. |
| 2004/0260092 A1 | 12/2004 | Miller et al. |
| 2004/0260108 A1 | 12/2004 | Dalton et al. |
| 2004/0266688 A1 | 12/2004 | Nayak |
| 2005/0017667 A1 | 1/2005 | Yamamoto |
| 2005/0019870 A1 | 1/2005 | Afar et al. |
| 2005/0019872 A1 | 1/2005 | Afar et al. |
| 2005/0020525 A1 | 1/2005 | McSwiggen et al. |
| 2005/0032733 A1 | 2/2005 | McSwiggen et al. |
| 2005/0033074 A1 | 2/2005 | Dalton et al. |
| 2005/0037075 A1 | 2/2005 | Farokhzad et al. |
| 2005/0048063 A1 | 3/2005 | Ruoslahti et al. |
| 2005/0069910 A1 | 3/2005 | Turner et al. |
| 2005/0079152 A1 | 4/2005 | Bot |
| 2005/0079533 A1 | 4/2005 | Samuelson |
| 2005/0080128 A1 | 4/2005 | Tsukamoto et al. |
| 2005/0100877 A1 | 5/2005 | Xu et al. |
| 2005/0107322 A1 | 5/2005 | OHagan |
| 2005/0122550 A1 | 6/2005 | Plewa et al. |
| 2005/0136258 A1 | 6/2005 | Nie |
| 2005/0142582 A1 | 6/2005 | Doyle |
| 2005/0158390 A1 | 7/2005 | Rana et al. |
| 2005/0191294 A1 | 9/2005 | Arap et al. |
| 2005/0207940 A1* | 9/2005 | Butler et al. ............... 422/73 |
| 2005/0214378 A1 | 9/2005 | Hoarau |
| 2005/0233948 A1 | 10/2005 | D'Amico et al. |
| 2005/0239134 A1 | 10/2005 | Gorenstein |
| 2005/0244863 A1 | 11/2005 | Mir |
| 2005/0249799 A1 | 11/2005 | Jacob et al. |
| 2005/0256071 A1 | 11/2005 | Davis |
| 2005/0260186 A1 | 11/2005 | Bookbinder et al. |
| 2006/0002852 A1 | 1/2006 | Saltzman et al. |
| 2006/0002971 A1 | 1/2006 | Saltzman |
| 2006/0004042 A1 | 1/2006 | Dalton et al. |
| 2006/0009529 A1 | 1/2006 | Dalton et al. |
| 2006/0035966 A1 | 2/2006 | Dalton et al. |
| 2006/0057219 A1 | 3/2006 | Nagasaki |
| 2006/0062787 A1 | 3/2006 | Hitraya |
| 2006/0083711 A1 | 4/2006 | Berry et al. |
| 2006/0110460 A1 | 5/2006 | Ferret |
| 2006/0111271 A1 | 5/2006 | Cerny |
| 2006/0165987 A1 | 7/2006 | Hildgen |
| 2006/0173170 A1 | 8/2006 | Chamberlain et al. |
| 2006/0183931 A1 | 8/2006 | Dalton et al. |
| 2006/0228371 A1 | 10/2006 | Raso |
| 2006/0239907 A1 | 10/2006 | Luzzi et al. |
| 2006/0240093 A1 | 10/2006 | Maclachlan et al. |
| 2006/0241180 A1 | 10/2006 | Dalton et al. |
| 2006/0258628 A1 | 11/2006 | Steiner et al. |
| 2006/0269557 A1 | 11/2006 | Sherman et al. |
| 2006/0276540 A1 | 12/2006 | Dalton et al. |
| 2006/0287547 A1 | 12/2006 | Dalton et al. |
| 2007/0014807 A1 | 1/2007 | Maida |
| 2007/0041901 A1 | 2/2007 | Diener |
| 2007/0043066 A1 | 2/2007 | Sum |
| 2007/0053845 A1 | 3/2007 | Sengupta |
| 2007/0116768 A1 | 5/2007 | Chorny |
| 2007/0184068 A1 | 8/2007 | Renner |
| 2007/0224225 A1 | 9/2007 | IracheGarreta |
| 2007/0225213 A1 | 9/2007 | Kosak |
| 2008/0019908 A1 | 1/2008 | Akitsu |
| 2008/0026000 A1 | 1/2008 | Ennifar |
| 2008/0031899 A1 | 2/2008 | Reddy |
| 2008/0057102 A1 | 3/2008 | Roorda |
| 2008/0081074 A1 | 4/2008 | Gu et al. |
| 2008/0124400 A1 | 5/2008 | Liggins |
| 2008/0171059 A1 | 7/2008 | Howland |
| 2008/0193381 A1 | 8/2008 | Babich |
| 2008/0213377 A1 | 9/2008 | Bhatia |
| 2008/0268063 A1 | 10/2008 | Jon et al. |
| 2008/0299177 A1 | 12/2008 | Hardy |
| 2009/0004118 A1 | 1/2009 | Nie |
| 2009/0028910 A1 | 1/2009 | DeSimone et al. |
| 2009/0061010 A1 | 3/2009 | Zale |
| 2009/0074828 A1 | 3/2009 | Alexis |
| 2009/0117549 A1 | 5/2009 | Tan |
| 2009/0192100 A1 | 7/2009 | Vater |
| 2009/0298710 A1 | 12/2009 | Farokhzad et al. |
| 2010/0022680 A1 | 1/2010 | Karnik |
| 2010/0068285 A1 | 3/2010 | Zale |
| 2010/0068286 A1 | 3/2010 | Troiano |
| 2010/0069426 A1 | 3/2010 | Zale |
| 2010/0092425 A1 | 4/2010 | Von Andrian et al. |
| 2010/0104655 A1 | 4/2010 | Zale |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang et al. |
| 2010/0216804 A1 | 8/2010 | Zale |
| 2010/0226986 A1 | 9/2010 | Grayson |
| 2010/0233251 A1 | 9/2010 | Von Andrian et al. |
| 2010/0266491 A1 | 10/2010 | Farokhzad |
| 2010/0297233 A1 | 11/2010 | Moretti |
| 2010/0303723 A1 | 12/2010 | Farokhzad |
| 2011/0052697 A1 | 3/2011 | Farokhzad |

FOREIGN PATENT DOCUMENTS

| | | |
|---|---|---|
| DK | 0418187 | 3/1991 |
| EP | 0333523 | 9/1989 |
| EP | 1279404 | 1/2003 |
| EP | 1752141 | 2/2007 |
| EP | 1872793 | 1/2008 |
| EP | 1932538 | 6/2008 |
| EP | 2106806 | 10/2009 |
| JP | 2006528954 | 5/2006 |
| KR | 0418916 | 3/2002 |
| KR | 0041712 | 6/2004 |
| WO | WO 88/04300 | 6/1988 |
| WO | WO 90/11364 | 3/1990 |
| WO | 9006430 | 6/1990 |
| WO | 9006433 | 6/1990 |
| WO | 9106286 | 5/1991 |
| WO | 9106287 | 5/1991 |
| WO | 9503356 | 2/1995 |
| WO | 9503357 | 2/1995 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | 98/51325 | 11/1998 |
| WO | 99/01498 | 1/1999 |
| WO | WO 99/34850 | 7/1999 |
| WO | 9955715 | 12/1999 |
| WO | WO 00/21572 | 4/2000 |
| WO | WO 00/27363 | 5/2000 |
| WO | 0032239 | 6/2000 |
| WO | WO 00/44895 | 8/2000 |
| WO | 0059538 | 10/2000 |
| WO | WO 01/75164 | 10/2001 |
| WO | WO 02/18477 | 3/2002 |
| WO | WO 02/076469 | 10/2002 |
| WO | WO 02/076603 | 10/2002 |
| WO | WO 02/100442 | 12/2002 |
| WO | WO 03/004654 | 1/2003 |
| WO | 03033592 | 4/2003 |
| WO | WO 03/028657 | 4/2003 |
| WO | WO 03030941 | 4/2003 |
| WO | WO 03/051304 | 6/2003 |
| WO | 03074679 | 9/2003 |
| WO | WO 03/072637 | 9/2003 |
| WO | WO 03/102708 | 12/2003 |
| WO | 2004009116 | 1/2004 |
| WO | 2004030608 | 4/2004 |
| WO | WO 2004/030608 | 4/2004 |
| WO | WO 2004/071493 | 8/2004 |
| WO | 2004096140 | 11/2004 |
| WO | WO 2004/096998 | 11/2004 |
| WO | 2004105782 | 12/2004 |
| WO | WO 03/000777 | 1/2005 |

(56) References Cited

FOREIGN PATENT DOCUMENTS

| | | |
|---|---|---|
| WO | WO 2005/012407 | 2/2005 |
| WO | WO 2005/028539 | 3/2005 |
| WO | 2005046572 | 5/2005 |
| WO | WO 2005/042573 | 5/2005 |
| WO | WO 2005/072710 | 8/2005 |
| WO | 2005105056 | 11/2005 |
| WO | WO 2005/111192 | 11/2005 |
| WO | 2005112885 | 12/2005 |
| WO | 2005112886 | 12/2005 |
| WO | WO 2005/121181 | 12/2005 |
| WO | 2006025627 | 3/2006 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | 2006093991 | 9/2006 |
| WO | 2006099445 | 9/2006 |
| WO | WO 2006/096754 | 9/2006 |
| WO | WO 2006/117217 | 11/2006 |
| WO | WO 2006/133271 | 12/2006 |
| WO | WO 2006/138463 | 12/2006 |
| WO | 2007001448 A2 | 1/2007 |
| WO | 2007052058 | 1/2007 |
| WO | 2007131972 | 1/2007 |
| WO | WO 2007/021142 | 2/2007 |
| WO | 2007024026 | 3/2007 |
| WO | 2007034479 | 3/2007 |
| WO | 2008043157 | 5/2007 |
| WO | WO 2007/070682 | 6/2007 |
| WO | WO 2007/076371 | 7/2007 |
| WO | WO 2007/084797 | 7/2007 |
| WO | 2007098254 | 8/2007 |
| WO | WO 2007/109364 | 9/2007 |
| WO | WO 2007/118653 | 10/2007 |
| WO | 2007133807 | 11/2007 |
| WO | 2007137117 | 11/2007 |
| WO | 2007144807 A2 | 12/2007 |
| WO | WO 2007/150030 | 12/2007 |
| WO | 2008019142 | 2/2008 |
| WO | 2008041703 | 4/2008 |
| WO | 2008058192 | 5/2008 |
| WO | WO 2008/051291 | 5/2008 |
| WO | 2008105772 | 9/2008 |
| WO | 2008105773 | 9/2008 |
| WO | 2008121949 | 10/2008 |
| WO | 2008124632 | 10/2008 |
| WO | 2008124634 | 10/2008 |
| WO | 2008124639 | 10/2008 |
| WO | 2008147456 | 12/2008 |
| WO | WO 2009/051837 | 4/2009 |
| WO | WO 2009/109428 | 9/2009 |
| WO | 2010005721 | 1/2010 |
| WO | 2010005723 | 1/2010 |
| WO | 2010005725 | 1/2010 |
| WO | 2010005726 | 1/2010 |
| WO | 2010068866 | 6/2010 |
| WO | 2010075072 | 7/2010 |
| WO | 2010114768 | 10/2010 |
| WO | 2010114770 | 10/2010 |
| WO | 2011072218 | 6/2011 |

OTHER PUBLICATIONS

U.S. Appl. No. 12/301,225, filed Nov. 17, 2008, Farokhzad, et al.
U.S. Appl. No. 12/515,465, filed May 5, 2010, Farokhzad, et al.
U.S. Appl. No. 12/526,300, filed Aug. 11, 2010, Farokhzad, et al.
Abad, et al., "Comparison of a Monoclonal Antibody-Based Enzyme-Linked Immunosorbent Assay and Gas Chromatography for the Determination of Nicotine in Cigarette Smoke Condensates", *Anal. Chem.*, 65:3227-3231 (1993).
Ackermand & Cresswell, "Cellular mechanisms governing cross-presentation of exogenous antigens", *Nat. Immunol.*, 5(7):678-684 (2004).
Aime, et al., "Lanthanide(III) chelates for NMR biomedical applications", *Chemical Society Reviews*, 27:19-29 (1998).
Akaishi, et al., "Targeting Chemotherapy Using Antibody-Combined Liposome against Human Pancreatic Cancer Cell-Line", *Tohoku J. Exp. Med.*, 175(1):29-42 (1995).
Allen, et al., "Nano-engineering block copolymer aggregates for drug delivery.", *Colloids Surfaces B-Biointerfaces*, 16:3-27 (1999).
Allison, et al., "The mode of action of immunological adjuvants.", *Dev. Biol. Stand.*, 92:3-11 (1998).
Altschul, et al., "Basic local alignment search tool.", *J. Mol Biol.*, 215(3):403-10 (1990).
Altschul, et al., "Gapped Blast and PSI-Blast: a new generation of protein database search programs.", *Nucleic Acids Res.*, 25(17):3389-3402 (1997).
Angelucci, et al., "Neuroendocrine transdifferentiation induced by VPA is mediated by PPAR☐ activation and confers resistance to antiblastic therapy in prostate carcinoma", *The Prostate*, 68(6):588-598 (2008).
Astete and Sabliov, "Synthesis and characterization of PLGA nanoparticles", *J. Biomat. Sci.,-Polymer Ed.*, 17:247-289 (2006).
Atkinson, et al., "Conjugation of folate via gelonin carbohydrate residues retains ribosomal-inactivating properties of the toxin and permits targeting to folate receptor positive cells.", *J. Blot Chem.*, 276(30):27930-27935 (2001).
Baba, et al., "Human neutralizing monoclonal antibodies of the IgG1 subtype protect against mucosal simian-human immunodeficiency virus infection.", *Nat. Med.*, 6(2):200-206 (2000).
Babaian, et al., "Radioimmunological imaging of metastatic prostate cancer with 111indium-labeled monoclonal antibody PAY 276.", *J. Urol.*, 137(3):439-443 (1987).
Bachmann, et al., "T helper cell-independent neutralizing B cell response against vesicular stomatitis virus: role of antigen patterns in B cell induction?", *Eur. J. Immunol.*, 25(12):3445-3451 (1995).
Bagalkot, et al., "An Aptamer-Doxorubicin Physical Conjugate as a Novel Targeted Drug-Delivery Platform", *Angew. Chem. Int. Ed.*, 45(48):8149-8152 (2006).
Bander, et al., "Targeting metastatic prostate cancer with radiolabeled monoclonal antibody J591 to the extracellular domain of prostate specific membrane antigen.", *J. Urol.*, 170(5):1717-1721 (2003).
Barchet, et al., "Virus-induced interferon alpha production by a dendritic cell subset in the absence of feedback signaling in vivo.", *J. Exp. Med.*, 195(4):507-516 (2002).
Barrera, et al., "Synthesis and RGD peptide modification of a new biodegradable copolymer: poly(lactic acid-co-lysine)", *J. Am. Chem. Soc.*, 115(23):11010-11011 (1993).
Bauer, et al., "SMS 201-995: a very potent and selective octapeptide analogue of somatostatin with prolonged action.", *Life Sci.*, 31(11):1133-1140 (1982).
Beaureparie, et al., "Functionalized Fluorescent Oxide Nanoparticles: Artificial Toxins for Sodium Channel Targeting and Imaging at the Single-Molecule Level", *Nano Letters*, 4(11):2079-2083 (2004).
Bennett, et al., "Inhibition of the Aminopeptidase from Aeromonas Proteolytica by I-Leucinephosphonic Acid, a Transition State Analogue of Peptide Hydrolysis", *J. Am. Chem. Soc.*, 120(46):12139-12140 (1998).
Binetruy-Tournaire, et al., "Identification of a peptide blocking vascular endothelial growth factor (VEGF)-mediated angiogenesis.", *EMBO J.*, 19(7):1525-1533 (2000).
Bjerke, et al., "Comparison of monoclonal and polyclonal antibodies to continine in nonisotopic and isotopic immunoassays", *J. Immunol. Meth.*, 96:239-246 (1987).
Boes, et al., "T-cell engagement of dendritic cells rapidly rearranges MHC class II transport.", *Nature*, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8 + T cell tolerance.", *J. Exp. Med.*, 196(12):1627-1638 (2002).
Bottausci, et al., "Mixing in the shear superposition micromixer: three-dimensional analysis", *Philosophical Transactions of the*

(56) References Cited

OTHER PUBLICATIONS

*Royal Society of London Series a-Mathematical Physical and Engineering Sciences*, 362:1001-1018 (2004).
Boussif, et al., "A versatile vector for gene and oligonucleotide transfer into cells in culture and in vivo: polyethylenimine.", *Proc. Natl. Acad. Sci.*, USA, 1995, 92:7297-7301 (1995).
Bozzacco, et al., "DEC-205 receptor on dendritic cells mediates presentation of HIV gag protein to CD8+ T cells in a spectrum of human MHC I haplotypes.", *Proc. Natl. Acad. Sci.*, USA, 104(4):1289-1294 (2007).
Brito, et al., "Nanoparticulate carriers for the treatment of coronary restenosis.", *Int J Nanomedicine*, 2(2):143-161 (2007).
Burmeister, et al., "Direct in vitro selection of a 2'-0-methyl aptamer to VEGF.", *Chem Biol*, 12(1):25-33 (2005).
Carino, et al., "Nanosphere based oral insulin delivery," *J. Control. Release*, 65(1-2):261-9 (2000).
Casola, et al., "B cell receptor signal strength determines B cell fate.", *Nat. Immunol*, 5(3):317-327 (2004).
Castro & Prieto, "Nicotine Antibody Production: Comparison of two nicotine conjugates in different animal species", *Biochem. Biophys. Res. Comm.*, 67(2):583-589 (1975).
Castro, et al., "Nicotine Antibodies: Comparison of Ligand Specificities of Antibodies Produced against Two Nicotine Conjugates", *Eur. J. Biochem.*, 104:331-340 (1980).
Chacon, et al., "Optimized preparation of poly D,L (lactic-glycolic) microspheres and nanoparticles for oral administration", *Int'l J. Pharmaceutics*, 141:81-91 (1996).
Chaires, et al., "Preferential binding of daunomycin to 5'ATCG and 5'ATGC sequences revealed by footprinting titration experiments.", *Biochemistry*, 29(26):6145-6153 (1990).
Chang, et al., "Five Different Anti-Prostate-specific Membrane Antigen (PSMA) Antibodies Confirm PSMA Expression in Tumor-associated Neovasculature", *Cancer Res.*, 59:3192-3198 (1999).
Cheng, et al., "Formulation of functionalized PLGA-PEG nanoparticles for in vivo targeted drug delivery.", *Biomaterials*, 28(5):869-876 (2007).
Christian, et al., "Nucleolin expressed at the cell surface is a marker of endothelial cells in angiogenic blood vessels.", *J. Cell Biol.*, 163(4):871-878 (2003).
Chu, et al., "Aptamer mediated siRNA delivery", *Nuc. Acid Res.*, 34:e73 (2006).
Chu, et al., "Labeling tumor cells with fluorescent nanocrystal-aptamer bioconjugates.", *Biosens. & Bioelectron.*, 21:1859-1866 (2006).
Clark, "The reticulum of lymph nodes in mice studied with the electron microscope.", *Am. J. Anat.*, 110:217-257 (1962).
Connor, et al., "Ex vivo evaluation of anti-EpCAM immunocytokine huKS-IL2 in ovarian cancer.", *J. Immunother.*, 27(3):211-219 (2004).
Croy and Kwon, "Polymeric micells for drug delivery", *Curr. Pharm. Design*, 12:4669-4684 (2006).
D'Antonio, et al., "Longitudinal analysis of androgen deprivation of prostate cancer cells identifies pathways to androgen independence", *The Prostate*, 68(7):698-714 (2008).
Dang and Rock, "Stimulation of B lymphocytes through surface Ig receptors induces LFA-1 and ICAM-1-dependent adhesion.", *J. Immunol.*, 146(10):3273-3279 (1991).
De Graaf, et al., "A fully human anti-Ep-CAM scFv-beta-glucuronidase fusion protein for selective chemotherapy with a glucuronide prodrug.", *Br. J. Cancer*, 86(5):811-818 (2002).
De Jaeghere, et al., "Freeze-drying and lyopreservation of diblock and triblock polyllactic acid)-polyethylene oxide) (PLA-PEO) copolymer nanoparticles.", *Pharm. Dev. Technol.*, 5(4):473-483 (2000).
Delemarre, et al., "Repopulation of macrophages in popliteal lymph nodes of mice after liposome-mediated depletion.", *J. Leukoc. Biol.*, 47(3):251-257 (1990).
Demello and Demello, "Microscale reactors: nanoscale products.", *Lab on a Chip*, 4(2):11N-15N (2004).
Demello, "Control and detection of chemical reactions in microfluidic systems.", *Nature*, 442(7101):394-402 (2006).

Deming, et al., "Facile synthesis of block copolypeptides of defined architecture.", *Nature*, 390(6658):386-389(1997).
Derfus, et al., "Intracellular Delivery of Quantum Dots for Live Cell Labeling and Organelle Tracking", *Advanced Materials*, 16:961-966 (2004).
Dimarco and Arcamone, "DNA complexing antibiotics: Daunomycin, adriamycin and their derivates.", *Arzneim-Forsch. (Drug Res.)*, 25:368-375 (1975).
Ding, et al., "Syntheses of conformationally constricted molecules as potential NAALADase/PSMA inhibitors.", *Org. Lett.*, 6(11):1805-1808 (2004).
Dinkla, et al., "Identification of a streptococcal octapeptide motif involved in acute rheumatic fever.",*J. Biol. Chem.*, 282(26):18686-18693 (2007).
Dykxhoorn, et al., "Killing the messenger: short RNAs that silence gene expression.", *Nat. Rev. Mol. Cell Biol.*, 4(6):457-467 (2003).
Eklund, et al., "Denileukin diftitox: a concise clinical review.", *Expert Rev. Anticancer Thor.*, 5(1):33-38 (2005).
Elbashir, et al., "RNA interference is mediated by 21—and 22-nucleotide RNAs.", *Genes Dev.*, 15(2):188-200 (2001).
Eldridge, et al., "Biodegradable microspheres as a vaccine delivery system," *Mol. Immunol.*, 28(3):287-94 (1991).
Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370(2006).
Farokhzad, et al., "Nanoparticle-Aptamer Bioconjugates: A New Approach for Targeting Prostate Cancer Cells," *Cancer Research*, 64:7668-7672 (2004).
Farokhzad, et al., "Nanoparticle—aptamer bioconjugates for cancer targeting", *Expert Opin. Drug Delivery*, 3(3):311-324 (2006).
Farokhzad, et al., "Targeted nanoparticle-aptamer bioconjugates for cancer chemotherapy in vivo.", *Proc. Natl. Acad. ScL*, USA, 103(16):6315-6320 (2006).
Farr, et al., "The structure of the sinus wall of the lymph node relative to its endocytic properties and transmural cell passage.",*Am. J. Anat.*, 157(3):265-284 (1980).
Fire, et al., "Potent and specific genetic interference by double-stranded RNA in Caenorhabditis elegans.", *Nature*, 391(6669):806-811 (1998).
Fonseca, et al., "Paclitaxel-loaded PLGA nanaparticles: preparation, physicochemical characterization and in vitro anti-tumoral activity.", *J. Control. Release*, 83(2):273-286 (2002).
Fracasso, et al., "Anti-tumor effects of toxins targeted to the prostate specific membrane antigen.", *Prostate*, 53(11:9-23 (2002).
Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).
Frankel, et al., "Phase I trial of a novel diphtheria toxin/granulocyte macrophage colony-stimulating factor fusion protein (DT388GMCSF) for refractory or relapsed acute myeloid leukemia.", *Clin. Cancer Res.*, 8(5):1004-1013 (2002).
Frederick, et al., "Structural comparison of anticancer drug-DNA complexes: adriamycin and daunomycin.", *Biochemistry*, 29(10):2538-2549 (1990).
Froidevaux, et al., "Somatostatin analogs and radiopeptides in cancer therapy.", *Biopolymers*, 66(3):161-183 (2002).
Fujita, et al., "Cytokine profiling of prostatic fluid from cancerous prostate glands identifies cytokines associated with extent of tumor and inflammation", *The Prostate*, 68(8):872-882 (2008).
Gao, et al., "A method for the generation of combinatorial antibody libraries using pIX phage display," *Proc. Natl. Acad. Sci. U.S.A.*, 99(20): 12612-6 (2002).
Gao, et al., "In vivo cancer targeting and imaging with semiconductor quantum dots.", *Nat. Biotechnol.*, 22(8):969-976 (2004).
Gao, et al., "In vivo molecular and cellular imaging with quantum dots.", *Curr. Op. Biotechnol.*, 16:63-72 (2005).
Gershlick, "Treating atherosclerosis: local drug delivery from laboratory studies to clinical trials," *Atherosclerosis*, 160(2): 259-71 (2002).

(56) References Cited

OTHER PUBLICATIONS

Gillies, et al., "An anti-CD20-IL-2 immunocytokine is highly efficacious in a SCID mouse model of established human B lymphoma.", *Blood*, 105(10)3972-3978 (2005).

Grauer, et al., "Identification, purification, and subcellular localization of prostate-specific membrane antigen PSM' protein in the LNCaP prostatic carcinoma cell line.", *Cancer Res.*, 58(21):4787-4789 (1998).

Gref, et al., "Biodegradable long-circulating polymeric nanospheres.", *Science*, 263(5153):1600-1603 (1994).

Haensler, et al., "Polyamidoamine cascade polymers mediate efficient transfection of cells in culture", *Bioconjugate Chem.*, 4(5):372-379 (1993).

Haj, et al., "New findings in the study on the intercalation of bisdaunorubicin and its monomeric analogues with naked and nucleus DNA.", *Chem. Biol. Interact.*, 145(3):349-358 (2003).

Hanes, et al., "Polymer microspheres for vaccine delivery.", *Pharm. Biotechnol.*, 6:389-412 (1995).

Hangartner, et al., "Antiviral immune responses in gene-targeted mice expressing the immunoglobulin heavy chain of virus-neutralizing antibodies.", *Proc. Natl. Acad. Sci.*, USA, 100:12883:12888 (2003).

Hannon, et al., "Unlocking the potential of the human genome with RNA interference", *Nature*, 431(7006):371-378 (2004).

Harada and Kataoka, "Supramolecular assemblies of block copolymers in aqueous media as nanocantainers relevant to biological applications", *Progress Polymer Sci.*, 31(11):949-982 (2006).

Harper, et al., "Efficacy of a bivalent L1 virus-like particle vaccine in prevention of infection with human papillomavirus types 16 and 18 in young women: a randomised controlled trial.", *Lancet*, 364(9447):1757-1765 (2004).

Haseloff and Gerlach, "Simple RNA enzymes with new and highly specific endoribonuclease activities.", *Nature*, 334(6183):585-591 (1988).

Hawiger, et al., "Dendritic cells induce peripheral T cell unresponsiveness under steady state conditions in vivo.", *J. Exp. Med.* 94(6):769-779 (2001).

He, et al., "A microRNA polycistron as a potential human oncogene," *Nature*, 435(7043): 828-833 (2005).

Hélène, "The anti-gene strategy: control of gene expression by triplex-forming-oligonucleotides.", *Anticancer Drug Des.* 6(6):569-584 (1991).

Helene, et al., "Control of gene expression by triple helix-forming oligonucleotides. The antigene strategy.", *Ann, N.Y. Acad. Sci.* 660:27-36 (1992).

Hermann and Patel, "Adaptive recognition by nucleic acid aptamers," *Science*, 287: 820-825 (2000).

Hieda, et al., "Active Immunization Alters the Plasma Nicotine Concentration in Rats", *J. Pharmacol. Exp. Therapeutics*, 283:1076-1081 (1997).

Hieda, et al., "Immunization of rats reduces nicotine distribution to brain", *Psychopharmacology*, 143:150-157 (1999).

Horoszewicz, et al., "Monoclonal antibodies to a new antigenic marker in epithelial prostatic cells and serum of prostatic cancer patients.", *Anticancer Res.*, 7(5B):927-935 (1987).

Houghton, "General method for the rapid solid-phase synthesis of large numbers of peptides: Specificity of antigen-antibody interaction at the level of individual amino acids", *Immunol.*, 82:5131-5135 (1985).

Jackson, et al., "Design and pharmacological activity of phosphinic acid based NAALADase inhibitors.", *J. Med. Chem.*, 44(24):4170-4175 (2001).

Jackson, et al., "Design of NAALADase inhibitors: a novel neuroprotective strategy.", *Curr. Med. Chem.*, 8(8):949-957 (2001).

Johnson and Prud'Homme, "Mechanism for rapid self-assembly of block copolymer nanoparticles.", *Phys. Rev. Lett.*, 91(11):118302 (2003).

Jones and Leroux, "Polymeric micelles—a new generation of colloidal drug carriers", *Eur. J. Pharmaceutics Biopharmaceutics*, 48:101-111 (1999).

Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).

Junt, et al., "Subcapsular sinus macrophages in lymph nodes clear lymph-borne viruses and present them to antiviral B cells", *Nature*, 450:110-116 (2007).

Kabanov, et al., "DNA Complexes with Polycations for the Delivery of Genetic Material into Cells", *Bioconjugate Chem.*, 6(1):7-20 (1995).

Kamentsky, "Laser scanning cytometry.", *Methods Cell Biol.*, 63:51-87 (2001).

Kanashiro, et al., "Inhibition of mutant p53 expression and growth of DMS-153 small cell lung carcinoma by antagonists of growth hormone-releasing hormone and bombesin.", *Proc. Natl. Acad. Sci.*, USA, 100(26):15836-15841 (2003).

Karlin and Altschul, "Applications and statistics for multiple high-scoring segments in molecular sequences.", *Proc. Natl Acad. Sci. USA*, 90(12):5873-5877 (1993).

Karlin and Altschul, "Methods for assessing the statistical significance of molecular sequence features by using general scoring schemes.", *Proc. Natl Acad Sci.* USA, 87:2264-2268 (1990).

Karrer, et al., "On the key role of secondary lymphoid organs in antiviral immune responses studied in alymphoplastic (aly/aly) and spleenless (Hox11(•)/•) mutant mice.", *J. Exp. Med.*, 185(12):2157-2170 (1997).

Kelly, et al., "The Optical Properties of Metal Nanoparticles: The Influence of Size, Shape, and Dielectric Environment", *J. Phys. Chem. B.*, 107(3):668-677 (2003).

Khademhosseini, et al., "Cell docking inside microwells within reversibly sealed microfluidic channels for fabricating multiphenotype cell arrays," *Lab Chip*, 5(12):1380-6 (2005).

Knight, et al., "Hydrodynamic Focusing on a Silicon Chip: Mixing Nanoliters in Microseconds", *Phys. Rev. Lett.*, 80:3863-3866 (1998).

Köhrer and Rajbhandary, "Proteins carrying one or more unnatural amino acids," In Ibba, et al., (eds.), *Aminoacyl-tRNA Synthetases*, Landes Bioscience, Chapter 31 (2005).

Köhrer, et al., "Coinplete set of orthogonal 21st aminoacyl-tRNA synthetase-amber, ochre and opal suppressor tRNA pairs: concomitant suppression of three different termination codons in an mRNA in mammalian cells.", *Nucleic Acids Res.*, 32(21):6200-6211 (2004).

Köhrer, et al., "Import of amber and ochre suppressor tRNAs into mammalian cells: a general approach to site-specific insertion of amino acid analogues into proteins.", *Proc. Natl. Acad. Sci.*, USA, 98(25):14310-14315 (2001).

Koivunen, et al., "Phage libraries displaying cyclic peptides with different ring sizes: ligand specificities of the RGD-directed integrins.", *Biotechnology* (NY), 13(3):265-270 (1995).

Koivunen, et al., "Tumor targeting with a selective gelatinase inhibitor", *Nat. Biotechnol.*, 17:768-774 (1999).

Konan, et al., "Preparation and characterization of sterile sub-200 nm meso-tetra(4-hydroxylphenyl)porphyrin-loaded nanoparticles for photodynamic therapy", *Eur. J. Pharmaceutics Biopharmaceutics*, 55:115-124 (2003).

Kozikowski, et al., "Synthesis of urea-based inhibitors as active site probes of glutamate carboxypeptidase II: efficacy as analgesic agents.", *J. Med. Chem.*, 47(7):1729-1738(2004).

Krieg, et al., "CpG motifs in bacterial DNA trigger direct B-cell activation.", *Nature*, 374(6522):546-549 (1995).

Kreitman, et al., "Efficacy of the anti-CD22 recombinant immunotoxin BL22 in chemotherapy-resistant hairy-cell leukemia.", *N. Engl J. Med.*, 345(4):241-347 (2001).

Kreitman, et al., "Phase I trial of recombinant immunotoxin anti-Tac(Fv)-PE38 (LMB-2) in patients with hematologic malignancies.", *J. Clin. Oncol.*, 18(8):1622-1636 (2000).

Kukowska-Latallo, et al., "Efficient transfer of genetic material into mammalian cells using Starburst polyamidoamine dendrimers", *Proc. Natl. Acad. Sci.*, USA, 93(10):4897-4902 (1996).

Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).

(56) References Cited

OTHER PUBLICATIONS

Kwon, et al., "Pseudopoly(amino acids): A study of the synthesis and characterization of poly(acyl-hydroxyproline-esters)", *Macromolecules*, 22:3250-3255 (1989).
Laakkonen, et al., "Antitumor activity of a homing peptide that targets tumor lymphatics and tumor cells.", *Proc. Natl. Acad. Sci.*, USA, 101(25):9381-9386 (2004).
Labhasetwar, et al., "Arterial uptake of biodegradable nanoparticles: Effect of surface modifications ," *J. Pharm. Sci.*, 87(10):1229-34 (1998).
Langer, "Biomaterials in drug delivery and tissue engineering: one laboratory's experience.", *Acc. Chem. Res.*, 33(2):94-101 (2000).
Langer, "New methods of drug delivery," *Science*, 249(4976):1527-33 (1990).
Langer, "Selected advances in drug delivery and tissue engineering", *J. Control. Release*, 62:7-11 (1999).
Langone, et al., "Nicotine and its metabolites. Radioimmunoassays for nicotine and cotinine", *Biochem.*, 12(24):5025-5030 (1973).
Langone & Van Vunakis, "Radioimmunoassay of Nicotine, Cotinine, and □-(3-Pyridyl)- □ -oxo-N-methylbutyramide", *Met. Enzymol.*, 84:628-640 (1982).
Leamon, et al., "Cytotoxicity of folate-Pseudomonas exotoxin conjugates toward tumor cells. Contribution of translocation domain.", *J. Biol. Chem.*, 268(33):24847-24854 (1993).
Leamon, et al., "Selective targeting of malignant cells with cytotoxin-folate conjugates.", *J. Drug Target.*, 2(2):101-112 (1994).
Leopold, et al., "Fluorescent virions: dynamic tracking of the pathway of adenoviral gene transfer vectors in living cells.", *Human Gene Therapy*, 9(3):367-378 (1998).
Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).
Leucuta, et al., "Albumin microspheres as a drug delivery system for epirubicin: pharmaceutical, pharmacokinetic and biological aspects," *International Journal of Pharmaceutics*, 41: 213-7 (1988).
Lim, et al., "A Self-Destroying Polycationic Polymer: Biodegradable Poly(4-hydroxy-l-proline ester)", *J. Am. Chem. Soc.*, 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).
Lin, et al., "A microRNA polycistron as a potential human oncogene p828", *Nature*, 435(7043):828-833 (2005).
Lin, et al., "Well-Ordered Mesoporous Silica Nanoparticles as Cell Markers", *Chem. Mater.*, 17:4570-4573 (2005).
Liu, et al., "Cell-Surface labeling and internalization by a fluorescent inhibitor of prostate-specific membrane antigen", *The Prostate*, 68(9):955-964 (2008).
Liu, et al., "Constitutive and antibody-induced internalization of prostate-specific membrane antigen.", *Cancer Res.*, 58(18):4055-4060 (1998).
Liu, et al., "Folate-targeted enzyme prodrug cancer therapy utilizing penicillin-V amidase and a doxorubicin prodrug.", *J. Drug Target.*, 7:43-53 (1999).
Liu, et al., "Hypermethylation of MCAM gene is associated with advanced tumor stage in prostate cancer", *The Prostate*, 68(4):418-426 (2008).
Liu, et al., "Monoclonal antibodies to the extracellular domain of prostate-specific membrane antigen also react with tumor vascular endothelium.", *Cancer Res.*, 57(17):3629-3634 (1997).
Low, et al., "Folate receptor-targeted drugs for cancer and inflammatory diseases.", *Adv. Drug Deliv. Rev.*, 56(8):1055-1058 (2004).
Lu, et al., "MicroRNA expression profiles classify human cancers", *Nature*, 435(7043):834-838 (2005).
Ludewig, et al., "Induction of optimal anti-viral neutralizing B cell responses by dendritic cells requires transport and release of virus particles in secondary lymphoid organs.", *Eur. J. Immunol.*, 30(1):185-196 (2000).
Lupold, et al., "Identification and characterization of nuclease-stabilized RNA molecules that bind human prostate cancer cells via the prostate-specific membrane antigen.", *Cancer Res.*, 62(14):4029-4033 (2002).
Lyu, et al., "The immunocytokine scFv23/TNF sensitizes HER-2/neu-overexpressing SKBR-3 cells to tumor necrosis factor (TNF) via up-regulation of TNF receptor-1.", *Mol. Cancer Ther.*, 4(8):1205-1213 (2005).
Maher, "DNA triple-helix formation: An approach to artificial gene repressors?", *Bioassays* 14:807-815 (1992).
Majer, et al., "Synthesis and biological evaluation of thiol-based inhibitors of glutamate carboxypeptidase II: discovery of an orally active GCP II inhibitor.", *J. Med. Chem.*, 46(10):1989-1996 (2003).
Manolova, et al., "Nanoparticles target distinct dendritic cell populations according to their size", *Eur. J. Immunol.*, 38:1404-1413 (2008).
Manz, et al., "Capillary electrophoresis on a chip", *J. Chromatography*, 593:253-258 (1992).
Mathiowitz, et al., "Polyanhydride Microspheres as Drug Carriers I. Hot Melt Encapsulation", *J. Control. Release*, 5:13-22 (1987).
Mathiowitz, et al., "Novel microcapsules for delivery systems", *Reactive Polymers*, 6:275-283 (1987).
Mathiowitz, et al., "Polyanhydride Microspheres as Drug Carriers. II.Microencapsulation by Solvent Removal", *J. Appl. Polymer Sci.*, 35:755-774 (1988).
Mattheakis, et al., "Optical coding of mammalian cells using semiconductor quantum dots.", Analytical Biochemistry, 327(2):200-208 (2004).
Maung, et al., "Probing for a hydrophobic a binding register in prostate-specific membrane antigen with phenylalkylphosphonamidates.", *Bioorg. Med. Chem.*, 12(18):4969-4979 (2004).
McDevitt, et al., "An alpha-particle emitting antibody ([213Bi]J591) for radioimmunotherapy of prostate cancer.", *Cancer Res.*, 60(21):6095-6100 (2000).
McDevitt, et al., "Tumor therapy with targeted atomic nanogenerators.", *Science*, 294(5546):1537-1540 (2001).
Mead, et al., "Laboratory vector competence of black flies (Diptera:Simuliidae) for the Indiana serotype of vesicular stomatitis virus.", *Ann. N.Y. Acad. Sci.*, 916:437-443 (2000).
Meister, et al., "Mechanisms of gene silencing by double-stranded RNA.", *Nature*, 431(7006):343-349 (2004).
Melani, et al., "Targeting of interleukin 2 to human ovarian carcinoma by fusion with a single-chain Fv of antifolate receptor antibody.", *Cancer Res.*, 58(18):4146-4154 (1998).
Mempel, et al., "T-cell priming by dendritic cells in lymph nodes occurs in three distinct phases.", *Nature*, 427(6970):154-159 (2004).
Metelitsa, et al., "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).
Meyers, et al., "Development of monoclonal antibody imaging of metastatic prostatic carcinoma.", *Prostate*, 14(3):209-220 (1989).
Milligan and Uhlenbeck, "Synthesis of small RNAs using T7 RNA polymerase," *Methods in Enzymology*, 180: 51-62 (1989).
Moghimi, et al, "Long-circulating and target-specific nanoparticles: theory to practice," *Pharmacol. Rev.*, 53(2): 283-318.
Mulligan, "The basic science of gene therapy," *Science*, 260(5110):926-32 (1993).
Murphy, et al., "Isolation and characterization of monoclonal antibodies specific for the extracellular domain of prostate specific membrane antigen.", *J. Urol.*, 160(6 Pt 2):2396-2401 (1998).
Murray, et al., "Synthesis and characterization of monodisperse nanocrystals and close-packed nanocrystal assemblies", *Ann. Rev. Mat. Sci.*, 30:545-610 (2000).
Myers and Miller, *CABIOS* (1988).
Nan, et al., "Dual function glutamate-related ligands: discovery of a novel, potent inhibitor of glutamate carboxypeptidase II possessing mGluR3 agonist activity.", *J. Med. Chem.*, 43151:772-774 (2000).
Neidle, "The molecular basis for the action of some DNA-binding drugs.", *Prog. Med. Chem.*, 16:151-221 (1979).

(56) References Cited

OTHER PUBLICATIONS

Nguyen and Wu, "Micromixers—a review.", *J. Micromechan. Microeng.*, 15:R1 (2005).
Notter, et al., "Targeting of a B7-1 (C080) immunoglobulin G fusion protein to acute myeloid leukemia blasts increases their costimulatory activity for autologous remission T cells.", *Blood*, 97(10):3138-3145 (2001).
Ochsenbein, et al., "Protective T cell-independent antiviral antibody responses are dependent on complement.", *J. Exp. Med.*, 190(8):1165-1174 (1999).
Ochsenbein, et al., "Control of early viral and bacterial distribution and disease by natural antibodies.", *Science*, 286(5447):2156-2159 (1999).
O'Donnell, et al., "c-Myc-regulated microRNAs modulate E2F1 expression," *Nature*, 435(7043): 839-843 (2005).
Okada, et al., "Antigen-engaged B cells undergo chemotaxis toward the T zone and form motile conjugates with helper T cells.", *PLoS Biol.*, 3(6):e150 (2005).
Oliver, et al., "Conformational and SAR analysis of NAALADase and PSMA inhibitors.", *Bioorg. Med. Chem.*, 11(20):4455-4461 (2003).
Pape, et al., "The humoral immune response is initiated in lymph nodes by B cells that acquire soluble antigen directly in the follicles.", *Immunity*, 26(4):491-502 (2007).
Papisov, "Acyclic Polyacetals from Polysaccharides: Biomimetic Biomedical "Stealth" Polymers", *ACS Symposium Series*, 786:301-314 (2001).
Parekh, et al., "Biomarkers for Prostate Cancer Detection", *The Journal of Urology*, 178(6):2252-2259 (2007).
Pasqualini, et al., "Aminopeptidase N is a receptor for tumor-homing peptides and a target for inhibiting angiogenesis.", *Cancer Res.*, 60(3):722-727 (2000).
Patri, et al., "Synthesis and in Vitro Testing of J591 Antibody—Dendrimer Conjugates for Targeted Prostate Cancer Therapy", *Bioconj Chem.*, 15:1174-1181 (2004).
Pellegrino, et al., "On the development of colloidal nanoparticles towards multifunctional structures and their possible use for biological applications.", *Small*, 1(1):48-63 (2005).
Pfohl, et al., "Trends in microfluidics with complex fluids.", *Chemphyschem*, 4(12):1291-1298 (2003).
Phillips, et al., "Enhanced antibody response to liposome-associated protein antigens: preferential stimulation of IgG2a/b production.", *Vaccine*, 10(3):151-158 (1992).
Porkka, et al., "A fragment of the HMGN2 protein homes to the nuclei of tumor cells and tumor endothelial cells in vivo.", *Proc. Natl. Acad. Sci.*, USA, 99(11):7444-7449(2002).
Putnam, et al., "Poly(4-hydroxy-l-proline ester): Low-Temperature Polycondensation and Plasmid DNA Complexation", *Macromolecules*, 32(11):3658-3662 (1999).
Qi, et al., "Extrafollicular activation of lymph node B cells by antigen-bearing dendritic cells", *Science*, 312(5780):1672-1676 (2006).
Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).
Reddy, et al., "Exploiting lymphatic transport and complement activation in nanoparticle vaccines", *Nat. Biotech.*, 25(10):1159-1164 (2007).
Reif, et al., "Balanced responsiveness to chemoattractants from adjacent zones determines B-cell position.", *Nature*, 416(6876):94-99 (2002).
Reiher, et al., "Inhibition of tumor growth by systemic treatment with thrombospondin-1 peptide mimetics.", *Int. J. Cancer*, 98(5):682-689 (2002).
Reubi, et al., "Peptide receptors as molecular targets for cancer diagnosis and therapy.", *Endocr. Rev.*, 24(4):389-427 (2003).
Reynolds, et al., "Rational siRNA design for RNA interference.", *Nat. Biotechnol.*, 22(3):326-330 (2004).
Robbins, et al., "Stable expression of shRNAs in human CD34 + progenitor cells can avoid induction of interferon responses to siRNAs in vitro", *Nature Biotechnology*, 24(5):566-571 (2006).
Robinson, et al., "LEAPT: lectin-directed enzyme-activated prodrug therapy.", *Proc. Natl. Acad. Sci.*, USA, 101(40):14527-14532 (2004).
Roost, et al., "Mapping of the dominant neutralizing antigenic site of a virus using infected cells.", *J. Immunol. Methods*, 189(2):233-242 (1996).
Rossbacher and Shlomchik, "The B cell receptor itself can activate complement to provide the complement receptor 1/2 ligand required to enhance B cell immune responses in vivo.", *J. Exp. Med.*, 198(4):591-602 (2003).
Sampson, et al., "Progress report of a Phase I study of the intracerebral microinfusion of a recombinant chimeric protein composed of transforming growth factor (TGF)-alpha and a mutated form of the Pseudomonas exotoxin termed PE-38 (TP-38) for the treatment of malignant brain tumors.", *J. Neurooncol*, 65(1):27-35 (2003).
Santoyo, et al., "Highly specific and accurate selection of siRNAs for high-throughput functional assays.", *Bioinformatics*, 21(8):1376-1382 (2005).
Sarver, et al., "Ribozymes as potential anti-HIV-1 therapeutic agents.", *Science* 247(4947):1222-1225 (1990).
Schally, et al., "Peptide analogs in the therapy of prostate cancer.", *Prostate*, 45(2):158-166 (2000).
Schultz, "Plasmon resonant particles for biological detection", *Curr. Op. Biotechnol.*, 14:13-22 (2003).
Schultz, et al., "Single-target molecule detection with nonbleaching multicolor optical immunolabels.", *Proc. Natl. Acad. Sci.*, USA, 97(3):996-1001(2000).
Shaida, et al., "Expression of BNIP3 correlates with hypoxia-inducible factor (HIF)-1☐, , HIF-2☐ and the androgen receptor in prostate cancer and is regulated directly by hypoxia but not androgens in cell lines", *The Prostate*, 68(3):336-343 (2008).
Shen, et al., "Enhanced and prolonged cross-presentation following endosomal escape of exogenous antigens encapsulated in biodegradable nanoparticles", *Immunol.*, 117:78-88 (2006).
Shestopalov, et al., "Multi-step synthesis of nanoparticles performed on millisecond time scale in a microfluidic droplet-based system.", *Lab on a Chip*, 4(4):316-321 (2004).
Shiow, et al., "CD69 acts downstream of interferon-alpha/beta to inhibit S1P1 and lymphocyte egress from lymphoid organs.", *Nature*, 440(7083):540-544 (2006).
Silver, et al., "Prostate-specific membrane antigen expression in normal and malignant human tissues.", *Clin. Cancer Res.*, 3(1):81-85 (1997).
Smith-Jones, et al., "In vitro characterization of radiolabeled monoclonal antibodies specific for the extracellular domain of prostate-specific membrane antigen.", *Cancer Res.*, 60(18):5237-5243 (2000).
Sorel, et al., "Preclinical and clinical development of immunocytokines.", *Curr. Opin. Investig. Drugs*, 4(6):696-700 (2003).
Song, et al., "A Microfluidic System for Controlling Reaction Networks in Time", *Angewandte Chemie-Int'l Ed.*, 42:768-772 (2003).
Spooner, et al., "A novel vascular endothelial growth factor-directed therapy that selectively activates cytotoxic prodrugs.", *Br. J. Cancer*, 88(10):1622-1630 (2003).
Stoermer, et al., "Synthesis and biological evaluation of hydroxamate-Based inhibitors of glutamate carboxypeptidase II.", *Bioorg. Med. Chem. Lett.*, 13(13):2097-2100 (2003).
Storm, et al., "Surface Modification of Nanoparticles to Oppose Uptake by the Mononuclear Phagocyte System", *Adv. Drug Deliv. Rev.*, 17:31-48 (1995).
Stroock, et al., "Chaotic mixer for microchannels.", *Science*, 295(5555):647-651 (2002).
Sutcliffe, et al., "Antibodies that react with predetermined sites on proteins", *Science*, 219:660-666 (1983).
Tang, et al., "In Vitro Gene Delivery by Degraded Polyamidoamine Dendrimers", *Bioconjugate Chem.*, 7:703-714 (1996).
Tang, et al., "Prostate targeting ligands based on N-acetylated alpha-linked acidic dipeptidase.", *Biochem. Biophys. Res. Commun.*, 307(1):8-14 (2003).

(56) References Cited

OTHER PUBLICATIONS

Taylor, et al., "Macrophage receptors and immune recognition.", *Annu. Rev. Immunol.*, 23:901-944 (2005).
Tindall, et al., "The Rationale for Inhibiting 5☐-Reductase Isoenzymes in the Prevention and Treatment of Prostate Cancer", *The Journal of Urology*, 179(4):1235-1242 (2008).
Trindade, et al., "Nanocrystalline Semiconductors: Synthesis, Properties, and Perspectives", *Chem. Mat.*, 13(11):3843-3858 (2001).
Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192(2002).
Uhrich, et al., "Polymeric Systems for Controlled Drug Release", *Chem. Rev.*, 99(11):3181-3198 (1999).
Unkeless, et al., "Structure and function of human and murine receptors for IgG.", *Annu. Rev. Immunol.*, 6:251-281 (1998).
Uwatoku, et al., "Application of Nanoparticle Technology for the Prevention of Restenosis After Balloon Injury in Rats," *Circ. Res.*, 92(7): e62-9 (2003).
Valentini, et al., "Association of anthracycline derivatives with DNA: a fluorescence study.", *Farmaco [Sci]*, 40:377-390 (1985).
Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).
Vascotto, et al., "Antigen presentation by B lymphocytes: how receptor Signaling directs membrane trafficking.", *Curr., Opin., Immunol.*, 19(1):93-98 (2007).
Vihko, et al., "Radioimaging of Prostatic Carcinoma With Prostatic Acid Phosphatase—Specific Antibodies", *Biotechnology in Diagnostics*, 131-134 (1985).
Von Allmen, et al., "V domain of Rage interacts with AGEs on prostate carcinoma cells", *The Prostate*, 68(7):748-758 (2008).
Von Andrian and Mempel, "Homing and cellular traffic in lymph nodes.", *Nat. Rev. Immunol.*, 3(11):867-878 (2003).
Wang, et al., "A novel biodegradable gene carrier based on polyphosphoester.", *J. Am. Chem. Soc.*, 123(38):9480-9481 (2001).
Wang, et al., "Autoantibody signatures in prostate cancer.", *N Engl J Med*, 353(12):1224-1235 (2005).
Wang, et al., "Identification of prostate specific membrane antigen (PSMA) as the target of monoclonal antibody 107-1A4 by proteinchip; array, surface-enhanced laser desorptionlionization (SELDI) technology.", *Int. J. Cancer*, 92(6):871-876 (2001).
Wang, et al., "Interactions between an anthracycline antibiotic and DNA: molecular structure of daunomycin complexed to d(CpGpTpApCpG) at 1.2-A resolution.", *Biochemistry*, 26(4)1152-1163 (1987).
Weaver, et al., "Transferrin receptor ligand-targeted toxin conjugate (Tf-CRM107) for therapy of malignant gliomas.", *J. Neurooncol.*, 65(1):3-13 (2003).
Wessels, et al., "Studies of group B streptococcal infection in mice deficient in complement component C3 or C4 demonstrate an essential role for complement in both innate and acquired immunity.", *Proc. Natl. Acad. Sci.*, USA, 92(25):11490-11494 (1995).
Whelan, et al., "Efficient recovery of infectious vesicular stomatitis virus entirely from cDNA clones.", *Proc. Natl. Acad. Sci*, USA, 92(18):8388-8392 (1995).
Wilson, et al., "The Structure of an Antigenic Determinant in a Protein", *Cell*, 37:767-778 (1984).
Wind, et al., "An integrated confocal and magnetic resonance microscope for cellular research.", *J. Magn. Reson.*, 147(2):371-377 (2000).
Wlotzka, et al., "In vivo propeities of an anti-GnRH Spiegelmer: an example of an oligonucleotide-based therapeutic substance class," *Proc. Natl. Acad. Sci.* U. S. A., 99(13):8898-902 (2002).
Wright, et al., "Cyclophosphamidelgranulocyte colony-stimulating factor causes selective mobilization of bone marrow hematopoietic stem cells into the blood after M phase of the cell cycle.", *Blood*, 97(8):2278-2285 (2001).

Wu, "Arming antibodies: prospects and challenges for immunoconjugates.", *Nat. Biotechnol.*, 23(9):1137-1146 (2005).
Wu, et al., "Immunofluorescent labeling of cancer marker Her2 and other cellular targets with semiconductor quantum dots.", *Nat. Biotechnol.*, 21(1):41-46 (2003).
Yang, "Imaging of vascular gene therapy.", *Radiology*, 228:36-249 (2003).
Yoo, et al., "In vitro and in vivo anti-tumor activities of nanoparticles based on doxorubicin-PLGA conjugates.", *J. Control. Release*, 68(3):419-431 (2000).
Yuan, et al., "siRNA Selection Server: an automated siRNA oligonucleotide prediction server.", *Nucl. Acids. Res.*, 32:W130-W134 (2004).
Zamore, et al., "RNAi: double-stranded RNA directs the ATP-dependent cleavage of mRNA at 21 to 23 nucleotide intervals.", *Cell*, 101(1):25-33 (2000).
Zauner, et al., "Polylysine-basedtransfection systems utilizing receptor-mediated delivery.", *Adv. Drug Del. Rev.*, 30:97-113 (1998).
Zhang, et al., "The proliferative effect of estradiol on human prostate stromal cells is mediated through activation of ERK", *The Prostate*, 68(5):508-516 (2008).
Zheng, et al., "Highly fluorescent, water-soluble, size-tunable gold quantum dots.", *Phys. Rev. Lett.*, 93(7):077402 (2004).
Zhou, et al., "Investigation on a novel core-coated microspheres protein delivery system.", *J. Control. Release*, 75(1-21:27-36 (2001).
Zhou, et al., "Preparation of poly(L-serine ester): a structural analog of conventional poly(L-serine)", *Macromolecules*, 23(14):3399-3406 (1990).
Zuker, "Mfold web server for nucleic acid folding and hybridization prediction", *Nuc. Acid. Res.*, 31:3406-3415 (2003).
Cerchia, et al. "Neutralizing aptamers from whole-cell SELEX inhibit the RET receptor tyrosine kinase", PLoS Biology, 3(4):849-60 (2005).
Foss, et al., "Radiolabeled small-molecule ligands for prostate-specific membrane antigen: in vivo imaging in experimental models of prostate cancer", Clin. Cancer Res., 11:4022-28 (2005).
Govender, et al., "Defining the drug incorporation properties of PLA-PEG nanoparticles", Intl J of Pharmaceutics, 1999:95-110(2000).
Mitra, et al., "Tumour targeted delivery of encapsulated dextran-doxorubicin conjugate using chitosan nanoparticles as carrier", J Controlled Release, 74:317-23 (2001).
Wu, et al., Ng-circulation Poly(ethylene glycol)-poly(D,L-lactide) block copolymermicelles with modulated surace chane, J Contl Rel., 77:27-38 (2001).
Zhou, et al., "NAAG peptidase inhibitors and their potential for diagnosis and therapy", Nature Rev. Drug Disc., 4:1015-26 (2005).
Bies et al., "Lectin-mediated drug targeting: history and applications", *Advanced Drug Delivery Reviews*, 56:425-435 (2004).
Bocca, et al., "Phagocytic uptake of fluorescent slealth sad lipid nanoparticles", *Int. J. Pharmaceutics*, 175:185-193 (1998).
Brooking et al, "Transport of Nanoparticles Across the Rat Nasal Mucosa", *Journal of Drug Targeting*, 9(4):267-279 (2001).
Chandy et al., "Development of Poly(Lactic Acid)/Chitosan Co-Matrix Microspheres: Controlled Release of Taxol-Heparin for Preventing Restenosis", *Drug Delivery*, 8:77-86 (2001).
Chandy, et al., "5-Fluorouracil-loaded chitosan coated polylactic acid pmicrospheres as biodegradable drug carriers for cerebral tumors", *J. Microencapsulation*, 17(5):625-638 (2000).
Cheng, et al., "Formulation of functionalized PLGA-PEG nanoparticles for in vivo targeted drug delivery", *Biomaterrials*, 28:869-875 (2007).
Coppi, et al., "Chitosan-Alginate Microparticles as a Protein Carrier", *Drug Development and Industrial Pharmacy*, 27(5):393-400 (2001).
Elvassore, et al., "Production iof Insulin-Loaded Poly(Ethylene Glycol)/Poly/-actide) (PEG/PLA) Nanoparticles by Gas Antisolvent Techniques", *Journal of Pharmacrutical Sciences*, 90(10):1628-36 (2001).
Ermak and Giannasca, "Microparticle targeting to M cells", *Advanced Drug Delivery Reviews*, 34:261-283 (1998).
Fi Li Povic-Grcic at al., "Mucoadhesive chitosan-coated liposomes: characteristics and stability", *J. Microencapsulation*, 18 1:3-12 (2001).

(56) References Cited

OTHER PUBLICATIONS

Gaserod et al., "The enhancement of the bioadhesiva properties of calcium alginate gel beads by coating with chitosan", *Intl. J. of Pharmaceutics*, 175:237-246 (1998).

Hejazi et al ., "Stomach-specific anti-H. pylon therapy. I: preparation and characterization of tetracyline-loaded chitosan microshpheres", *Intl. J. of Pharmaceutics*, 235:87-94 (2002).

Huang et al., "Microencapsulation of Chlorpheniramine Maleate-Resin Particles with Crosslinked Chitosan for Sustained Release", *Pharmaceutical Development and Technology*, 4 1:107-115 (1999).

Janes et al., "Chitosan nanoparticles as delivery systems for doxorubicin", *Journal of Controlled Release*, 73:255-267 (2001).

Jayasena, "Aptamers: An Emerging Class of Molecules That Rival Antibodies in Diagnostics", *Clinical Chemistry*, 45(9):1628-1650 (1999).

Kawashima, et al., "Mucoadhesive DL-Lactide/Glycolide Copolymer Nanoshperes Coated with Chitosan to Improve Oral Delivery of Elcatonin", *Pharmaceutical Development and Technology*, 5(1):77-85 (2000).

Khandare, et al., "Polymer-drug conjugates: Progress in polymeric prodrugs," *Progress in Polymer Science*, 31(4): 359-397 (2006).

Kim, et al., "Target-specific cellular uptake of PLGA nanoparticles coated with poly(L-lysine)-poly(ethyleneglycol)-folate conjugate", *Langmuir*, 21(19): 8852-8857 (2005).

Lehr, "Lectin-mediated drug delivery: The second generation of bioadhesives", J. of Controlled Release, 65:19-29 (2000).

Lim et al., "Preparation and evaluation of the in vitro drug release properties and mucoadhesion of novel microspheres of hyaluronic acid and chitosan", *J. of Controlled Release*, 66:281-292 (2000).

Mi, et al., "Release of Indomethacin from a Novel Chitosan Microsphere Prepared by a Natrually Occurring Crosslinker: Examination of Crosslinking and Polycation-Anionic Drug Interaction", *J. of Applied Polymer Science*, 81:1700-1711 (2001).

Olivier, et al., "Drug Transport to Brain with Targeted Nanoparticles", *J. of the Am. Society of Experimental Neuro Therapeutics*, 2:108-119 (2005).

Pimentel, et al., "Peptide nanoparticles as novel immunogens: design and analysis of a prototypic severe acute respiratory syndrome vaccine", *Chemical Biology & Drug Design*, 73(1):53-61 (2009).

Ponchel, et al., "Specific and non-specific bioadhesive particulate systems for oral delivery to the gastrointestinal tract", *Advanced Drug Delivery Reviews*, 34:191-219 (1998).

Shimoda, et al., "Bioadhesive Characteristics of Chitosan Mircroshperes to the Mucosa of Rat Small Intestine", *Drug Delvelopment and Inustrial Pharmacy*, 27(6):567-576 (2001).

Simberg, et al., "Biomimetic amplification of nanoparticle homing to tumors", *Nat'l. Acad. Sic. USA*, 104(3):921-936 (2007).

Takeuchi, et al., "Enteral Absorption of Insulin in Rats from Mucoadhesive Chitosan-Coated Liposomes", *Pharmaceutical Research*, 13(6):896-801 (1996).

Takeuchi et al., "Mucoashesive Lipsomes Coated with Chitosan or Carbopol for Oral Administration of Peptide Drugs", *Proceed. Intl. Symp. Control. Rel. Bioact. Mater.*, 26:988-989 (1999).

Takeuchi, et al., "Spray-Dried Lactose Composite Particles Containing an Ion Complex of Alginate-Chitosan for Desinging a Dry-Coated Tablet Having a Time-Controlled Releasing Function", *Pharmaceutical Research*, 17 (1):94-99 (2000).

Tavitian, et al., "In vivo imaging with oligonucleotides for diagnosis and drug development", *Gut, 52 Su*, I IV :40-47 (2003).

Tobio, et al "Role of PEG on the stability in digestive fluids and in vivo fate of PEG-PLA nanoparticles following oral administration", *Colloids and Surfaces B: Biointerferences*, 18:315-323 (2000).

Vila, et al., "Design of biodegradable particles for protein delivery", *Journal of Controlled Release*, 78:15-24 (2002).

Vila, et al., "PLA-PEG Nanospheres: New Carriers for Transmucosal Delivery of Proteins and Plasmid DNA", *Poly. Adv. Technol.*, 13:851-858 (2002).

Yamada, et al., "In Vitro and in Vivo Evaluation of Sustained Release Chitosan-Coat Ketoprofen Microparticles", *Yakugaku Zasshi*, 121(3):239-245 (2001).

Yourong, et al, "Preparation of DHAQ-loaded mPEG-PLGA-mPEG nanoparticles and evaluation of drug release behaviors in vitrofin vivo," *J. Mat. Sci.: Mat. Med.*, 17(6): 509-16 (2006).

Yuan, et al, "Intranasal immunization with chitosan/pCETP nanoparticles inhibits atherosclerosis in a rabbit model of atherosclerosis", *Vaccine, Bitterworth Scientific*, 25:29-30 (2008).

Heald, et al., "Poly(lactic acid)-poly(ethylene oxide) (PLA-PEG) nanoparticles: NMR studies of he central solidlike PLA core and the liquid PEG corona", *Langmuir*, 18:3669-3675 (2002).

Tomai, et al., "Resiquimod and other immune response modifiers as vaccine adjuvants", *Expert Rev Vaccines*, 6:835-847 (2007) Abstract Only.

Villa, et al., "PLA-PEG particles as nasal protein carriers: the influence of the particle size", *Int. J Pharmaceut.*, 292:43-52 (2005).

Sarkar, et al., "Ligand-DNA interaction in a narrocage of reverse micelle", *Biopolymer.*, 83(6):675-86 (2006).

International Search Report mailed May 2, 2008.

Adams, et al., Amphiphilic block copolymers for drug delivery, J. Pharm. Sci., 92 (7):1343-55 (2003).

Balenga, et al., "Protective efficiency of dendrosomes as novel nano-sized adjuvants for DNA vaccination against birch pollen allergy", J Biotech., 123 (3):602-14 (2006).

Barinka, et al., "Interactions between human glutamate carboxypeptidase II and urea-based inhibitors: Structural characterization" , J Med. Chem.,51:7737-43 (2008).

Barinka, et al., "Structural insight into the pharmacophore pocket of human glutamate carboxypoeptidase II" , J. Med Chem., 50:3267-73 (2007).

Beck, et al., "A New Long-acting Injectable Microcapsule System for the Administration of Progesterone," Fertil. & Steril., 31(5):545-55 (1979).

Benita, et al., "Characterization of Drug-Loaded Poly(d,/-lactide) Microspheres," J. Pharm. Sci. 73(12):1721-24 (1984).

Caliceti, et al. "Effective protein release from PEG/PLA nano-particles produced by compressed gas anti-solvent precipitation techniques" , J of Cont. Release, 94:195-205 (2004).

Ch'ng, et al., "Bioadhesive Polymers as Platforms for Oral Controlled Drug Delivery II: Synthesis and Evaluation of Some Swelling, Water-Insoluble Bioadhesive Polymers," J. Pharm. Sci. 74: 399-405 (1988).

Chandran, et al, "Characterization of a targeted nanoparticle functionalized with a Urea-based inhibitor of prostate-specific membrane antigen (PSMA)" , Cancer Biol & Therapy, 7 (4):1-9 (2008).

Chandy, et al., "5-Fluorouracil-loaded chitosan coated polylactic acid pmicrospheres as biodegradable drug carriers for cerebral tumors" , J. Microencapsulation, 17(5):625-638 (2000).

Chen, et al., "Radiohalogenated prostate-specific membrane antigen (PSMA)- based ureas as imaging agents for prostate cancer" , *J Med Chem.*, 51 (24):7933-43 (2008).

Chickering & Mathiowitz, "Bioadhesive microspheres: i. A novel electrobalance-based method to study adhesive interactions between individual microspheres and intestinal mucosa," J. Control. Release 34:251-62 (1995).

Dancey, et al., "Therapeutic Targets:MTOR an related pathways" , Cancer Biol. Ther., 5(9):1065-73 (2006).

Duchene, et al., "Pharmaceutical and Medical Aspects of Bioadhesive Systems for Drug Administration," Drug Development &. Ind. Pharm. 14(2&3):283-31 (1988).

Ewesuedo and Ratain, "Systemically administered drugs" , Drug Delivery Systems in Cancer, Humana Press, Chapter 1:3-14 (2004).

Farokhzad, et al., "Cancer nanotechnology: drug encapsulated nanoparticle-aptmer bioconjugates for targeted delivery to prostate cancer cells", 13th Eu. Cancer Conf., Oct. 30-Nov. 3, Paris France (2005).

Gu, et al., "Precise engineering of targeted nanoparticles by using self-assembled biointegrated block copolymers" , PNAS, 105(7):2586-91 (2008).

Gurney, et al., "Bioadhesive intraoral release systems: design, testing and analysis," Biomaterials 5:336-40 (1984).

Hamdy, et al., "Co-delivery of cancer-associated antigen and toll-like receptor 4 ligand in PLGA nanoparticles induces potent CD8+ T cell-mediated anti-tumor immunity", Vaccine, 26(39):5046-57 (2008).

(56) References Cited

OTHER PUBLICATIONS

Hong, et al., "Enhanced and prolonged cross-presentation following endosomal escape of exogenous antigens encapdulated in biodegradable nanoparticles", Immunol., 117(1):78-88 (2006).
Hotter, et al., "Targeting of a B7-1 (CD80) immunoglobulin G fusion protein to acute myeloid leukemia blasts increases their costimulatory activity for autologous remission T cells.", Blood, 97(10):3138-3145 (2001).
Humblet, et al, "An HPLC/mass spectrometry platform for the development of multimodality contrast agents and targeted therapeutics: prostate-specific membrane antigen small derivatives", Contrast Med. Mol. Imaging, 1:196-211 (2006).
Humblet, et al. "High-affinity near-infrared fluorescent small-molecule contras agents for in vivo imaging of prostate-specific membrane antigen", Molecular Imaging, 4:448-62 (2005).
Igaku, "Intracellular trafficking of lipid antigens and their immune recognition by the CD1 system", Exp. Med., 24(7):936-40 (2006).
Illum, "Bioadhesive Microspheres as Potential Nasal Drug Delivery System," Int'l J. Pharm. 39: 189-99 (1987).
Jiang, et al., "Preparation of PLA and PLGA nanoparticles y binary organic solvent diffusion method", J. Cent. South Univ Technol, 10(3):202-06 (2003).
Kozikowski, et al. "Design of remarkably simple, yet potent urea-based inhibitors of glutamate carboxypeptidase II (NAALADase)", J. Med Chem, 44:298-301 (2001).
Labat-Robert & Decaens, "Glycoproteines du mucus gastrique: structure, fonctions et pathologie," Pathologie Biologie 24:241 (Paris 1979).
Lee, et al. "Adaptations of Nanoscale Viruses and Other Protein Cages for Medical Applications" Nanomedicine-Nanotechnology Biology and Medicine. 2(3):137-149 (2006).
Lehr, et al., "In vitro evaluation of mucoadhesive properties of chitosan and some other natural polymers," International J. Pharmaceutics 78: 43-48 (1992).
Lehr, et al., "Intestinal transit of bioadhesive microspheres in an in situ loop in the rat—a comparative study with copolymers and blends based on poly(acrylic acid)," J. Controlled Rel. 13:51-62 (1990).
Leon-Bay, et al., "Microsphere formation and drug delivery in a series of derivatized amino acids," Winter conference of Medicinal Chemistry (Steamboat Springs, Colarodo 1995).
Maresca, et al., "A series of halogenated heterodimeric inhibitors of prostate specific membrane antigen (PSMA) as radiolabeled probes for targeting prostate cancer", J. Med Chem., 52(2):347-57 (2009).
Martinez-Pomares, et al., "Fc chimeric protein containing the cysteine-rich domain of the murine mannose receptor binds to macrophages from splenic marginal zone and lymph node subcapsular sinus and to germinal centers", J Experimental Med., 184(5):1927-37 (1996).
Mathiowitz, et al., "Morphology of polyanhydride microsphere delivery systems," Scanning Microscopy 4(2):329-340 (1990).
Mease, et al., "N-[N-[(S)-1,3-Dicarboxypropyl]carbamoyl]-4-[18F]fluorobenzyl-L-cysteine, [18F]DCFBC: a new imaging probe for prostate cancer", Clin. Cancer Res., 14(10):3036-43 (2008).
Mikos, et al., "Interaction of Polymer Microspheres with Mucin Gels as a Means of Characterizing Polymer Retention on Mucus," J. Colloid & Interface Sci. 143(2):366-73 (1991).
Misra, et al., "Production of multimeric prostrate-specific membrane antigen small-molecule radiotracers using a solid-phase 99mTc preloading strategy", J Nuclear Medicine, 48(8):1379-89 (2007).
Pomper, et al., "New developments in molecular imaging of prostate cancer", Topical Symposium on Advanced Molecular Imaging Techniques in the detection, diagnosis, therapy and follow-up of Cancer, Palazzo Barberini, Rome Dec. 6, 2005.
Pulkkinen, et al., "Three-step tumor of paclitaxel using biotinylated PLA-PEG nanoparticies and avidin-biotin technology: Formulation developing and in vitro anticancer activity", Eur. J Pharm. Biopharm., 70:66-74 (2008).
Raghuvanshi, et al., "Improved immune response from biodegradable polymer particles entrapping tetanus toxiod by use of different immunization protocol and adjuvants", Int J Pharm., 245(1-2):109-21 (2002).
Sapra, et al., "Ligan-targeted liposomal anticancer drugs", Pergamon, Progress in Lipid Research, 42:439-462 (2003).
Scawen, et al., "The Action of Proteolytic Enzymes on the Glycoprotein from Pig Gastric Mucus," Biochemical J. 163:363-68 (1977).
Smart, et al., "An in vitro investigation of mucosa-adhesive materials for use in controlled drug delivery," J. Pharm. & Pharmacol. 36:295-99 (1984).
Spiro, "Glycoproteins," Annual Review of Biochemistry 39:599-638 (Snell, ed. 1970).
Surgery Frontier, "What's new in surgery frontier", 13(3):290-3 (2006).
Sweetman, "Entry for Docetaxel", Martindale:the complete drug reference, 33rd ed., p. 534 (2002).
Tobio, et al.,"Stealth PLA-PEG nanoparticlea as protein carriera for nasal administration", Pharm. Res., 15(2):270-75 (1998).
Walter, et al., "Hydrophillic poly (DL-lactide-co-glycolide) microspheres for the delivery of DNA to human-derived macrophages and dendritic cells", J Control Release, 76(1-2):149-68 (2001).
Yamamoto, et al., "Long-circulation Poly(ethylene glycol)-poly(D,L-lactide) block copolymermicelles with modulated surace chane", J Conti Rel., 77:27-38 (2001).
Yang, et al., "Micelles formed by self-assmbling of polylactide(ethylene glycol) block copolymers in aqueous solutions", J Colloid Interfac Si., 314:470-77 (2007).
Akagi, et al., "Development of vaccine adjuvants using polymeric nanoparticles and their potential applications for anti-HIV vaccine", Yakugaku Zasshi, 127(2):307-17 (2007) English Abstract.
Akagi, et al., "Multifunctional conjugation of proteins on/into bio-nanoparticles prepared by amphiphilic poly(gamma-glutamic acid)", J Biomat Sci Polym Ed., 17 (8):875-92 (2006).
Argov-Argaman, et al., "Lactosomes: Structural and compositional classification of unique nanometer-sized protein lipid particles of human milk", J Agric Food Chem., 58:11234-42 (2010).
Avgoustakis, "Pegylated poly(lactide) and poly(lactide-co-glycolide) nanoparticles: preparation, properties and possible applications in drug delivery" Curr Drug Deliv., 1:321-33 (2004).
Chu, et al, "Aptamer:toxin conjugates that specifically target prostate tumor cells", Cancer Res., 66:5989-92 (2006).
Elamanchili, et al., "Pathogen-mimicking" nanoparticles for vaccine delivery to dendritic cells, J Cont. Rel., 30(4):378-95 (2007).
Gorelik, et al., "Scanning surface confocal microscopy for simultaneous topographical and fluorescence imaging: application to single virus-like particle entry into a cell", PNAS, 99(25):16018-23 (2002).
Hallahanm, et al., "Integrin-mediated targeting of drug delivery to irradiated tumor blood vessels", Cancer Cell, 3:63-74 (2003).
Harris, et al., "Proteolytic actuation o nanoparticle self-assembly", Angewandte Chemie, 118:3233-7 (2006).
Hennenfent, et al., "Novel formulations of taxanes: a review. Old wine in a new bottle", Ann Oncol., 17:735-49 (2005).
Jayaprakash, et al., "Design and synthesis of a PSMA inhibitor-doxorubicin conjugate for targeted prostate cancer therapy", Chem Med Chem., 1:299-302 (2006).
Kawamura, et al., "Dendritic cells that endocytosed antigen-containing IgG-liposomes elicit effective antitumor immunity", J Immunother., 29(2):165-74 (2006).
Koenig, et al., "Immunologic factors in human milk: the effects of gestational age and pasteurization", J Human Lactation, 21:439-43 (2002).
Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).
Martin, et al., "Crystal structure at 2.8 A of an FcRn/heterodimeric Fc complex: mechanism of pH-dependent binding.", Mol Cell, 7:867-77 (2001).
Matsuo, et al., "Efficient generation of antigen-specific cellular immunity by vaccination with poly (gamma-glutamic acid)

(56) References Cited

OTHER PUBLICATIONS nanoparticles entrapping endoplasmic reticulum-targeted peptides", Biochem Biophys Res Commun 362:1069-72 (2007).
McNeil, "Nanotechnology for the biologist", J Leukoc Biol., 78:575-94 (2005).
Moon, et al., "Engineering Nano- and microparticles to tune immunity", Adv Mater., DOI:10.1002/adma.201200446 (2012).
Oyewumi, et al., "Comparison of cell uptake, biodistribution and tumor retention of folate-coated and PEG-coated gadolinium nanoparticles in tumor-bearing mice", J Control Rel., 93:613-26 (2004).
Oyewumi, et al., "Nano-microparticles as immune adjuvants: correlating particle sizes and the resultant immune responses", Exp Rev Vaccines, 9(9):1095-1107 (2010).
Riley, et al., "Physicochemical evaluation of nanoparticles assembled from Poly(lactic acid)-Poly(ethylene glycol) (PLA_PEG) block copolymers as drug delivery vehicles", Langmuir, 17:3168-74 (2001).
Riley, et al., "Colloidal stability and drug incorporation aspects of micellar-like PLA-PEG nanoparticles", Colloids Surfaces B Biointerfaces, 16:147-59 (1999).
Shields, et al., "High resolution mapping of the binding site on human IgG1 for Fc gamma Rl, Fc gamma Rll, Fc gamma Rlll, and FcRn and design of IgG1 variants with improved binding to the Fc gamma R", J Biolo Chem., 276(9):6591-6604 (2001).
Shim, "One target different effects: a comparison of distinct therapeutic antibodies against the same targets", Exp Mole Med.,43(10):539-49 (2011).
Suzuki, et al., "Development of effective antigen delivery carrier to dendritic cells via Fc receptor in cancer immunotherapy",Yakugaku Zasshi, 127(2):301-6 2007). English Abstract.
Taylor, et al., "Development of a specific system for targeting protein to metallophilic macrophages", PNAS, 101(7):1963-8 (2004).
Uto, et al., "Targeting of antigen to dendritic cells with poly(gamma-glutamic acid) nanoparticles induces antigen-specific humoral and cellular immunity", J Immunology, 178 (5):2979-86 (2007).
Wakita, et al "An indispensable role of type-1 IFNs for inducing CTL-mediated complete eradication of established tumor tissue by CpG-liposome co-encapsulated with model tumor antigen", Int. Immunol., 18(3):425-34 (2006).
Yu, et al., "Engineered bio-nanocapsules, the selective vector for drug delivery system", IUBMB Like, 58(1):1-6 (2006).
Akagi, et al., "Preparation and characterization of biodegradable nanoparticles based on poly0gamma-glutamic acid) with L-Phenylalanine as a protein carrier", J Control Release, 108:226-36 (2005).
Akagi, et al., "Protein direct delivery to dendritic cells using nanoparticles based on amphiphilic poly(amino acid) derivatives", Biomaterials, 28:3427-36 (2007).
Akerman, et al., "Nanocrystal targeting in vivo", PNAS, 99(20):12617-21 (2002).
Anderson, et al., "Biodegradation and biocompatibility of PLA and PLGA microspheres", Adv Drug Delivery, 28:5-24 (1997).
Bilati, et al., "Development of a nanoprecipitation method intended for the entrapment of hydrophilic drugs into nanoparticles", Eu J Pharma Sci., 24 (1):67-75 (2005).
CAS Reg. No. 1069-79-0, 4 pages, Entered STN: Nov. 16, 1984.
Chen, et al., "Beta-arrestin 2 mediates endocytosis of type II TGF-beta receptor and down-regulation of its signaling", Science, 301:1394-7 (2003).
Deng, et al., Optimization of preparative conditions for poly-DL-lactidepolyetyhlene glycol microspheres with entrapped Vibrino Cholera antigens, J Control Release, 58(2):123-31 (1999).
Diwan, et al., "Biodegradable nanoparticle mediated antigen delivery to human cord blood derived dendritic cells for induction of primary T cell responses", J Drug Targeting, 11 (8-10):495-507 (2003).
Drug Delivery Systems, 22(3):289 (2007).
Fahmy, et al., "Targeted for drug delivery", Nano Today, 18-26 (2005).
Farokhzad, "Nanotechnology for drug delivery: the perfect partnership", Exp Opin Drug Deliv., 5(9):927-9 (2008).
Henrickson, et al., "T cell sensing of antigen dose governs interactive behavior wit dendritic cells and sets a threshold for T cell activation", Nat Immunol., 9 (3):282-91 (2008).
Journal of Pediatric Practice, 64(9):1389-94 (2001).
Life Technologies, retrieved from the internet http://www.lifetechnologles.com/us/en/home/references/protocols/nucleic-acid-purification-and-analysis/ma-protocal/agarose-gel-electrophoresis-of-ma.html, retrieved May 30, 2014.
Morein, et al., "Current status and potential application of ISCOMs in veterinary medicine", Adv Drug Deliv Rev., 56:1367-82 (2004).
Nobs, et al., "Surface modification of poly(lactic acid) nanoparticles by covalent attachment of thiol groups by means of three methods", Intl J Pharma., 250:327-37 (2003).
Ohuchi, et al., "Selection of RNA aptamers against recombinant transforming growth factor-$^2$ type III receptor displayed on cell surface", Biochimie, 88:897-904 (2006).
Olszewski, et al., "NAAG peptidase inhibition reduces locomotor activity and some stereotypes in the PCP model of schizophrenia via group II mGluR", J Neurochem., 89:876-85 (2004).
Ponchel, et al., "Mucoadhesion of colloidal particulate systems in the gastro-intestinal tract", Eu J Pharma Biopharma., 44:25-31 (1997).
Raghavan, et al., "Fc receptors and their interactions with immunoglobulins", Annu Rev Cell Dev.,12:181-220 (1996) Abstract Only.
Ravetch and Bolland, "IgG Fc Receptors", Ann Rev Immunol., 19:275-90 (2001).
Schiffelers, et al., "Cancer siRNA theraphy by tumor selective delivery with ligand-targeted sterically stabilized nanoparticle", Nucleic Acids Res., 32(19):1-10 (2004).
Scholfield, "Composition of soybean lecithin", J Am Oil Sci Soc., 58 (10):889-92 (1981).
Shadidi and Sioud, "Selection of peptides for specific delivery of oligonucleotides into cancer cells", Methods Molecular Biol., 252:569-80 (2004).
Singh, et al., "Nanoparticles and microparticles as vaccine-delivery systems", Expert Rev. Vaccines, 6(5):797-808 (2007).
Tamura, et al., "Regulation of Th2 responses by CpG motifs", Respiration, 121 (12):1147-55 (2002).
Truong-Le, et al., "Gene transfer by DNA-Gelation nanospheres", Biochem and Biophy., 381:47-55 (1999).
Van de Winkel, et al., "Human Igl Fc receptor heterogeneity: molecular aspects and clinical implications", Immunology Today, 14(5):215-21 (1993).
Wakita, et a.., "Mechanisms for complete eradication of large tumor mass by liposome-CpG nanoparticle tumor vaccine", Clinical Immunology, 45(5):483-90 (2006).
Wei, et al., "Preparation of uniform-sized PELA microspheres with high encapsulation efficiency of antigens by premix membrane emulsification", J Colliod Interface Sci., 323 (2):267-73 (2008).
Wu, et al.,"Selection of oligonucleotide apatamers with enhanced uptake and activation of human leukemia B cell", Human Gene, 14:849-60 (2003).
Yamamoto, et al., "Antinociceptive effects of N-acetylaspartylglutamate (NAAG) peptidase inhibitors ZJ-11, ZJ-17 and ZJ-43 in the rat formalin test and in the rat neuropathic pain model", Eur J Neurosci., 20(2):453-94 (2004).
Yoo and Park, "Folate receptor targeted biodegradable polymeric doxorubicin micelles", J Cont. Rel., 96:273-83 (2004).
Zhou, et al., "Poly-D,L-lactide-co-poly(ethylene glycol) microspheres as potential vaccine delivery systems", J Control Release, 86:195-205 (2003).

\* cited by examiner

MICROFLUIDIC SYNTHESIS OF ORGANIC NANOPARTICLES

CROSS-REFERENCE TO RELATED APPLICATIONS

The present application is a U.S. national phase application under 35 U.S.C. 371 of international PCT application number PCT/US2007/071901, filed Jun. 22, 2007, which claims priority under 35 U.S.C. §119(e) to U.S. provisional patent applications, U.S. Ser. No. 60/805,656, filed Jun. 23, 2006 ("the '656 application"), and U.S. Ser. No. 60/916,998, filed May 9, 2007 ("the '998 application"); each of which is incorporated herein by reference.

GOVERNMENT SUPPORT

The United States Government has provided grant support utilized in the development of the present invention. In particular, the National Institutes of Health/National Cancer Institute (CA119349; SP50CA90381) and National Institutes of Health/National Institute of Biomedical Imaging and BioEngineering (EB003647) have supported development of this invention. The United States Government may have certain rights in the invention.

BACKGROUND OF THE INVENTION

Particulate drug delivery systems have been developed for delivering drugs to a subject, and such particles can be modified to target particular organs, tissues, cells, or intracellular compartments; to increase circulation time before clearance by the liver or kidney; and/or to sequester toxic drugs during transport and to release them only upon delivery to a targeted site. In order to effectively perform all of these tasks, particle characteristics (e.g. composition, size, charge, etc.) must be precisely controlled. However, current methods for manufacturing particles for drug delivery do not allow for controlled synthesis of particles with engineered properties. Nor do existing methods of manufacturing particles provide allow for rapid production and screening of particle libraries or economically feasible production of particles. For effective drug therapy, it is desirable to deliver sustained and controlled amounts of drugs to target tissues and to reduce delivery to non-target tissues in order to minimize side effects. Parameters such as particle composition, size, charge, targeting moieties, drug encapsulation, etc. can affect the biodistribution and pharmacokinetics of the drug to be delivered. It is therefore desirable to control the properties of polymeric particles so they are optimized for the most effective delivery of a drug.

Therefore, a strong need in the art remains for systems and methods that provide controlled synthesis of particles with engineered properties, such as a particular composition, size, targeting moiety, agent to be delivered, and/or charge. There is a need in the art for systems that provide for rapid screening of particle libraries and economically feasible production of particles for drug delivery.

SUMMARY OF THE INVENTION

The present invention provides microfluidic systems for producing polymeric drug delivery particles by nanoprecipitation using controlled mixing of polymeric solutions in a fluid that is not a solvent for the polymer (i.e. a non-solvent such as water). The mixing can be achieved by any techniques or mixing apparatus known in the art of microfluidics, including, but not limited to, hydrodynamic flow focusing.

The present invention provides microfluidic devices for producing polymeric drug delivery particles. In general, a microfluidic device comprises at least two channels that converge into a mixing apparatus. In some embodiments, the channels join together at an angle ranging between zero degrees and 180 degrees. A stream of fluid is capable of flowing through each channel, and the streams join and flow into the mixing apparatus. In general, at least one stream comprises a polymeric solution, and at least one stream comprises a non-solvent. In some embodiments, the flow of the streams is laminar.

In some embodiments, the channels have a circular cross-section. In some embodiments, the channels that converge into the mixing apparatus are of uniform shape. In some embodiments, the width or height of each channel ranges from approximately 1 µm to approximately 1000 µm. In some embodiments, the length of each channel ranges from approximately 100 µm to approximately 10 cm.

Channels may be composed of any material suitable for the flow of fluid through the channels. Typically, the material is one that is resistant to solvents and non-solvents that are used in the preparation of particles. In general, the material is not one that will dissolve or react with the solvent or non-solvent. In some embodiments, channels are composed of glass, silicon, metal, metal alloys, polymers, plastics, photocurable epoxy, ceramics, or combinations thereof.

In some embodiments, channels are formed by lithography, etching, embossing, or molding of a polymeric surface. In general, the fabrication process may involve one or more of any of the processes described herein, and different parts of a device may be fabricated using different methods and assembled or bonded together.

Typically, a source of fluid is attached to each channel, and the application of pressure to the source causes the flow of the fluid in the channel. The pressure may be applied by a syringe, a pump, and/or gravity. In some embodiments, the applied pressure is regulatable (i.e. the applied pressure may be increased, decreased, or held constant). In some embodiments, the flow rate is regulatable by adjusting the applied pressure. In some embodiments, the flow rate is regulatable by adjusting the size (e.g. length, width, and/or height) of the channel. In some embodiments, the flow rate may range from 0.001 µl/min to 1.0 ml/min. In specific embodiments, the flow rate is approximately 10 µl/min for non-solvent solutions (e.g. an aqueous solution such as water). In specific embodiments, the flow rate is approximately 0.5 µl/min for polymeric solutions.

The present invention provides microfluidic systems in which a plurality of inlet streams of solutions with polymer, targeting moieties, lipids, drug, payload, etc. converge and mix, and the resulting mixture yields a stream which joins a stream of non-solvent and flows into the mixing apparatus. In some embodiments, a microfluidic system may comprise at least 2, at least 3, at least 4, at least 5, at least 6, at least 7, at least 8, at least 9, at least 10, or more inlet streams. The flow of each inlet stream is regulated by a source of fluid, wherein the application of pressure to the source causes the flow of fluid in the inlet stream.

In some embodiments, the same amount of pressure is applied to all of the channels and/or inlet streams. In some embodiments, different amounts of pressure are applied to different channels and/or inlet streams. Thus, in some embodiments, the flow rate may be the same through all channels and/or inlet streams, or the flow rate may be different in different channels and/or inlet streams.

In some embodiments, inventive microfluidic systems produce particles at a rate ranging from approximately 0.1 mg/min to approximately 1 g/min. Purification steps are optionally performed after synthesis of particles. The present invention provides methods for integrating microfluidic purification processes in line with nanoprecipitation. Using integrated filtration processes, inventive microfluidic device can enable synthesis of ready-to-use nanoparticles with minimal labor and time consumption.

The present invention provides microfluidic systems for producing polymeric particles comprising multiple channels that converge and flow into a mixing apparatus. Streams of fluid flow through each channel, and the streams join and flow into the mixing apparatus. In general, a polymeric solution comprising a polymer and a solvent flows through at least one channel, and a non-solvent flows through at least one channel. As used herein, the term "solvent" refers to a substance in which a polymer is more soluble than a "non-solvent."

Typically, in accordance with the present invention, the solvent comprises at least one organic solvent, and the non-solvent is an aqueous solution. In some embodiments, the solvent and/or the non-solvent may further comprise one or more surfactants; therapeutic agents (including drugs, diagnostic agents, and/or prophylactic agents); targeting moieties; or other components.

In some embodiments, the solvent is at least one of 1,4-dioxane, tetrahydrofuran (THF), diethylether, acetone, acetonitrile, dimethyl sulfoxide (DMSO), dimethylformamide (DMF), acids, and alcohols (e.g. methanol, ethanol, isopropanol, butanol, etc.). In some embodiments, the non-solvent comprises water.

Any polymer that is more soluble in the polymer stream than in the solution in which the polymer stream is mixed may be used in the microfluidic systems of the present invention. In some embodiments, the polymer is selected from the group consisting of polyalkylenes (e.g. polyethylenes), polycarbonates (e.g. poly(1,3-dioxan-2one)), polyanhydrides (e.g. poly(sebacic anhydride)), polyhydroxyacids (e.g. poly($\beta$-hydroxyalkanoate)), polyfumarates, polycaprolactones, polyamides (e.g. polycaprolactam), polyacetals, polyethers, polyesters (e.g. polylactide, polyglycolide), poly(orthoesters), polyvinyl alcohols, polyurethanes, polyphosphazenes, polyacrylates, polymethacrylates, polycyanoacrylates, polyureas, polystyrenes, and polyamines.

In some embodiments, the polymer is PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio.

In some embodiments, fluid streams may optionally comprise one or more therapeutic agents (including drugs, diagnostic agents, and/or prophylactic agents) to be associated with the surface of, encapsulated within, surrounded by, and/or dispersed throughout particles produced using inventive microfluidic systems. Exemplary therapeutic agents that may be used in accordance with the present invention include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof.

In some embodiments, fluid streams may optionally comprise one or more targeting moieties. A targeting moiety is any moiety that binds to a component associated with an organ, tissue, cell, extracellular matrix component, and/or intracellular compartment. Thus, inclusion of a targeting moiety in one or more of the fluid streams can result in production of particles which can be targeted to a particular organ, tissue, cell, extracellular matrix component, and/or intracellular compartment (i.e. a "target" or a "marker"). A targeting moiety may be a nucleic acid, polypeptide, glycoprotein, carbohydrate, lipid, etc.

In some embodiments, fluid streams may optionally comprise one or more surfactants. A surfactant may be mixed with a solvent, non-solvent, and/or other component of a particle. In some embodiments, fluid streams may optionally comprise buffering agents and/or salts.

In general, inventive microfluidic systems may be used to produce particles having a greatest dimension (e.g. diameter) of less than 100 microns ($\mu$m). In some embodiments, produced particles have a greatest dimension of less than 900 nm, 800 nm, 700 nm, 600 nm, 500 nm, 400 nm, 300 nm, 200 nm, or 100 nm. Typically, produced particles have a greatest dimension (e.g., diameter) of 300 nm or less. In some embodiments, produced particles have a greatest dimension ranging between 25 nm and 100 nm. In specific embodiments, produced particles have a greatest dimension ranging between 25 nm and 50 nm.

In some embodiments, the diameter of no more than 25% of the produced particles varies from the mean particle diameter by more than 150%. In some embodiments, the diameter of no more than 25% of the produced particles varies from the mean particle diameter by more than 100%. In some embodiments, the diameter of no more than 25% of the produced particles varies from the mean particle diameter by more than 75%. In certain embodiments, the diameter of no more than 25% of the produced particles varies from the mean particle diameter by more than 50% of the mean particle diameter. In some embodiments, the diameter of no more than 25% of the produced particles varies from the mean particle diameter by more than 25% of the mean particle diameter. In some embodiments, the diameter of no more than 20% of the produced particles varies from the mean particle diameter by more than 10% of the mean particle diameter. In some embodiments, the diameter of no more than 25% of the produced particles varies from the mean particle diameter by more than 5% of the mean particle diameter.

It is often desirable to produce a population of particles that is relatively uniform in terms of size, shape, and/or composition so that each particle has similar properties. For example, at least 80%, at least 90%, or at least 95% of the particles produced using inventive microfludic systems may have a diameter or greatest dimension that falls within 5%, 10%, or 20% of the average diameter or greatest dimension. In some embodiments, a population of particles may be heterogeneous with respect to size, shape, and/or composition.

Zeta potential is a measurement of surface potential of a particle. In some embodiments, produced particles have a zeta potential ranging between −300 mV and +300 mV. In some embodiments, produced particles have a zeta potential ranging between −100 mV and +100 mV. In some embodiments, produced particles have a substantially neutral zeta potential (i.e. approximately 0 mV). In some embodiments, produced particles have a negative zeta potential. In some embodiments, produced particles have a positive zeta potential.

In some embodiments, particles produced using inventive microfluidic systems are microparticles (e.g. microspheres). In general, a "microparticle" refers to any particle having a diameter of less than 1000 $\mu$m. In some embodiments, produced particles are nanoparticles (e.g. nanospheres). In general, a "nanoparticle" refers to any particle having a diameter of less than 1000 nm. In some embodiments, produced particles are picoparticles (e.g. picospheres). In general, a "picoparticle" refers to any particle having a diameter of less than 1 nm. In some embodiments, produced particles are liposomes. In some embodiments, produced particles are micelles.

Microfluidic systems provided by the present invention are useful for engineering particles that have specific characteristics (e.g. polymer composition, therapeutic agent composition, particle size, particle charge, etc.). By adjusting any parameter (e.g. flow rate, channel size, polymer selection and concentration, solvent and non-solvent selection concentration, therapeutic agent selection and concentration, surfactant, targeting moiety, mixing time, etc.), particles having specific or desirable characteristics can be engineered.

In some embodiments, the characteristics of the particles may be modified by adjusting the composition of at least one inlet stream. In some embodiments, the characteristics of the particles may be modified by adjusting the concentration of polymer in the polymeric solution. In some embodiments, the characteristics of the particles may be modified by adjusting the concentration of a therapeutic agent in the polymeric stream or in the non-solvent stream. In some embodiments, the characteristics of the particles may be modified by adjusting the concentration of a targeting moiety in the polymeric stream or in the non-solvent stream.

In some embodiments, the characteristics of the particles may be modified by adjusting the non-solvent to solvent ratio of the fluid in the mixing apparatus. In some embodiments, the non-solvent to solvent ratio of the fluid in the mixing apparatus can be controlled by adjusting the flow rates of the polymeric stream(s) and the non-solvent stream(s). In some embodiments, adjusting the mixing time of the streams results in modifying the composition of the polymeric stream.

The present invention provides large-scale combinatorial screening of particle production conditions. Two ways in which combinatorial synthesis may be achieved are serial and parallel combinatorial syntheses. The present invention provides particle libraries having a spectrum of characteristics that are synthesized by varying particle production parameters.

This application refers to various issued patents, published patent applications, journal articles, and other publications, all of which are incorporated herein by reference.

DEFINITIONS

Figure 1:
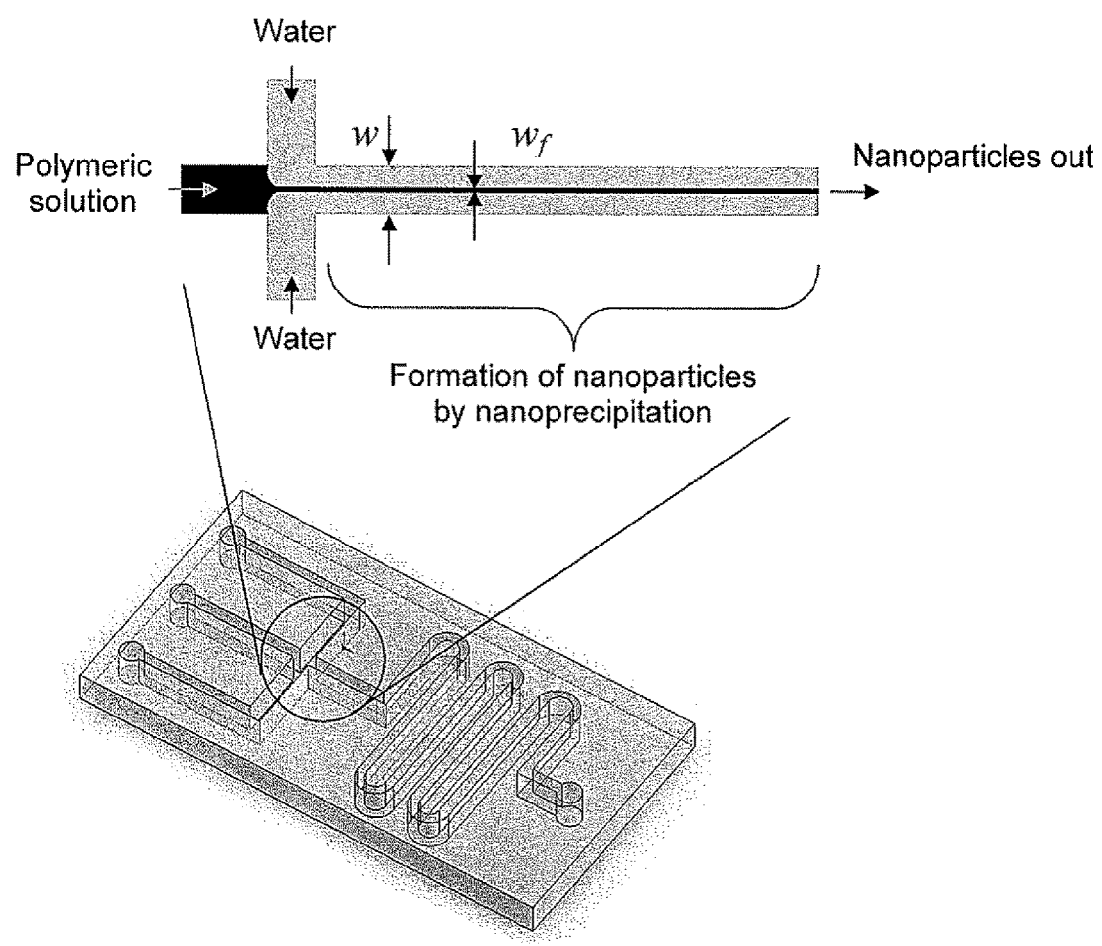
FIG. 1: Synthesis of nanoparticles by controlled nanoprecipitation using hydrodynamic flow focusing in microfluidic channels. Shown are two water streams that converge and flow into a central stream. One water stream was split into two in the fabricated devices.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Particle: As used herein, a "particle" refers to any entity having a diameter of less than 100 microns (μm). Typically, particles have a greatest dimension (e.g., diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. In some embodiments, a population of particles may be relatively uniform in terms of size, shape, charge, and/or composition. In general, inventive particles are biodegradable and/or biocompatible. Inventive particles can be solid or hollow and can comprise one or more layers. In some embodiments, particles are spheres, spheroids, flat, plate-shaped, cubes, cuboids, ovals, ellipses, cylinders, cones, or pyramids. In some embodiments, particles can comprise a matrix of one or more polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step. Inventive particles may be microparticles, nanoparticles, liposomes, and/or micelles. As used herein, the term "nanoparticle" refers to any particle having a diameter of less than 1000 nm. In certain embodiments, the particles are organic particles such as particles made from organic polymer, lipids, sugars, or other organic materials. Such organic particles may optionally contain some inorganic material; however, the amount of inorganic material is less than 50%, less than 25%, less than 10%, less than 5%, or less than 1%. In certain embodiments, the particles are polymeric particles with a substantial portion of the matrix of the particle being polymeric.

Peptide: As used herein, a "peptide" or "polypeptide" generally refers to a string of at least two amino acids linked to one another by peptide bonds. Peptides may include moieties other than amino acids (e.g. may be glycoproteins) and/or may be otherwise processed or modified. Those of ordinary skill in the art will appreciate that a "peptide" or "polypeptide" can be a complete polypeptide chain as produced by a cell or can be a functional portion thereof. In some embodiments, the term "protein" refers to a single polypeptide chain. In some embodiments, a protein may comprise more than one polypeptide chain, for example linked by one or more disulfide bonds or associated by other means.

Small molecule: In general, a "small molecule" is understood in the art to be an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

Subject: As used herein, the term "subject" or "patient" refers to any organism to which particles produced by a microfluidic system in accordance with this invention may be administered, e.g. for experimental, therapeutic, diagnostic, and/or prophylactic purposes. Typical subjects include animals (e.g., mammals such as mice, rats, rabbits, non-human primates, and humans) and/or plants.

Therapeutic agent: As used herein, the phrase "therapeutic agent" refers to any agent that, when administered to a subject, has a therapeutic, diagnostic, and/or prophylactic effect and/or elicits a desired biological and/or pharmacological effect. In some embodiments, a therapeutic agent is a drug. In certain embodiments, the therapeutic agent is a drug approved for human or veterinary use by the U.S. Food and Drug Administration or another foreign counterpart.

DETAILED DESCRIPTION OF CERTAIN
EMBODIMENTS OF THE INVENTION

Microfluidics

Microfluidics is the science and technology of manipulating flows in microscale channels, typically ranging from 10 μm-100 μm in size (Whitesides, 2006, *Nature*, 442:368). Microfluidics as a field of research emerged in the 1990s, pioneered by the idea of Manz et al. (1992, *J. Chromatography,* 593:253) that several time consuming, laborious steps in chemical and biological analysis could be efficiently carried out in miniaturized channels and chambers with faster throughput and time-to-result, smaller sample consumption, and lower cost. Since then, microfluidics has emerged as an active research area, with applications ranging from biological analysis to chemical synthesis, and electronic cooling to optics.

It is desirable to have control over particle synthesis to yield monodispersed particle formulations. Self-assembly of di-block copolymers has been shown to depend upon the rate of mixing, yielding smaller particles with more rapid mixing (Johnson and Prud'homme, 2003, *Phys. Rev. Lett.,* 91:118302). Microfluidics offers advantages that have made it a very useful tool for particle synthesis (deMello and deMello, 2004, *Lab on a Chip,* 4:11N)—(i) the ability to rapidly mix reagents and provide homogeneous reaction conditions, (ii) continuous variation of reaction parameters, and (iii) addition of reactants at precise time intervals. Microfluidics for synthesis of particles has not been previously performed. Until the present invention, the process of nanoprecipitation that is widely used for the synthesis of polymeric nanoparticles has not been tested on a microfluidics platform.

Nanoprecipitation

Nanoparticles are typically synthesized using four major processes (Astete and Sabliov, 2006, *J. Biomat. Sci.,-Polymer Ed.,* 17:247; Quintanar-Guerrero et al., 1998, *Drug Dev. Industrial Pharmacy,* 24:1113; Jones and Leroux, 1999, *Eur. J. Pharmaceutics Biopharmaceutics,* 48:101; Croy and Kwon, 2006, *Curr. Pharm. Design,* 12:4669; Allen et al., 1999, *Colloids Surfaces B-Biointerfaces,* 16:3; and Harada and Kataoka, 2006, *Progress Polymer Sci.,* 31:949)—nanoprecipitation (i.e. solvent displacement), emulsion evaporation, salting out, and emulsion evaporation.

The nanoprecipitation method (U.S. Pat. No. 5,118,528, incorporated herein by reference) is a single-step process for synthesis of nanoparticles by mixing a solution containing a substance into another solution (i.e. the non-solvent) in which the substance has poor solubility. For example, polymeric (e.g. PLGA-PEG) nanoparticles represent a major fraction of nanoparticles used for targeted drug delivery. These nanoparticles can be formed by nanoprecipitation methods (see, e.g., U.S. Pat. No. 5,118,528), in which polymer solutions in either water-immiscible or water-miscible solvents are added to an aqueous fluid (i.e. the non-solvent).

In nanoprecipitation, nanoparticles form as the water-miscible solvent diffuses into the aqueous phase and/or mixes with the aqueous phase, and the polymer solubility in the resulting solution decreases. Typically, nanoprecipitation is carried out by manually dropping a polymer/drug solution into water, and there is little control over mixing and precipitation. Johnson et al. have studied the assembly of particles of co-block polymers in microreactors and have found that the size of the resulting nanoparticles can be controlled by controlling the mixing time (Johnson and Prud'homme, 2003, *Phys. Rev. Lett.,* 91:118302).

Nanoprecipitation involves the mixing of solutions (i.e. solvents and non-solvents of the polymer), and the present invention encompasses the recognition that mixing can be easily done in a very rapid and controlled manner in microfluidic devices. The present invention encompasses the recognition that with millisecond or even microsecond mixing timescales, microfluidic synthesis of polymeric nanoparticles may yield better control over nanoparticle formation and properties. The present invention provides systems and methods for improving the homogeneity of compositions of nanoparticles and providing precise control over nanoparticle characteristics such as drug loading, composition, size, charge, and surface modifications.

Nanoprecipitation by Hydrodynamic Flow Focusing
in a Microfluidic Device

The present invention provides microfluidic systems for producing polymeric drug delivery particles by nanoprecipitation using controlled mixing of polymeric solutions in a fluid that is not a solvent for the polymer (i.e. a non-solvent such as water). The mixing can be achieved by any techniques or mixing apparatus known in the art of microfluidics. In certain embodiments, mixing is achieved by hydrodynamic flow focusing (Knight et al., 1998, *Phys. Rev. Lett.*, 80:3863) (FIG. 1). In this method, two or more streams, each in different microfluidic channels, join and flow into one microfluidic channel. The polymeric stream contains the polymeric solution, while the other stream(s) contain a fluid that is not a solvent for the polymer (i.e. the non-solvent). The compositions of these streams may vary, and may include surfactants or mixtures of solvents, as described herein. By controlling the flow rates of the streams either using pumps or applying pressure, the polymeric stream is focused into a narrow stream of width ($w_f$), which is smaller than the channel width (w). Diffusion of solvent and water result in rapid mixing and precipitation of the nanoparticles. For a given diffusivity (D) of water and solvents, the mixing time is approximately given by the diffusion time for the solvent and water.

$$t_{mix} \approx \frac{w_f^2}{D}$$

For example, for a typical diffusivity of $10^{-9}$ m$^2$/s and a focused width of 1 μm, the mixing time is 1 ms. This mixing time may be easily controlled by controlling the width of the polymeric stream. As the streams are continuously flowing, nanoparticles are continuously synthesized.

Apart from rapid mixing, flow in the device may also affect the polymer conformation (Pfohl et al., 2003, *Chemphyschem*, 4:1291) and hence affect nanoprecipitation. This effect may be controlled by controlling flow in the device, thereby controlling the process of nanoprecipitation and nanoparticle properties.

Other Methods of Nanoprecipitation in a Microfluidic Device

In certain embodiments, use of other microfluidic mixers that yield homogeneous polymer concentrations while mixing may result in yet more monodispersed populations of nanoparticles. Other types of mixers that may be used for nanoprecipitation include, but are not limited to, the chaotic advection mixers (e.g. herringbone mixer; see FIG. 2), zigzag mixers (see FIG. 2), droplet mixers (FIG. 3), shear superposition mixers (FIG. 3), T-mixers, mixers based on Tesla structures, active mixers, etc. (Nguyen and Wu, 2005, *J. Micromechan. Microeng.*, 15:R1). The configuration and number of streams being mixed may vary in each case. These mixers may be part of a larger network of microfluidic components, such as channels, mixers, reservoirs, pumps, etc.

Nanoparticle Synthesis Using a Chaotic Advection Mixer

Figure 2:
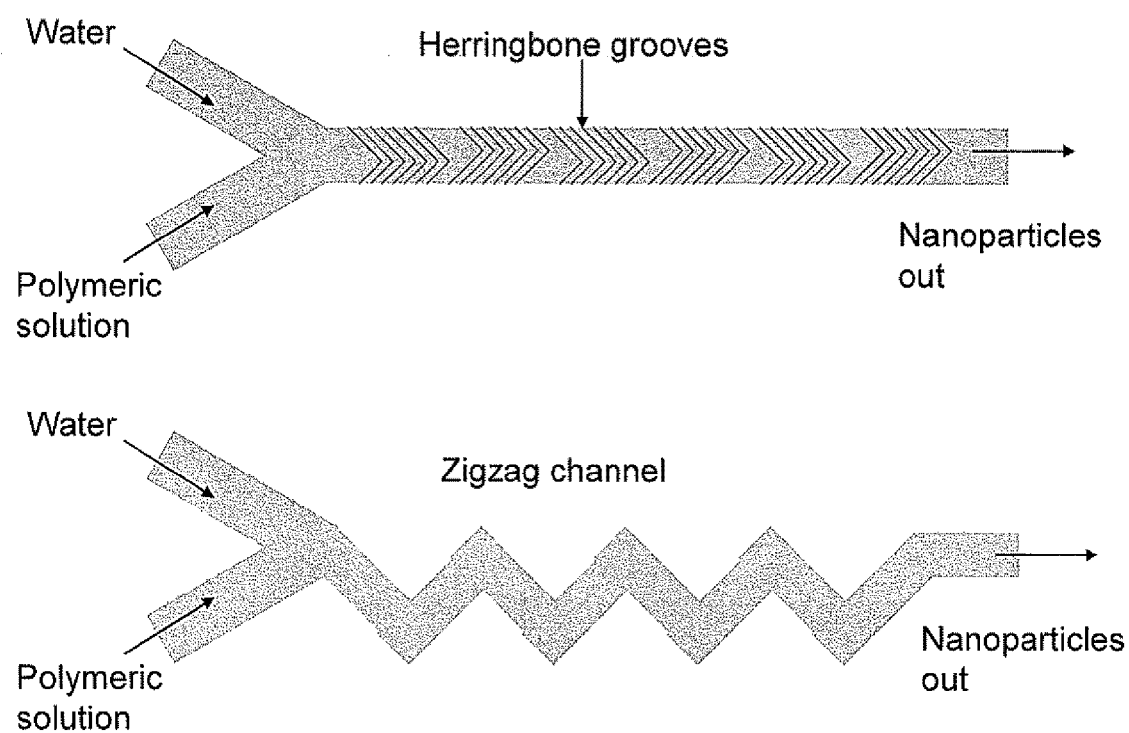
FIG. 2: Nanoparticle synthesis by nanoprecipitation using a staggered herringbone mixer (top) and using a zigzag channel mixer (bottom).

Aqueous and polymeric solutions may be mixed using a variety of chaotic passive advection mixers that can mix efficiently, even at low Reynolds numbers (<10). An example of this type of mixer is the staggered herringbone mixer developed by Stroock et al. (2002, *Science*, 295:647). Two streams (aqueous and polymeric) converge into the mixer as depicted in FIG. 2. The mixer consists of a channel with herringbone groove structures. Typical channel widths may range from 1 μm to 1 mm, and groove depth is typically a small fraction of the channel size (1% to 30%). In some embodiments, channel widths may be approximately 1 μm, approximately 5 μm, approximately 10 μm, approximately 50 μm, approximately 100 μm, approximately 250 μm, approximately 500 μm, approximately 750 μm, or approximately 1 mm. In some embodiments, groove depth is approximately 1%, approximately 5%, approximately 10%, approximately 15%, approximately 20%, approximately 25%, or approximately 30% of the channel size.

Nanoparticle Synthesis Using a Zigzag Mixer

Another method of mixing in microfluidics at higher Reynolds numbers (>70) is using a zigzag channel (Nguyen and Wu, 2005, *J. Micromechan. Microeng.*, 15:R1; see FIG. 2). Water and polymeric solutions converge into the channel, and mixing is induced at moderate to high Reynolds numbers due to channel geometry. In some embodiments, zigzag channel systems may comprise at least 1, at least 2, at least 3, at least 4, at least 5, at least 10, at least 20, at least 30, at least 40, at least 50, at least 60, at least 70, at least 80, at least 90, at least 100, or more zigzag segments. In some embodiments, the mean diameter of a zigzag channel is approximately 0.1 μm, approximately 1.0 μm, approximately 10 μm, approximately 100 μm, approximately 1.0 mm, or greater. In some embodiments, the length of each segment of the zigzag is approximately 1 times, approximately 2 times, approximately 3 times, approximately 4 times, approximately 5 times, approximately 6 times, approximately 7 times, approximately 8 times, approximately 9 times, approximately 10 times, or greater than 10 times the channel size. In some embodiments, an angle between segments of the zigzag may be approximately 10 degrees, approximately 20 degrees, approximately 30 degrees, approximately 40 degrees, approximately 50 degrees, approximately 60 degrees, approximately 70 degrees, approximately 80 degrees, approximately 90 degrees, approximately 100 degrees, approximately 110 degrees, approximately 120 degrees, approximately 130 degrees, approximately 140 degrees, approximately 150 degrees, approximately 160 degrees, or approximately 170 degrees.

Nanoparticle Synthesis Using a Droplet Mixer

Figure 3:
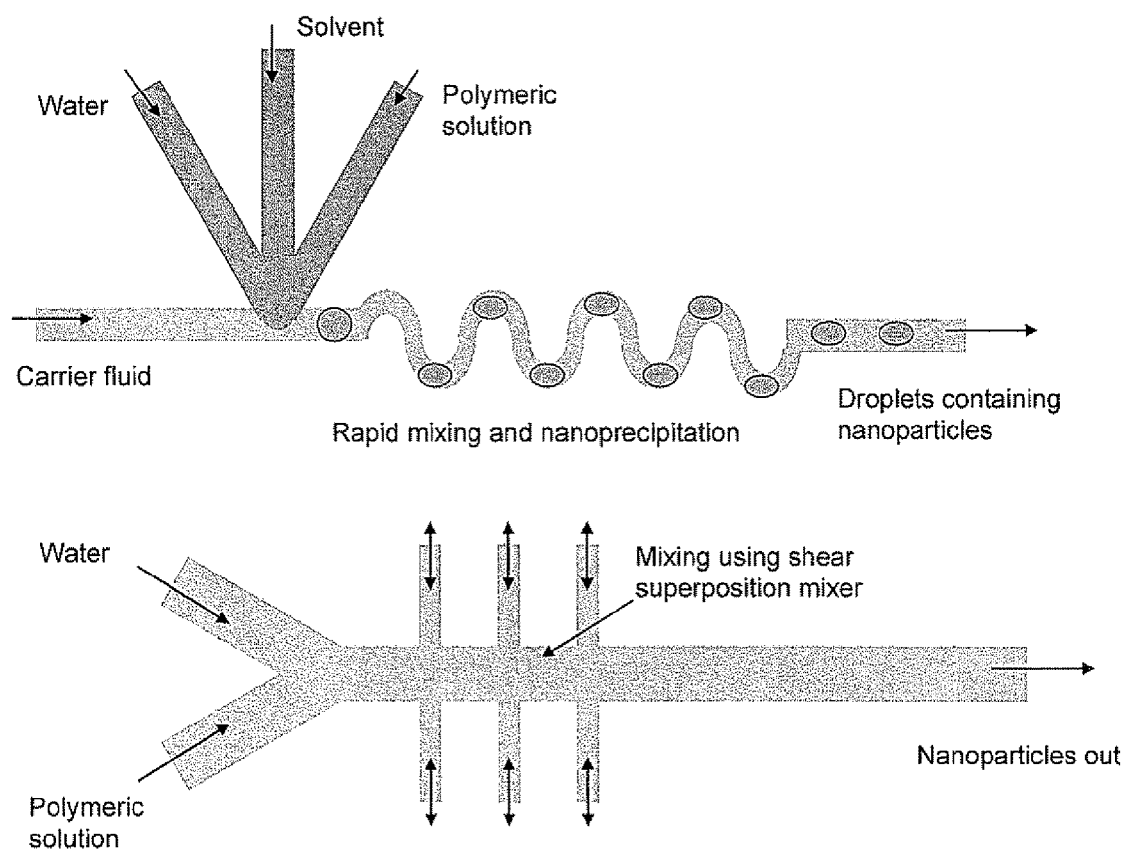
FIG. 3: Nanoparticle synthesis using a droplet mixer (top) and using a shear superposition mixer (bottom).

Two-phase flows in microfluidics display versatility in manipulation of nanoliter-sized droplets. Droplet-based mixers (Song et al., 2003, *Angewandte Chemie-Int'l Ed.*, 42:768) can be effective in mixing solutions at a wide range of flow rates and have found application in the synthesis of inorganic nanoparticles (Shestopalov et al., 2004, *Lab on a Chip*, 4:316). Nanoparticle synthesis can be carried out in droplet-based mixers by mixing aqueous and polymeric solutions inside droplets. FIG. 3 illustrates synthesis of nanoparticles in a droplet serpentine mixer. Aqueous and polymeric solution streams converge and intersect with another stream in which a carrier fluid immiscible with both water and solvent (e.g. a fluorocarbon) flows. The fluorocarbon stream may contain surfactants. Droplets containing the water and polymeric solution form, suspended in the carrier stream. The downstream section of the channel consists of wiggles that cause rapid mixing (Song et al., 2003, *Angewandte Chemie-Int'l Ed.*, 42:768) of water and polymer solutions inside each droplet. This results in an output stream of nanoparticles inside droplets. The nanoparticle solution can be separated from the carrier fluid by centrifugation.

Nanoparticle Synthesis Using a Shear Superposition Mixer

Another example of a mixer that can be used for nanoprecipitation is a shear superposition mixer (Bottausci et al., 2004, *Philosophical Transactions of the Royal Society of London Series a-Mathematical Physical and Engineering Sciences*, 362:1001). This is an example of an active mixer, as opposed to examples of passive mixers described above. A shear superposition mixer comprises a mixing channel with at least six side channels. Oscillating flows are applied on the side channels, which cause the fluid flowing in the mixing channel to mix (Bottausci et al., 2004, *Philosophical Transactions of the Royal Society of London Series a-Mathematical Physical and Engineering Sciences,* 362:1001). To synthesize nanoparticles, aqueous and polymeric streams flow and converge into the mixing channel as shown in FIG. 3. Oscillatory flows in the side channels result in efficient mixing of aqueous and polymer solutions, resulting in the formation of nanoparticles.

Microfluidic Devices

The present invention provides microfluidic devices for producing polymeric drug delivery particles. In general, a microfluidic device comprises at least two channels that converge into a mixing apparatus, and the channels join together at an angle ranging between zero degrees and 180 degrees. In some embodiments, the channels join together at an angle of approximately 10 degrees, approximately 20 degrees, approximately 30 degrees, approximately 40 degrees, approximately 50 degrees, approximately 60 degrees, approximately 70 degrees, approximately 80 degrees, approximately 90 degrees, approximately 100 degrees, approximately 110 degrees, approximately 120 degrees, approximately 130 degrees, approximately 140 degrees, approximately 150 degrees, approximately 160 degrees, or approximately 170 degrees. A stream of fluid is capable of flowing through each channel, and the streams join and flow into the mixing apparatus. Typically, inventive microfluidic devices comprise an outlet channel from the mixing apparatus.

In some embodiments, the flow of the streams through the channels is laminar. In some embodiments, the flow of the streams is characterized by a Reynolds number of approximately $10^{-5}$, approximately $10^{-4}$, approximately 0.001, approximately 0.01, approximately 0.1, approximately 1.0, approximately 10, approximately 100, approximately 1000, or approximately 2000. A schematic diagram of an exemplary microfluidic system is presented in FIG. 1.

In some embodiments, the channels and/or mixing apparatus have a circular cross-section. In some embodiments, the channels and/or mixing apparatus have an oval or ovaloid cross-section. In some embodiments, the channels and/or mixing apparatus have an elliptical or an ellipsoid cross-section. In some embodiments, the channels and/or mixing apparatus have a cross-section of irregular shape. In some embodiments, the channels that converge into the mixing apparatus are of uniform shape. In some embodiments, the channels that converge into the mixing apparatus are not of uniform shape.

In some embodiments, the width or height of each channel and/or mixing apparatus ranges from approximately 1 μm to approximately 1000 μm. In some embodiments, the width or height of each channel and/or mixing apparatus ranges from approximately 5 μm to approximately 500 μm. In some embodiments, the width or height of each channel and/or mixing apparatus ranges from approximately 10 μm to approximately 100 μm. In some embodiments, the width or height of each channel and/or mixing apparatus ranges from approximately 25 μm to approximately 100 μm. In some embodiments, the width or height of each channel and/or mixing apparatus ranges from approximately 50 μm to approximately 100 μm. In some embodiments, the width or height of each channel and/or mixing apparatus ranges from approximately 75 μm to approximately 100 μm. In some embodiments, the width or height of each channel and/or mixing apparatus ranges from approximately 10 μm to approximately 75 μm. In some embodiments, the width or height of each channel and/or mixing apparatus ranges from approximately 10 μm to approximately 50 μm. In some embodiments, the width or height of each channel and/or mixing apparatus ranges from approximately 10 μm to approximately 25 μm.

In some embodiments, the maximum width or height of a channel and/or mixing apparatus is approximately 1 μm, approximately 5 μm, approximately 10 μm, approximately 20 μm, approximately 30 μm, approximately 40 μm, approximately 50 μm, approximately 60 μm, approximately 70 μm, approximately 80 μm, approximately 90 μm, approximately 100 μm, approximately 250 μm, approximately 500 μm, or approximately 1000 μm.

In some embodiments, the width of each channel and/or mixing apparatus ranges from approximately 5 μm to approximately 100 μm. In some embodiments, the width of a channel and/or mixing apparatus is approximately 5 μm, approximately 10 μm, approximately 15 μm, approximately 20 μm, approximately 25 μm, approximately 30 μm, approximately 35 μm, approximately 40 μm, approximately 45 μm, approximately 50 μm, approximately 60 μm, approximately 70 μm, approximately 80 μm, approximately 90 μm, or approximately 100 μm. In specific embodiments, the width of the channel(s) through which the polymeric stream flows is approximately 20 μm. In specific embodiments, the width of the channel(s) through which the non-solvent flows is approximately 200 μm.

In some embodiments, the height of each channel and/or mixing apparatus ranges from approximately 10 μm to approximately 1000 μm. In some embodiments, the height of a channel and/or mixing apparatus is approximately 10 μm, approximately 100 μm, approximately 250 μm, approximately 400 μm, approximately 500 μm, approximately 600 μm, approximately 750 μm, or approximately 1000 μm. In specific embodiments, the height of the channel(s) through which the polymeric stream flows is approximately 500 μm. In specific embodiments, the height of the channel(s) through which the non-solvent flows is approximately 500 μm.

In some embodiments, the length of each channel and/or mixing apparatus ranges from approximately 100 μm to approximately 10 cm. In some embodiments, the length of a channel and/or mixing apparatus is approximately 100 μm, approximately 1.0 mm, approximately 10 mm, approximately 100 mm, approximately 500 mm, approximately 600 mm, approximately 700 mm, approximately 800 mm, approximately 900 mm, approximately 1.0 cm, approximately 1.1 cm, approximately 1.2 cm, approximately 1.3 cm, approximately 1.4 cm, approximately 1.5 cm, approximately 5 cm, or approximately 10 cm. In specific embodiments, the length of the channel(s) through which the polymeric stream flows is approximately 1.0 cm. In specific embodiments, the length of the channel(s) through which the non-solvent flows is approximately 1.0 cm.

In some embodiments, the channels that converge into a mixing apparatus are of uniform width, height, and/or length. In some embodiments, the channels that converge into a mixing apparatus are not of uniform width, height, and/or length.

In some embodiments, the channels that converge into a mixing apparatus are arranged in one plane relative to one another. In some embodiments, the channels that converge into a mixing apparatus and the mixing apparatus are all arranged in one plane relative to one another. In some embodiments, the channels that converge into a mixing apparatus are arranged in different planes relative to one another. In some embodiments, the channels that converge into a mixing apparatus and the mixing apparatus are all arranged in different planes relative to one another. In some embodiments, the channels that converge into a mixing apparatus are arranged in one plane relative to one another, and the mixing apparatus is arranged in a different plane relative to the channels that converge into the mixing apparatus.

In general, the channels join together at an angle greater than zero degrees. In some embodiments, the channels join together at an angle of approximately 90 degrees. In some embodiments, the channels join together at an angle of approximately 10 degrees, approximately 20 degrees, approximately 30 degrees, approximately 40 degrees, approximately 50 degrees, approximately 60 degrees, approximately 70 degrees, approximately 80 degrees, approximately 90 degrees, approximately 100 degrees, approximately 110 degrees, approximately 120 degrees, approximately 130 degrees, approximately 140 degrees, approximately 150 degrees, approximately 160 degrees, or approximately 170 degrees.

A channel and/or mixing apparatus may be composed of any material suitable for the flow of fluid through the channels and/or mixing apparatus. Typically, the material is one that is resistant to solvents and non-solvents that are used in the preparation of particles. In general, the material is not one that will dissolve or react with the solvent or non-solvent. In some embodiments, a channel and/or mixing apparatus is composed of glass, silicon, or combination thereof. In some embodiments, a channel and/or mixing apparatus is composed of a metal and/or metal alloys (e.g. iron, titanium, aluminum, gold, platinum, chromium, molybdenum, zirconium, silver, niobium, alloys thereof, etc.). In some embodiments, a channel and/or mixing apparatus is composed of a polymer and/or plastic, including, but not limited to, polycarbonate, polyethylene terephthalate (PET) polyethylene terephthalic ester (PETE), polytetrafluoroethylene (PTFE), polydimethylsiloxane (PDMS), polyurethane, bakelite, polyester, etc. In some embodiments, channels are composed of photocurable epoxy. In some embodiments, a channel and/or mixing apparatus is composed of polydimethylsiloxane. In some embodiments, a channel and/or mixing apparatus is composed of ceramics (e.g. silicon nitride, silicon carbide, titania, alumina, silica, etc.).

Figure 5:
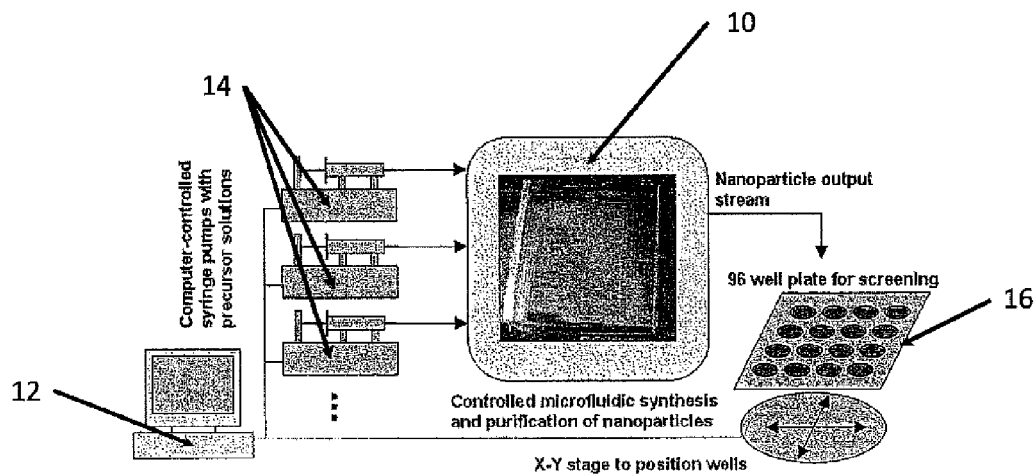
FIG. 5: System (10) for combinatorial synthesis of nanoparticles depicted in FIG. 4, Precursors for nanoparticle synthesis are loaded in separate syringes mounted on computer (12) controlled syringe pumps (14). Different formulations are produced sequentially and collected for screening using a collector (16) controlled by the same computer.
Figure 6:
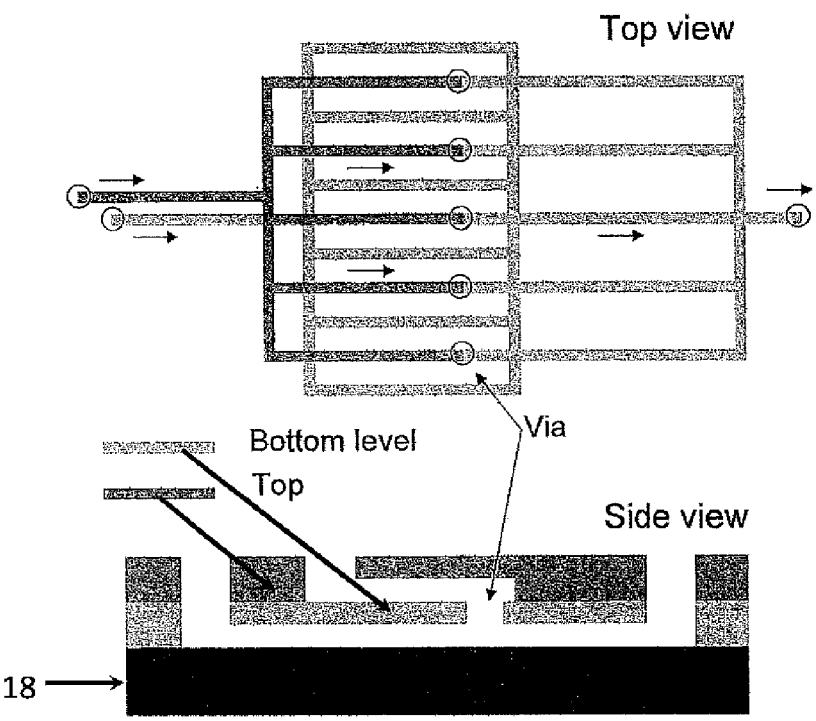
FIG. 6: Design for large-scale synthesis of nanoparticles using two-layer microfluidic channels on a substrate (18).

In some embodiments, inventive microfluidic devices may optionally comprise an apparatus for controlling temperature. For example, as shown in FIG. 5, syringe pumps (14) may include an apparatus for controlling the temperature of the precursor solutions. In some other embodiments, such as shown in FIG. 6, substrate (18) may be optionally cooled or heated at a temperature range from approximately 0 to 40° C. when contacted with an apparatus which can control the temperature using techniques known in the art of microfluidic devices. In certain embodiments, the particles are prepared in the microfluidic device at approximately room temperature. In certain embodiments, the particles are prepared in the microfluidic device at a temperature ranging from approximately 0° C. to approximately 10° C. In certain embodiments, the particles are prepared in the microfluidic device at a temperature ranging from approximately 10° C. to approximately 20° C. In certain embodiments, the particles are prepared in the microfluidic device at a temperature ranging from approximately 20° C. to approximately 30° C. In certain embodiments, the particles are prepared in the microfluidic device at a temperature ranging from approximately 30° C. to approximately 40° C.

In some embodiments, a channel and/or mixing apparatus is formed by lithography, etching, embossing, or molding of a polymeric surface. In general, the fabrication process may involve one or more of any of the processes described below (or similar processes), and different parts of a device may be fabricated using different methods and assembled or bonded together.

Lithography involves use of light or other form of energy such as electron beam to change a material. Typically, a polymeric material or precursor (e.g. photoresist, a light-resistant material) is coated on a substrate and is selectively exposed to light or other form of energy. Depending on the photoresist, exposed regions of the photoresist either remain or are dissolved in subsequent processing steps known generally as "developing." This process results in a pattern of the photoresist on the substrate. In some embodiments, the photoresist is used as a master in a molding process. In some embodiments, a polymeric precursor is poured on the substrate with photoresist, polymerized (i.e. cured) and peeled off. The resulting polymer is bonded or glued to another flat substrate after drilling holes for inlets and outlets.

In some embodiments, the photoresist is used as a mask for an etching process. For example, after patterning photoresist on a silicon substrate, channels can be etched into the substrate using a deep reactive ion etch (DRIE) process or other chemical etching process known in the art (e.g. plasma etch, KOH etch, HF etch, etc.). The photoresist is removed, and the substrate is bonded to another substrate using one of any bonding procedures known in the art (e.g. anodic bonding, adhesive bonding, direct bonding, eutectic bonding, etc.). Multiple lithographic and etching steps and machining steps such as drilling may be included as required.

In some embodiments, a polymeric substrate may be heated and pressed against a master mold for an embossing process. The master mold may be formed by a variety of processes, including lithography and machining. The polymeric substrate is then bonded with another substrate to form channels and/or a mixing apparatus. Machining processes may be included if necessary.

In some embodiments, a molten polymer or metal or alloy is injected into a suitable mold and allowed to cool and solidify for an injection molding process. The mold typically consists of two parts that allow the molded component to be removed. Parts thus manufactured may be bonded to result in the device.

In some embodiments, sacrificial etch may be used to form channels and/or a mixing apparatus. Lithographic techniques may be used to pattern a material on a substrate. This material is covered by another material of different chemical nature. This material may undergo lithography and etch processes, or other machining process. The substrate is then exposed to a chemical agent that selectively removes the first material. Channels are formed in the second material, leaving voids where the first material was present before the etch process.

In some embodiments, microchannels are directly machined into a substrate by laser machining or CNC machining. Several layers thus machined may be bonded together to obtain the final device. In specific embodiments, laser machining may be performed on polymer sheets commonly used for lamination (e.g., of certificates, identity cards, etc.). Lamination of machined sheets is used to form the device.

Typically, a source of fluid is attached to each channel, and the application of pressure to the source causes the flow of the fluid in the channel. In some embodiments, the pressure is applied by a syringe. In some embodiments, the pressure is applied by a pump. In some embodiments, the pressure is applied by gravity. In some embodiments, the applied pressure is regulatable (i.e. the applied pressure may be increased, decreased, or held constant). In some embodiments, the flow rate is regulatable by adjusting the applied pressure. In some embodiments, the flow rate is regulatable by adjusting the size (e.g. length, width, and/or height) of the channel. In some embodiments, the flow rate may range from 0.001 µl/min to 1.0 ml/min. In some embodiments, the flow rate is approximately 0.01 µl/min, approximately 0.1 µl/min, approximately 0.5 µl/min, approximately 1.0 µl/min, approximately 5 µl/min, approximately 10 µl/min, approximately 50 µl/min, approximately 100 µl/min, or approximately 1.0 ml/min. In specific embodiments, the flow rate is approximately 10 µl/min for aqueous solutions (e.g. a non-solvent such as water). In specific embodiments, the flow rate is approximately 0.5 µl/min for polymeric solutions.

In some embodiments, the same amount of pressure is applied to all of the channels. In some embodiments, different amounts of pressure are applied to different channels. Thus, in some embodiments, the flow rate may be the same through all channels, or the flow rate may be different in different channels.

Figure 4:
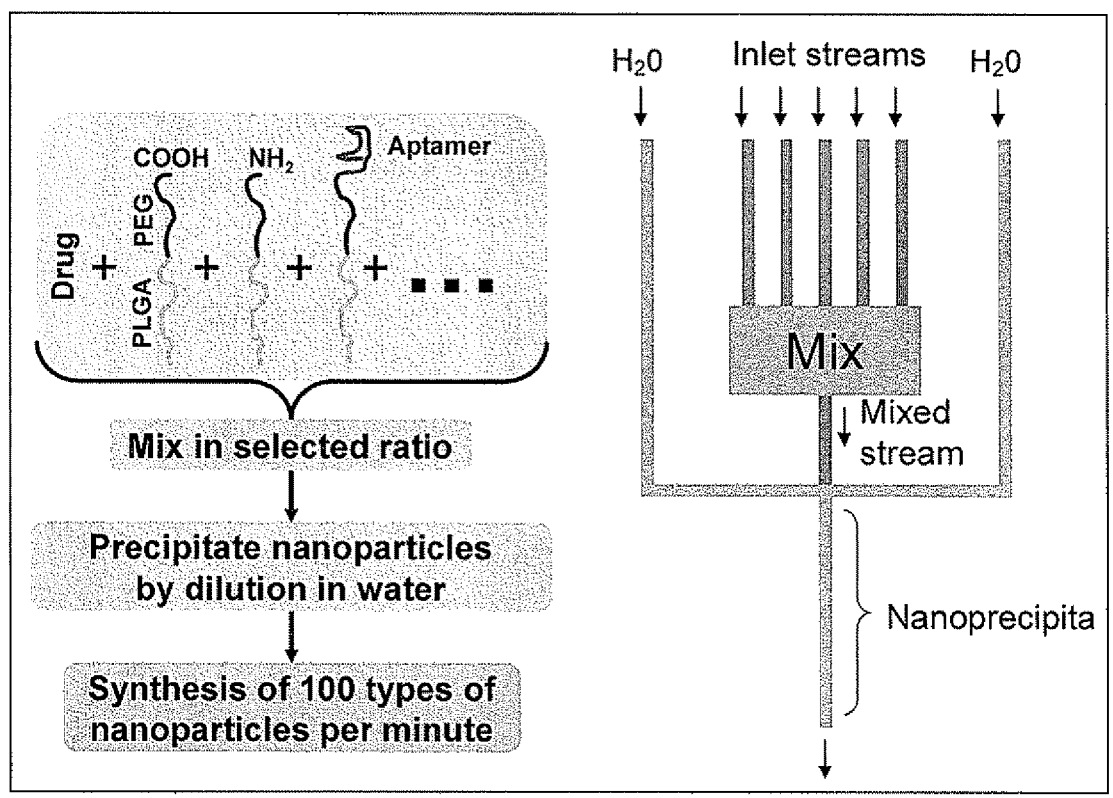
FIG. 4: Method for combinatorial synthesis of nanoparticles. Composition of the polymeric stream may be varied by controlling the flow rates of inlet streams that subsequently mix and form the polymeric stream. The polymeric stream is then used for nanoprecipitation using hydrodynamic focusing to form nanoparticles.

The present invention provides microfluidic systems in which a plurality of inlet streams converge and mix, and the resulting mixture is the polymeric stream that flows into a mixing apparatus (for example, see FIG. 4). In some embodiments, a microfluidic system may comprise at least 2, at least 3, at least 4, at least 5, at least 6, at least 7, at least 8, at least 9, at least 10, or more inlet streams. The flow of each inlet stream is regulated by a source of fluid, wherein the application of pressure to the source causes the flow of fluid in the inlet stream. In some embodiments, the pressure is applied by a syringe. In some embodiments, the pressure is applied by a pump. In some embodiments, the pressure is applied by gravity. In some embodiments, the applied pressure is regulatable (i.e. the applied pressure may be increased, decreased, or held constant). In some embodiments, the flow rate is regulatable by adjusting the applied pressure.

In some embodiments, the same amount of pressure is applied to all of the inlet streams. In some embodiments, different amounts of pressure are applied to different inlet streams. Thus, in some embodiments, the flow rate may be the same through all inlet streams, or the flow rate may be different in different inlet streams.

In some embodiments, inventive microfluidic systems produce particles at a rate ranging from approximately 0.1 mg/min to approximately 1 g/min. In some embodiments, inventive microfluidic systems produce particles at a rate ranging from approximately 1.0 mg/min to approximately 500 mg/min. In some embodiments, inventive microfluidic systems produce particles at a rate ranging from approximately 10 mg/min to approximately 100 g/min.

In specific embodiments, inventive microfluidic systems which involve one channel hydrodynamic focusing produce particles at a rate ranging from 0.01 mg/min to 1.0 mg/min. In specific embodiments, inventive microfluidic systems which involve hydrodynamic focusing produce particles at a rate of approximately 0.01 mg/min, approximately 0.1 mg/min, approximately 0.5 mg/min, approximately 1.0 mg/min, or greater than 1.0 mg/min. Inventive microfluidic systems which involve parallel channel hydrodynamic focusing produce particles at correspondingly faster rates.

In specific embodiments, inventive microfluidic systems which involve the use of mixers, such as those described herein, produce particles at a rate ranging from 0.01 mg/min to 100 mg/min. In specific embodiments, inventive microfluidic systems which involve the use of mixers, such as those described herein, produce particles at a rate of approximately 0.01 mg/min to 1.0 mg/min. In specific embodiments, inventive microfluidic systems which involve hydrodynamic focusing produce particles at a rate of approximately 0.01 mg/min, approximately 0.1 mg/min, approximately 1.0 mg/min, approximately 10 mg/min, approximately 100 mg/min, or greater than 100 mg/min. Inventive microfluidic systems which involve the use of mixers and parallel channels produce particles at correspondingly faster rates.

In some embodiments, inventive microfluidic systems produce particles at an average rate of approximately 0.1 mg/min. In some embodiments, inventive microfluidic systems produce particles at an average rate of approximately 1.0 mg/min. In some embodiments, inventive microfluidic systems produce particles at an average rate of approximately 10 mg/min. In some embodiments, inventive microfluidic systems produce particles at an average rate of approximately 100 mg/min. In some embodiments, inventive microfluidic systems produce particles at an average rate of approximately 500 mg/min. In some embodiments, inventive microfluidic systems produce particles at an average rate of approximately 1.0 g/min.

Purification steps are optionally performed after synthesis of particles. Typically, purification is carried out by solvent evaporation to remove the organic solvent, followed by centrifugation and washing. Typically, the solution is exposed to air (and, optionally, to a vacuum) for a period ranging from 1 minute to 10 hours, depending on the volume and container. In some embodiments, the solution is exposed to air and/or a vacuum for approximately 1 minute, approximately 10 minutes, approximately 30 minutes, approximately 1 hour, approximately 2 hours, approximately 5 hours, or approximately 10 hours. The volatile solvent evaporates, leaving behind a purified solution of the nanoparticles in water. Alternatively or additionally, the solution may be centrifuged in order to settle the particles. The supernatant is removed, and the particles may be resuspended in water. Particles may be filtered (e.g. through 200 nm filters or any other filters) prior to use.

The purification processes described above can be time-consuming. The present invention provides methods for integrating microfluidic purification processes in line with nanoprecipitation. Using integrated filtration processes, inventive microfluidic device can enable synthesis of ready-to-use nanoparticles with minimal labor and time consumption. Diffusion-based separation processes such as the H-filter can be used for separating nanoparticles with small diffusivities (typically $<10^{-11}$ m$^2$/s) from other components such as organic solvents and residual polymers (if any) that have much higher diffusivities. An H-filter comprises two channels—one containing the stream to be purified and another containing an aqueous stream—that join together to form a common channel. The common channel then splits into two channels—one containing waste (e.g. solvent and/or small molecules or particles) and the other containing purified particles. In some embodiments, the mean diameter of H-filter channels ranges from 1.0 µm to 100 µm. In some embodiments, the mean diameter of H-filter channels is approximately 1.0 µm, approximately 10 µm, or approximately 100 µm. In some embodiments, the length of H-filter channels ranges from 100 µm to 10 cm. In some embodiments, the length of H-filter channels is approximately 100 µm, approximately 1 mm, approximately 10 mm, approximately 100 mm, approximately 1.0 cm, or approximately 10 cm.

Fabrication of Microfluidic Devices

Microfluidic devices may be fabricated in a wide variety of ways. Example 1 describes two methods that can be used in order to fabricate microfluidic devices. In the first method, a photocurable epoxy was spun onto a glass wafer to a thickness of 40 µm-100 µm. After standard lithography procedures, microchannels were obtained on the wafer. Holes were drilled in the wafer and another wafer was bonded to the first wafer to form enclosed microchannels. Connections were made from syringes to the device using tubing and sealing the tubing to the device using epoxy. This device had microchannels made of glass and epoxy. In the second method presented in Example 1, standard procedures of soft lithography were used to make the devices from polydimethylsiloxane (PDMS). The device was obtained by first making a master mold using epoxy lithography followed by silane treatment. PDMS pre-polymer and a curing agent were mixed in the ratio prescribed by the manufacturer, poured on the master mold, and cured. PDMS was peeled off, holes were drilled, and it was bonded to a glass slide using oxygen plasma treatment in order to obtain a microfluidic device.

Fluid Streams

The present invention provides microfluidic systems for producing polymeric particles comprising multiple channels that converge into a mixing apparatus. Streams of fluid flow through each channel, and the streams join and flow into the mixing apparatus. In general, a polymeric solution comprising a polymer and a solvent flows through at least one channel, and a non-solvent flows through at least one channel. As used herein, the term "solvent" refers to a substance in which a polymer is more soluble than a "non-solvent." One of ordinary skill in the art will understand that the terms "solvent" and "non-solvent" have meaning that is relative to one another. In other words, a polymer may be more soluble in substance A than in substance B. Thus, substance A is a "solvent" and substance B is a "non-solvent" for that particular polymer. However, a second polymer may be more soluble in substance B than in substance A. Thus, in this instance, substance B is the "solvent" and substance A is the "non-solvent" for the second polymer. In some embodiments, the polymer may be 2×, 3×, 4×, 5×, 10×, 100×, or more soluble in the solvent than in the non-solvent. In some embodiments, the polymer may be 10%, 20%, 50%, 75%, 90%, or greater than 90% more soluble in the solvent than in the non-solvent.

Typically, in accordance with the present invention, the solvent comprises at least one organic solvent, and the non-solvent is an aqueous solution. In certain embodiments, the solvent is water-miscible, and in other embodiments, the solvent is not water-miscible. In some embodiments, the solvent and/or the non-solvent may further comprise one or more surfactants; therapeutic agents (including drugs, diagnostic agents, and/or prophylactic agents); targeting moieties; or other components, as described in further detail below.

In some embodiments, the solvent is at least one of 1,4-dioxane, tetrahydrofuran (THF), diethylether, methylethylether, dimethylether, acetone, acetonitrile, dimethyl sulfoxide (DMSO), dimethylformamide (DMF), glyme, ethyl acetate, hexane, polyethylene glycol, glycerin, acids, and alcohols (e.g. methanol, ethanol, isopropanol, butanol, etc.).

In some embodiments, the non-solvent comprises water. In some embodiments, the non-solvent is combined with a sufficient amount of solvent to slow down the rate of solvent diffusion out of the polymeric stream.

Polymers

Any polymer may be used in the microfluidic systems of the present invention. Polymers may be natural or unnatural (i.e. synthetic) polymers. Polymers may be homopolymers or copolymers comprising two or more monomers. In terms of sequence, copolymers may be random, block, graft, or comprise a combination of random, block, and/or graft sequences. In some embodiments, block copolymers are diblock copolymers. In some embodiments, block copolymers are triblock copolymers. In some embodiments, polymers can be linear or branched polymers. In some embodiments, polymers in accordance with the invention comprise blends, mixtures, and/or adducts of any of the polymers described herein. Typically, polymers in accordance with the present invention are organic polymers.

In some embodiments, the polymer is selected from the group consisting of polyalkylenes (e.g. polyethylenes), polycarbonates (e.g. poly(1,3-dioxan-2one)), polyanhydrides (e.g. poly(sebacic anhydride)), polyhydroxyacids (e.g. poly (β-hydroxyalkanoate)), polyfumarates, polycaprolactones, polyamides (e.g. polycaprolactam), polyacetals, polyethers, polyesters (e.g. polylactide, polyglycolide), poly(orthoesters), polyvinyl alcohols, polyurethanes, polyphosphazenes, polyacrylates, polymethacrylates, polycyanoacrylates, polyureas, polystyrenes, and polyamines.

In some embodiments, polymers in accordance with the present invention include polymers which have been approved for use in humans by the U.S. Food and Drug Administration (FDA) under 21 C.F.R. §177.2600, including but not limited to polyesters (e.g. polylactic acid, polyglycolic acid, poly(lactic-co-glycolic acid), polycaprolactone, polyvalerolactone, poly(1,3-dioxan-2one)); polyanhydrides (e.g. poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g. phosphate group, sulphate group, carboxylate group); cationic groups (e.g. quaternary amine group); or polar groups (e.g. hydroxyl group, thiol group, amine group). In some embodiments, polymers can be hydrophobic. In some embodiments, polymers can be cationic. In some embodiments, polymers can be anionic. In some embodiments, polymers can be of neutral charge.

In some embodiments, polymers may be modified with one or more moieties and/or functional groups. Any moiety or functional group can be used in accordance with the present invention. In some embodiments, polymers may be modified with polyethylene glycol (PEG), with a carbohydrate, and/or with acyclic polyacetals derived from polysaccharides (Papisov, 2001, *ACS Symposium Series*, 786:301). In certain embodiments, a polymer may be a PEG-polymer copolymer.

In some embodiments, polymers may be modified with a lipid or fatty acid group, properties of which are described in further detail below. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; copolymers of PLGA and PEG; polymers and copolymers of lactide and glycolide (e.g. copolymers of PLA and PEG, copolymers of PGA and PEG, copolymers of PLGA and PEG, and derivatives thereof). In some embodiments, the polymer is a copolymer of polyethylene glycol and PLGA. In some embodiments, polymers include, for example, polyanhydrides; poly(ortho ester); copolymers of poly(ortho ester)

and PEG; poly(caprolactone); copolymers of poly(caprolactone) and PEG; polylysine; copolymers of polylysine and PEG; poly(ethylene imine); copolymers of poly(ethylene imine) and PEG; poly(L-lactide-co-L-lysine); poly(serine ester); poly(4-hydroxy-L-proline ester); poly[α-(4-aminobutyl)-L-glycolic acid]; and derivatives thereof.

In some embodiments, the polymer is PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid: glycolic acid ratio. In some embodiments, PLGA to be used in accordance with the present invention is characterized by a lactic acid:glycolic acid ratio of approximately 85:15, approximately 75:25, approximately 60:40, approximately 65:35, approximately 50:50, approximately 40:60, approximately 25:75, or approximately 15:85.

In some embodiments, the polymer is one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly (methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, the polymer is a carbohydrate. In some embodiments, a carbohydrate is a polysaccharide comprising simple sugars (or their derivatives) connected by glycosidic bonds, as known in the art. In some embodiments, a carbohydrate is one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, the polymer may be a protein or peptide. Exemplary proteins that may be used in accordance with the present invention include, but are not limited to, albumin, collagen, etc.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, *J. Am. Chem. Soc.*, 123:9480; Lim et al., 2001, *J. Am. Chem. Soc.*, 123:2460; Langer, 2000, *Acc. Chem. Res.*, 33:94; Langer, 1999, *J. Control. Release*, 62:7; and Uhrich et al., 1999, *Chem. Rev.*, 99:3181). More generally, a variety of methods for synthesizing suitable polymers are described in *Concise Encyclopedia of Polymer Science and Polymeric Amines and Ammonium Salts*, Ed. by Goethals, Pergamon Press, 1980; *Principles of Polymerization* by Odian, John Wiley & Sons, Fourth Edition, 2004; *Contemporary Polymer Chemistry* by Allcock et al., Prentice-Hall, 1981; Deming et al., 1997, *Nature*, 390:386; and in U.S. Pat. Nos. 6,506,577, 6,632,922, 6,686,446, and 6,818,732.

Those skilled in the art will recognize that the polymers listed herein represent an exemplary, not comprehensive, list of polymers that can be of use in accordance with the present invention.

Therapeutic Agents

In some embodiments, fluid streams may optionally comprise one or more therapeutic agents (including drugs, diagnostic agents, and/or prophylactic agents) to be associated with the surface of, encapsulated within, surrounded by, and/or dispersed throughout particles produced using inventive microfluidic systems.

Exemplary therapeutic agents that may be used in accordance with the present invention include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof.

In some embodiments, particles produced using inventive microfluidic systems comprise less than 50% by weight, less than 40% by weight, less than 30% by weight, less than 20% by weight, less than 15% by weight, less than 10% by weight, less than 5% by weight, less than 1% by weight, less than 0.5% by weight, or less than 0.1% by weight of the therapeutic agent. In some embodiments, the therapeutic agent may be a mixture of pharmaceutically active agents.

Small Molecule Agents

In some embodiments, the therapeutic agent is a small molecule and/or organic compound with pharmaceutical activity. In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, antipyretic, birth control agent, hormone, prostaglandin, progestational agent, anti-glaucoma agent, ophthalmic agent, anticholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitor of DNA, RNA, or protein synthesis, etc.

In certain embodiments, a small molecule agent can be any drug. In some embodiments, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

A more complete listing of classes and specific drugs suitable for use in the present invention may be found in *Pharmaceutical Drugs: Syntheses, Patents, Applications* by Axel Kleemann and Jurgen Engel, Thieme Medical Publishing, 1999 and the *Merck Index: An Encyclopedia of Chemicals, Drugs and Biologicals*, Ed. by Budavari et al, CRC Press, 1996, both of which are incorporated herein by reference.

Nucleic Acid Agents

In certain embodiments of the invention, the therapeutic agent is a nucleic acid (e.g. DNA, RNA, derivatives thereof, etc.). In some embodiments, the nucleic acid agent is a functional RNA. In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g. short interfering RNAs (siRNAs), short hairpin RNAs (shRNAs), and microRNAs), ribozymes, tRNAs, rRNAs, RNAs useful for triple helix formation, etc.

In some embodiments, the nucleic acid agent is a vector. As used herein, the term "vector" refers to a nucleic acid molecule (typically, but not necessarily, a DNA molecule) which can transport another nucleic acid to which it has been linked. A vector can achieve extra-chromosomal replication and/or expression of nucleic acids to which they are linked in a host cell. In some embodiments, a vector can achieve integration into the genome of the host cell.

In some embodiments, vectors are used to direct protein and/or RNA expression. In some embodiments, the protein and/or RNA to be expressed is not normally expressed by the cell. In some embodiments, the protein and/or RNA to be expressed is normally expressed by the cell, but at lower levels than it is expressed when the vector has not been delivered to the cell. In some embodiments, a vector directs expression of any of the functional RNAs described herein, such as RNAi-inducing entities, ribozymes, etc.

Protein Agents

In some embodiments, the therapeutic agent may be a protein or peptide. The terms "protein," "polypeptide," and "peptide" can be used interchangeably. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size.

Polypeptides may contain L-amino acids, D-amino acids, or both and may contain any of a variety of amino acid modifications or analogs known in the art. Useful modifications include, e.g. terminal acetylation, amidation, etc. In some embodiments, polypeptides may comprise natural amino acids, unnatural amino acids, synthetic amino acids, and combinations thereof, as described herein.

In some embodiments, the therapeutic agent may be a hormone, erythropoietin, insulin, cytokine, antigen for vaccination, growth factor, etc. In some embodiments, the therapeutic agent may be an antibody and/or characteristic portion thereof. In some embodiments, antibodies may include, but are not limited to, polyclonal, monoclonal, chimeric (i.e. "humanized"), or single chain (recombinant) antibodies. In some embodiments, antibodies may have reduced effector functions and/or bispecific molecules. In some embodiments, antibodies may include Fab fragments and/or fragments produced by a Fab expression library (e.g. Fab, Fab', F(ab')2, scFv, Fv, dsFv diabody, and Fd fragments).

Carbohydrate Agents

In some embodiments, the therapeutic agent is a carbohydrate. In certain embodiments, the carbohydrate is a carbohydrate that is associated with a protein (e.g. glycoprotein, proteogycan, etc.). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

Lipid Agents

In some embodiments, the therapeutic agent is a lipid. In certain embodiments, the lipid is a lipid that is associated with a protein (e.g. lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g. vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

Diagnostic Agents

In some embodiments, the therapeutic agent is a diagnostic agent. In some embodiments, diagnostic agents include commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, a diagnostic and/or therapeutic agent may be a radionuclide. Among the radionuclides used, gamma-emitters, positron-emitters, and X-ray emitters are suitable for diagnostic and/or therapeutic purposes, while beta emitters and alpha-emitters may also be used for therapy. Suitable radionuclides for use in the invention include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}O$, $^{32}P$, $^{33}P$, and $^{18}F$.

In some embodiments, a diagnostic agent may be a fluorescent, luminescent, or magnetic moiety. Fluorescent and luminescent moieties include a variety of different organic or inorganic small molecules commonly referred to as "dyes,"

"labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site).

Prophylactic Agents

In some embodiments, the therapeutic agent is a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococcus pnuemoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Nutraceutical Agents

In some embodiments, the therapeutic agent is a nutraceutical agent. In some embodiments, the nutraceutical agent provides basic nutritional value, provides health or medical benefits, and/or is a dietary supplement. In some embodiments, the nutraceutical agent is a vitamin (e.g. vitamins A, B, C, D, E, K, etc.), mineral (e.g. iron, magnesium, potassium, calcium, etc.), or essential amino acid (e.g. lysine, glutamine, leucine, etc.).

In some embodiments, nutraceutical agents may include plant or animal extracts, such as fatty acids and/or omega-3 fatty acids (e.g. DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g. cod liver oil), and probiotics.

Exemplary nutraceutical agents and dietary supplements are disclosed, for example, in Roberts et al., (*Nutriceuticals: The Complete Encyclopedia of Supplements, Herbs, Vitamins, and Healing Foods*, American Nutriceutical Association, 2001). Nutraceutical agents and dietary supplements are also disclosed in *Physicians' Desk Reference for Nutritional Supplements*, 1st Ed. (2001) and *The Physicians' Desk Reference for Herbal Medicines*, 1st Ed. (2001).

Those skilled in the art will recognize that this is an exemplary, not comprehensive, list of therapeutic agents (including drugs, diagnostic agents, and/or prophylactic agents) that can be associated with particles produced using inventive microfluidic systems. Any therapeutic agent may be associated with particles made using microfluidic systems in accordance with the present invention.

Targeting Moieties

In some embodiments, fluid streams may optionally comprise one or more targeting moieties. A targeting moiety is any moiety that binds to a component associated with an organ, tissue, cell, extracellular matrix component, and/or intracellular compartment. Thus, inclusion of a targeting moiety in one or more of the fluid streams can result in production of particles which can be targeted to a particular organ, tissue, cell, extracellular matrix component, and/or intracellular compartment (i.e. a "target" or a "marker").

A targeting moiety may be a nucleic acid, polypeptide, glycoprotein, carbohydrate, lipid, etc. For example, a targeting moiety can be a nucleic acid targeting moiety (e.g. an aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g. a growth factor, hormone, LDL, transferrin, etc. A targeting moiety can be an antibody, which term is intended to include antibody fragments, characteristic portions of antibodies, single chain antibodies, etc. Synthetic binding proteins such as affibodies, etc., can be used. Peptide targeting moieties can be identified, e.g., using procedures such as phage display. This widely used technique has been used to identify cell specific ligands for a variety of different cell types.

In some embodiments, targeting moieties bind to an organ, tissue, cell, extracellular matrix component, and/or intracellular compartment that is associated with a specific developmental stage or a specific disease state. In some embodiments, a target is an antigen on the surface of a cell, such as a cell surface receptor, an integrin, a transmembrane protein, an ion channel, and/or a membrane transport protein. In some embodiments, a target is an intracellular protein. In some embodiments, a target is a soluble protein, such as immunoglobulin. In certain specific embodiments, a target is a tumor marker. In some embodiments, a tumor marker is an antigen that is present in a tumor that is not present in normal tissue. In some embodiments, a tumor marker is an antigen that is more prevalent in a tumor than in normal tissue. In some embodiments, a tumor marker is an antigen that is more prevalent in malignant cancer cells than in normal cells.

In specific embodiments, a target is preferentially expressed in tumor tissues versus normal tissues. For example, when compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al., 1997, *Clin. Cancer Res.*, 3:81).

In some embodiments, targeting moieties may be associated with the surface of, encapsulated within, surrounded by, and/or distributed throughout the polymeric matrix of the produced particles. In certain embodiments, the targeting moiety is covalently bound to a polymer of which the particle matrix is comprised. In some embodiments, inventive targeted particles comprise less than 50% by weight, less than 40% by weight, less than 30% by weight, less than 20% by weight, less than 15% by weight, less than 10% by weight, less than 5% by weight, less than 1% by weight, or less than 0.5% by weight of the targeting moiety.

Nucleic Acid Targeting Moieties

As used herein, a "nucleic acid targeting moiety" is a nucleic acid that binds selectively to a target. In some embodiments, a nucleic acid targeting moiety is a nucleic acid aptamer (see, e.g. copending PCT Patent Application US07/07927, filed Mar. 30, 2007, entitled "SYSTEM FOR TARGETED DELIVERY OF THERAPEUTIC AGENTS"). An aptamer is usually a polynucleotide that binds to a specific target structure that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g. hairpin loops) that disrupt base pairing.

One of ordinary skill in the art will recognize that any aptamer that is capable of specifically binding to a target can be used in accordance with the present invention. In some embodiments, aptamers to be used in accordance with the present invention may target cancer-associated targets. For example, aptamers to be used in accordance with the present invention may target tumor markers.

In certain embodiments, aptamers to be used in accordance with the present invention may target prostate cancer associated antigens, such as PSMA. Exemplary PSMA-targeting aptamers to be used in accordance with the present invention include, but are not limited to, the A10 aptamer, having a nucleotide sequence of 5'-GGGAGGACGAUGCG-GAUCAGCCAUGUUUACGUCACUCCUUGUCAAUCC UCAUCGGCAGACGACUCGCCCGA-3' (SEQ ID NO.: 1) (Lupold et al., 2002, *Cancer Res.*, 62:4029), the A9 aptamer, having nucleotide sequence of 5'-GGGAGGACGAUGCG-GACCGAAAAAGACCUGACUUCUAUACUAAGUCUA CGUUCCCAGACGACUCGCCCGA-3' (SEQ ID NO.: 2) (Lupold et al., 2002, *Cancer Res.*, 62:4029; and Chu et al., 2006, *Nuc. Acid Res.*, 34:e73), derivatives thereof, and/or characteristic portions thereof.

In some embodiments, a nucleotide sequence that is homologous to a nucleic acid targeting moiety may be used in accordance with the present invention. In some embodiments, a nucleotide sequence is considered to be "homologous" to a nucleic acid targeting moiety if it comprises fewer than 30, 25, 20, 15, 10, 5, 4, 3, 2, or 1 nucleic acid substitutions relative to the aptamer. In some embodiments, a nucleotide sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% identical. In some embodiments, a nucleic acid sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% similar.

Nucleic acids of the present invention (including nucleic acid targeting moieties and/or functional RNAs to be delivered, e.g., RNAi agents, ribozymes, tRNAs, etc.) may be prepared according to any available technique including, but not limited to chemical synthesis, enzymatic synthesis, enzymatic or chemical cleavage of a longer precursor, etc. Methods of synthesizing RNAs are known in the art (see, e.g. Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in molecular biology, v. 288 (Clifton, N.J.) Totowa, N.J.: Humana Press, 2005).

A nucleic acid that forms the nucleic acid targeting moiety may comprise naturally occurring nucleosides, modified nucleosides, naturally occurring nucleosides with hydrocarbon linkers (e.g. an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid targeting moiety can be replaced with a hydrocarbon linker or a polyether linker provided that the binding affinity and selectivity of the nucleic acid targeting moiety is not substantially reduced by the substitution (e.g. the dissociation constant of the nucleic acid targeting moiety for the target should not be greater than about $1 \times 10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) *Antisense Drug Technology: Principles, Strategies, and Applications* ($1^{st}$ ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, $SR_1$, $NH_2$, $NH_R$, $NR_2$ or CN, wherein R is $C_1$-$C_6$ alkyl, alkenyl, or alkynyl, and halo is F, Cl, Br or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g. aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of an aptamer such that the ability of the aptamer to specifically bind to the aptamer target is not substantially affected. The modified region may be at the 5'-end and/or the 3'-end of one or both strands. For example, modified aptamers in which approximately 1-5 residues at the 5' and/or 3' end of either of both strands are nucleotide analogs and/or have a backbone modification have been employed. The modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic agent, improved specific binding of an aptamer to an aptamer target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the aptamer are inverted to yield a such as a 3'-3' linkage or a 5'-5' linkage.

In some embodiments, nucleic acids in accordance with the present invention are not synthetic, but are naturally-occurring entities that have been isolated from their natural environments.

Small Molecule Targeting Moieties

In some embodiments, a targeting moiety in accordance with the present invention may be a small molecule. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

One of ordinary skill in the art will appreciate that any small molecule that specifically binds to a desired target can be used in accordance with the present invention. One exemplary small molecule targeting moiety is folic acid. Folic acid (i.e., pteroylglutamic acid, Vitamin B9) specifically binds to the folate receptor (FR), which is preferentially expressed in tumor tissues relative to healthy tissues (Low et al., 2004, *Adv. Drug Deliv. Rev.*, 56:1055).

In some embodiments, small molecule targeting moieties that may be used to target cells associated with prostate cancer tumors include PSMA peptidase inhibitors, such as 2-PMPA, GPI5232, VA-033, phenylalkylphosphonamidates (Jackson et al., 2001, *Curr. Med. Chem.*, 8:949; Bennett et al., 1998, *J. Am. Chem. Soc.*, 120:12139; Jackson et al., 2001, *J. Med. Chem.*, 44:4170; Tsukamoto et al., 2002, *Bioorg. Med. Chem. Lett.*, 12:2189; Tang et al., 2003, *Biochem. Biophys. Res. Commun.*, 307:8; Oliver et al., 2003, *Bioorg. Med. Chem.*, 11:4455; and Maung et al., 2004, *Bioorg. Med. Chem.*, 12:4969), and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives (Majer et al., 2003, *J. Med. Chem.*, 46:1989; and U.S. Patent Publication 2005/0080128). In some embodiments, small molecule targeting moieties that may be used to target cells associated with prostate cancer tumors include hydroxamate derivatives (Stoermer et al., 2003, *Bioorg. Med. Chem. Lett.*, 13:2097). In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al., 2000, *J. Med. Chem.*, 43:772; and Kozikowski et al., 2004, *J. Med. Chem.*, 47:1729), and/or and analogs and derivatives thereof. In some embodiments, small molecule targeting moieties that may be used to target cells associated with prostate cancer tumors include androgen receptor targeting agents (ARTAs), such as those described in U.S. Pat. Nos. 7,026,500; 7,022, 870; 6,998,500; 6,995,284; 6,838,484; 6,569,896; 6,492,554; and in U.S. Patent Publications 2006/0287547; 2006/ 0276540; 2006/0258628; 2006/0241180; 2006/0183931; 2006/0035966; 2006/0009529; 2006/0004042; 2005/ 0033074; 2004/0260108; 2004/0260092; 2004/0167103; 2004/0147550; 2004/0147489; 2004/0087810; 2004/ 0067979; 2004/0052727; 2004/0029913; 2004/0014975; 2003/0232792; 2003/0232013; 2003/0225040; 2003/ 0162761; 2004/0087810; 2003/0022868; 2002/0173495; 2002/0099096; 2002/0099036. In some embodiments, small molecule targeting moieties that may be used to target cells associated with prostate cancer tumors include polyamines, such as putrescine, spermine, and spermidine (U.S. Patent Publications 2005/0233948 and 2003/0035804).

Protein Targeting Moieties

In some embodiments, a targeting moiety in accordance with the present invention may be a polypeptide. As used herein, a "peptide" or "polypeptide" generally refers to a string of at least two amino acids linked to one another by peptide bonds. In certain embodiments, polypeptides range from about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size. The terms "polypeptide" and "peptide" are used interchangeably herein, with "peptide" typically referring to a polypeptide having a length of less than about 100 amino acids. In some embodiments, a peptide sequence can be based on the sequence of a protein. In some embodiments, a peptide sequence can be a random arrangement of amino acids.

Polypeptides may comprise L-amino acids, D-amino acids, or both and may contain any of a variety of amino acid modifications or analogs known in the art. Useful modifications include, e.g. terminal acetylation, amidation, lipidation, phosphorylation, glycosylation, acylation, fanesylation, sulfation, etc.

In some embodiments, targeting moieties can be proteins. In some embodiments, a protein may be a single polypeptide chain. In some embodiments, a protein may comprise more than one polypeptide chain, for example linked by one or more disulfide bonds or associated by other means. One of ordinary skill in the art will appreciate that any protein that specifically binds to a desired target can be used in accordance with the present invention. Exemplary proteins that may be used as targeting moieties in accordance with the present invention include, but are not limited to, antibodies, receptors, cytokines, peptide hormones, proteins derived from combinatorial libraries (e.g. avimers, affibodies, etc.), and characteristic portions thereof.

To give but a few examples, IL-2, transferrin, GM-CSF, α-CD25, α-CD22, TGF-α, folic acid, α-CEA, α-EpCAM scFV, VEGF, LHRH, bombesin, somatostin, Gal, α-GD2, α-EpCAM, α-CD20, MOv19 scFv, α-Her-2, and α-CD64 can be used to target a variety of cancers, such as lymphoma, glioma, leukemia, brain tumors, melanoma, ovarian cancer, neuroblastoma, folate receptor-expressing tumors, CEA-expressing tumors, EpCAM-expressing tumors, VEGF-expressing tumors, etc. (Eklund et al., 2005, *Expert Rev. Anticancer Ther.*, 5:33; Kreitman et al., 2000, *J. Clin. Oncol.*, 18:1622; Kreitman et al., 2001, *N. Engl J. Med.*, 345:241; Sampson et al., 2003, *J. Neurooncol.*, 65:27; Weaver et al., 2003, *J. Neurooncol.*, 65:3; Leamon et al., 1993, *J. Biol. Chem.*, 268:24847; Leamon et al., 1994, *J. Drug Target.*, 2:101; Atkinson et al., 2001, *J. Biol. Chem.*, 276:27930; Frankel et al., 2002, *Clin. Cancer Res.*, 8:1004; Francis et al., 2002, *Br. J. Cancer*, 87:600; de Graaf et al., 2002, *Br. J. Cancer*, 86:811; Spooner et al., 2003, *Br. J. Cancer*, 88:1622; Liu et al., 1999, *J. Drug Target.*, 7:43; Robinson et al., 2004, *Proc. Natl. Acad. Sci., USA*, 101:14527; Sondel et al., 2003, *Curr. Opin. Investig. Drugs*, 4:696; Connor et al., 2004, *J. Immunother.*, 27:211; Gillies et al., 2005, *Blood*, 105:3972; Melani et al., 1998, *Cancer Res.*, 58:4146; Metelitsa et al., 2002, *Blood*, 99:4166; Lyu et al., 2005, *Mol. Cancer Ther.*, 4:1205; and Notter et al., 2001, *Blood*, 97:3138).

In some embodiments, protein targeting moieties can be antibodies. One of ordinary skill in the art will appreciate that any antibody that specifically binds to a desired target can be used in accordance with the present invention.

In some embodiments, antibodies which recognize PSMA can be used to target cells associated with prostate cancer tumors. Such antibodies include, but are not limited to, scFv antibodies A5, G0, G1, G2, and G4 and mAbs 3/E7, 3/F11, 3/A12, K7, K12, and D20 (Elsässer-Beile et al., 2006, *Prostate*, 66:1359); mAbs E99, J591, J533, and J415 (Liu et al., 1997, *Cancer Res.*, 57:3629; Liu et al., 1998, *Cancer Res.*, 58:4055; Fracasso et al., 2002, *Prostate*, 53:9; McDevitt et al., 2000, *Cancer Res.*, 60:6095; McDevitt et al., 2001, *Science*, 294:1537; Smith-Jones et al., 2000, *Cancer Res.*, 60:5237; Vallabhajosula et al., 2004, *Prostate*, 58:145; Bander et al., 2003, *J. Urol.*, 170:1717; Patri et al., 2004, *Bioconj. Chem.*, 15:1174; and U.S. Pat. No. 7,163,680); mAb 7E11-C5.3 (Horoszewicz et al., 1987, *Anticancer Res.*, 7:927); antibody 7E11 (Horoszewicz et al., 1987, *Anticancer Res.*, 7:927; and U.S. Pat. No. 5,162,504); and antibodies described in Chang et al., 1999, *Cancer Res.*, 59:3192; Murphy et al., 1998, *J. Urol.*, 160:2396; Grauer et al., 1998, *Cancer Res.*, 58:4787; and Wang et al., 2001, *Int. J. Cancer*, 92:871. One of ordinary skill in the art will appreciate that any antibody that recognizes and/or specifically binds to PSMA may be used in accordance with the present invention.

In some embodiments, antibodies which recognize other prostate tumor-associated antigens are known in the art and can be used in accordance with the present invention to target cells associated with prostate cancer tumors (see, e.g., Vihko et al., 1985, *Biotechnology in Diagnostics*, 131; Babaian et al., 1987, *J. Urol.*, 137:439; Leroy et al., 1989, *Cancer*, 64:1; Meyers et al., 1989, *Prostate*, 14:209; and U.S. Pat. Nos. 4,970,299; 4,902,615; 4,446,122 and Re 33,405; 4,862,851; 5,055,404). To give but a few examples, antibodies have been identified which recognize transmembrane protein 24P4C12 (U.S. Patent Publication 2005/0019870); calveolin (U.S. Patent Publications 2003/0003103 and 2001/0012890); L6 (U.S. Patent Publication 2004/0156846); prostate specific reductase polypeptide (U.S. Pat. No. 5,786,204; and U.S. Patent Publication 2002/0150578); and prostate stem cell antigen (U.S. Patent Publication 2006/0269557).

In some embodiments, protein targeting moieties that may be used to target cells associated with prostate cancer tumors include conformationally constricted dipeptide mimetics (Ding et al., 2004, *Org. Lett.*, 6:1805).

In some embodiments, a targeting moiety may be an antibody and/or characteristic portion thereof. The term "antibody" refers to any immunoglobulin, whether natural or wholly or partially synthetically produced and to derivatives thereof and characteristic portions thereof. An antibody may be monoclonal or polyclonal. An antibody may be a member of any immunoglobulin class, including any of the human classes: IgG, IgM, IgA, IgD, and IgE.

As used herein, an antibody fragment (i.e. characteristic portion of an antibody) refers to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments.

An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment will typically comprise at least about 50 amino acids and more typically will comprise at least about 200 amino acids.

In some embodiments, antibodies may include chimeric (e.g. "humanized") and single chain (recombinant) antibodies. In some embodiments, antibodies may have reduced effector functions and/or bispecific molecules. In some embodiments, antibodies may include fragments produced by a Fab expression library.

Single-chain Fvs (scFvs) are recombinant antibody fragments consisting of only the variable light chain (VL) and variable heavy chain (VH) covalently connected to one another by a polypeptide linker. Either VL or VH may comprise the NH2-terminal domain. The polypeptide linker may be of variable length and composition so long as the two variable domains are bridged without significant steric interference. Typically, linkers primarily comprise stretches of glycine and serine residues with some glutamic acid or lysine residues interspersed for solubility.

Diabodies are dimeric scFvs. Diabodies typically have shorter peptide linkers than most scFvs, and they often show a preference for associating as dimers.

An Fv fragment is an antibody fragment which consists of one VH and one VL domain held together by noncovalent interactions. The term "dsFv" as used herein refers to an Fv with an engineered intermolecular disulfide bond to stabilize the VH-VL pair.

A F(ab')2 fragment is an antibody fragment essentially equivalent to that obtained from immunoglobulins by digestion with an enzyme pepsin at pH 4.0-4.5. The fragment may be recombinantly produced.

A Fab' fragment is an antibody fragment essentially equivalent to that obtained by reduction of the disulfide bridge or bridges joining the two heavy chain pieces in the F(ab')2 fragment. The Fab' fragment may be recombinantly produced.

A Fab fragment is an antibody fragment essentially equivalent to that obtained by digestion of immunoglobulins with an enzyme (e.g. papain). The Fab fragment may be recombinantly produced. The heavy chain segment of the Fab fragment is the Fd piece.

In some embodiments, targeting moieties can be peptides. One of ordinary skill in the art will appreciate that any peptide that specifically binds to a desired target can be used in accordance with the present invention.

In some embodiments, peptide targeting moieties which target tumor vasculature can be used in accordance with the present invention. In some embodiments, peptides targeting tumor vasculature are antagonists or inhibitors of angiogenic proteins that include VEGFR (Binetruy-Tournaire et al., 2000, *EMBO J.*, 19:1525), CD36 (Reiher et al., 2002, *Int. J. Cancer*, 98:682) integrins $\alpha_v\beta_3$ and $\alpha_v\beta_5$ (Koivunen et al., 1995, *Biotechnology (NY)*, 13:265; and Kumar et al., 2001, *Cancer Res.*, 61:2232) aminopeptidase N (Pasqualini et al., 2000, *Cancer Res.*, 60:722), and matrix metalloproteinases (Koivunen et al., 1999, *Nat. Biotechnol.*, 17:768). For instance, ATWLPPR peptide is a potent antagonist of VEGF (Binetruy-Tournaire et al., 2000, *EMBO J.*, 19:1525); thrombospondin-1 (TSP-1) mimetics can induce apoptosis in endothelial cells (Reiher et al., 2002, *Int. J. Cancer*, 98:682); RGD-motif mimics (e.g. cyclic peptide ACDCRGDCFCG and RGD peptidomimetic SCH 221153) block integrin receptors (Koivunen et al., 1995, *Biotechnology (NY)*, 13:265; and Kumar et al., 2001, *Cancer Res.*, 61:2232); NGR-containing peptides (e.g. cyclic CNGRC) inhibit aminopeptidase N (Pasqualini et al., 2000, *Cancer Res.*, 60:722); and cyclic peptides containing the sequence of HWGF (e.g. CTTHWGFTLC) selectively inhibit MMP-2 and MMP-9 (Koivunen et al., 1999, *Nat. Biotechnol.*, 17:768); and a LyP-1 peptide has been identified (CGNKRTRGC) which specifically binds to tumor lymphatic vessels and induces apoptosis of endothelial cells (Laakkonen et al., 2004, *Proc. Natl. Acad. Sci., USA*, 101: 9381).

In some embodiments, peptide targeting moieties include peptide analogs that block binding of peptide hormones to receptors expressed in human cancers (Bauer et al., 1982, *Life Sci.*, 31:1133). Exemplary hormone receptors (Reubi et al., 2003, *Endocr. Rev.*, 24:389) include (1) somatostatin receptors (e.g. octreotide, vapreotide, and lanretode) (Froidevaux et al., 2002, *Biopolymers*, 66:161); (2) bombesin/gastrin-releasing peptide (GRP) receptor (e.g. RC-3940 series) (Kanashiro et al., 2003, *Proc. Natl. Acad. Sci., USA*, 100:15836); and (3) LHRH receptor (e.g. Decapeptyl®, Lupron®, Zoladex®, and Cetrorelix®) (Schally et al., 2000, *Prostate*, 45:158).

In some embodiments, peptides which recognize IL-11 receptor-α can be used to target cells associated with prostate cancer tumors (see, e.g. U.S. Patent Publication 2005/0191294).

Carbohydrate Targeting Moieties

In some embodiments, a targeting moiety in accordance with the present invention may comprise a carbohydrate. To give but one example, lactose and/or galactose can be used for targeting hepatocytes.

In some embodiments, a carbohydrate may be a polysaccharide comprising simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, the carbohydrate may be aminated, carboxylated, and/or sulfated. In some embodiments, hydrophilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

Lipid Targeting Moieties

In some embodiments, a targeting moiety in accordance with the present invention may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be a $C_{15}$-$C_{25}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

Surfactant

In some embodiments, fluid streams may optionally comprise one or more surfactants. A surfactant may be mixed with a solvent, non-solvent, and/or other component of a particle. In some embodiments, a surfactant can promote the production of particles with increased stability, improved uniformity, or increased viscosity. The percent of surfactant in particles produced by inventive microfluidic systems can range from 0% to 99% by weight, from 10% to 99% by weight, from 25% to 99% by weight, from 50% to 99% by weight, or from 75% to 99% by weight. In some embodiments, the percent of surfactant in produced particles can range from 0% to 75% by weight, from 0% to 50% by weight, from 0% to 25% by weight, or from 0% to 10% by weight. In some embodiments, the percent of surfactant in produced particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Any surfactant known in the art may be included in fluid streams in accordance with the present invention. Such surfactants include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span® 85) glycocholate; sorbitan monolaurate (Span® 20); polysorbate 20 (Tween®-20); polysorbate 60 (Tween®-60); polysorbate 65 (Tween®-65); polysorbate 80 (Tween®-80); polysorbate 85 (Tween®-85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; Pluronic® (block copolymers based on ethylene oxide and propylene oxide); and combinations thereof. The surfactant component may be a mixture of different surfactants. These surfactants may be extracted and purified from a natural source or may be prepared synthetically in a laboratory. In certain specific embodiments, surfactants are commercially available.

Those skilled in the art will recognize that this is an exemplary, not comprehensive, list of substances with surfactant activity. Any surfactant may be used in the production of particles to be used in accordance with the present invention.

Other Components

In some embodiments, fluid streams may optionally comprise one or more other components. For example, fluid streams may optionally comprise buffering agents (Tris, HEPES, MES, PIPES, MOPS, TES, etc.), salts (e.g. NaCl, KCl, $CaCl_2$, $NaPO_4$, $Na_2PO_4$, $MgCl_2$, $MgSO_4$, etc.), polymers (e.g., PEG), surfactants, lipids, acids, bases, etc.

Particles Produced Using Microfluidic Systems

In general, inventive microfluidic systems may be used to produce particles having a greatest dimension (e.g. diameter) of less than 100 microns (μm). In some embodiments, produced particles have a greatest dimension of less than 10 μm. In some embodiments, produced particles have a greatest dimension of less than 1000 nanometers (nm). In some embodiments, produced particles have a greatest dimension of less than 900 nm, 800 nm, 700 nm, 600 nm, 500 nm, 400 nm, 300 nm, 200 nm, or 100 nm. Typically, produced particles have a greatest dimension (e.g., diameter) of 300 nm or less. In some embodiments, produced particles have a greatest dimension (e.g. diameter) of 250 nm or less. In some embodiments, produced particles have a greatest dimension (e.g., diameter) of 200 nm or less. In some embodiments, produced particles have a greatest dimension (e.g., diameter) of 150 nm or less. In some embodiments, produced particles have a greatest dimension (e.g., diameter) of 100 nm or less. Smaller particles, e.g., having a greatest dimension of 50 nm or less, 40 nm or less, 30 nm or less, 20 nm or less, 10 nm or less, or 5 nm or less are produced in some embodiments of the invention. In some embodiments, produced particles have a greatest dimension ranging between 5 nm and 200 nm. In some embodiments, produced particles have a greatest dimension ranging between 5 nm and 100 nm. In specific embodiments, produced particles have a greatest dimension ranging between 5 nm and 50 nm. In certain specific embodiments, produced particles have a greatest dimension ranging between 10 nm and 40 nm. In certain specific embodiments, produced particles have a greatest dimension ranging between 15 nm and 35 nm.

In some embodiments, produced particles have a diameter of approximately 1000 nm. In some embodiments, produced particles have a diameter of approximately 750 nm. In some embodiments, produced particles have a diameter of approximately 500 nm. In some embodiments, produced particles have a diameter of approximately 450 nm. In some embodiments, produced particles have a diameter of approximately 400 nm. In some embodiments, produced particles have a diameter of approximately 350 nm. In some embodiments, produced particles have a diameter of approximately 300 nm. In some embodiments, produced particles have a diameter of approximately 275 nm. In some embodiments, produced particles have a diameter of approximately 250 nm. In some embodiments, produced particles have a diameter of approximately 225 nm. In some embodiments, particles have a diameter of approximately 200 nm. In some embodiments, produced particles have a diameter of approximately 175 nm. In some embodiments, produced particles have a diameter of approximately 150 nm. In some embodiments, produced particles have a diameter of approximately 125 nm. In some embodiments, produced particles have a diameter of approximately 100 nm. In some embodiments, produced particles have a diameter of approximately 75 nm. In some embodiments, produced particles have a diameter of approximately 50 nm. In some embodiments, produced particles have a diameter of approximately 45 nm. In some embodiments, produced particles have a diameter of approximately 40 nm. In some embodiments, produced particles have a diameter of approximately 35 nm. In some embodiments, produced particles have a diameter of approximately 30 nm. In some embodiments, produced particles have a diameter of approximately 25 nm. In some embodiments, produced particles have a diameter of approximately 20 nm. In some embodiments, produced particles have a diameter of approximately 10 nm. In some embodiments, produced particles have a diameter of approximately 5 nm.

In some embodiments, produced particles have a diameter of less than 1000 nm. In some embodiments, produced particles have a diameter of less than 750 nm. In some embodiments, produced particles have a diameter of less than 500 nm. In some embodiments, produced particles have a diameter of less than 450 nm. In some embodiments, produced particles have a diameter of less than 400 nm. In some embodiments, produced particles have a diameter of less than 350 nm. In some embodiments, produced particles have a diameter of less than 300 nm. In some embodiments, produced particles have a diameter of less than 275 nm. In some embodiments, produced particles have a diameter of less than 250 nm. In some embodiments, produced particles have a diameter of less than 225 nm. In some embodiments, particles have a diameter of less than 200 nm. In some embodiments, produced particles have a diameter of less than 175 nm. In some embodiments, produced particles have a diameter of less than 150 nm. In some embodiments, produced particles have a diameter of less than 125 nm. In some embodiments, produced particles have a diameter of less than 100 nm. In some embodiments, produced particles have a diameter of less than 75 nm. In some embodiments, produced particles have a diameter of less than 50 nm. In some embodiments, produced particles have a diameter of less than 40 nm. In some embodiments, produced particles have a diameter of less than 30 nm. In some embodiments, produced particles have a diameter of less than 20 nm. In some embodiments, produced particles have a diameter of less than 10 nm. In some embodiments, produced particles have a diameter of less than 5 nm.

Populations of particles produced using inventive microfluidic systems are characterized by a mean particle diameter. In some embodiments, mean particle diameter is measured by particle weight. In some embodiments, mean particle diameter is measured by the total number of particles. In some embodiments, the diameter of no more than 1% of the produced particles varies from the mean particle diameter by more than 150% of the mean particle diameter. In some embodiments, the diameter of no more than 1% of the produced particles varies from the mean particle diameter by more than 100% of the mean particle diameter. In some embodiments, the diameter of no more than 1% of the produced particles varies from the mean particle diameter by more than 75% of the mean particle diameter. In some embodiments, the diameter of no more than 1% of the produced particles varies from the mean particle diameter by more than 50% of the mean particle diameter. In some embodiments, the diameter of no more than 1% of the produced particles varies from the mean particle diamter by more than 25% of the mean particle diameter.

In some embodiments, no more than 5% of the produced particles varies by more than 150% of the mean particle diameter. In some embodiments, no more than 5% of the produced particles varies by more than 100% of the mean particle diameter. In some embodiments, no more than 5% of the produced particles varies by more than 75% of the mean particle diameter. In some embodiments, no more than 5% of the produced particles varies by more than 50% of the mean particle diameter. In some embodiments, no more than 5% of the produced particles varies by more than 25% of the mean particle diameter.

In some embodiments, no more than 10% of the produced particles varies by more than 150% of the mean particle diameter. In some embodiments, no more than 10% of the produced particles varies by more than 100% of the mean particle diameter. In some embodiments, no more than 10% of the produced particles varies by more than 75% of the mean particle diameter. In some embodiments, no more than 10% of the produced particles varies by more than 50% of the mean particle diameter. In some embodiments, no more than 10% of the produced particles varies by more than 25% of the mean particle diameter.

In some embodiments, no more than 25% of the produced particles varies by more than 150% of the mean particle diameter. In some embodiments, no more than 25% of the produced particles varies by more than 100% of the mean particle diameter. In some embodiments, no more than 25% of the produced particles varies by more than 75% of the mean particle diameter. In certain embodiments, no more than 25% of the produced particles varies by more than 50% of the mean particle diameter. In some embodiments, no more than 25% of the produced particles varies by more than 25% of the mean particle diameter.

In some embodiments, the diameter of any individual particle varies by no more than 25% of the mean particle diameter of the particle population. In some embodiments, the diameter of any individual particle varies by no more than 50% of the mean particle diameter of the particle population. In some embodiments, the diameter of any individual particle varies by no more than 75% of the mean particle diameter of the particle population. In some embodiments, the diameter of any individual particle varies by no more than 100% of the mean particle diameter of the particle population. In some embodiments, the diameter of any individual particle varies by no more than 150% of the mean particle diameter of the particle population. In some embodiments, the diameter of any individual particle varies by no more than 200% of the mean particle diameter of the particle population.

In some embodiments, the diameter of approximately 10% of the particles varies by no more than 50% above the mean particle diameter, and wherein the diameter of approximately 10% of the particles varies by no more than 50% below the mean particle diameter. In some embodiments, the diameter of approximately 10% of the particles varies by no more than 25% above the mean particle diameter, and wherein the diameter of approximately 10% of the particles varies by no more than 25% below the mean particle diameter. In some embodiments, the diameter of approximately 10% of the particles varies by no more than 10% above the mean particle diameter, and wherein the diameter of approximately 10% of the particles varies by no more than 10% below the mean particle diameter.

In certain embodiments, produced particles are greater in size than the renal excretion limit (e.g. particles having diameters of greater than 6 nm). In specific embodiments, produced particles have diameters greater than 5 nm, greater than 10 nm, greater than 15 nm, greater than 20 nm, greater than 50 nm, greater than 100 nm, greater than 250 nm, greater than 500 nm, greater than 1000 nm, or larger. In certain embodiments, produced particles are small enough to avoid clearance of particles from the bloodstream by the liver (e.g. particles having diameters of less than 1000 nm). In specific embodiments, produced particles have diameters less than 1500 nm, less than 1000 nm, less than 750 nm, less than 500 nm, less than 250 nm, less than 100 nm, or smaller. In general, physiochemical features of particles, including particle size, can be selected to allow a particle to circulate longer in plasma by decreasing renal excretion and/or liver clearance. In some embodiments, produced particles have diameters ranging from 5 nm to 1500 nm, from 5 nm to 1000 nm, from 5 nm to 750 nm, from 5 nm to 500 nm, from 5 nm to 250 nm, or from 5 nm to 100 nm. In some embodiments, produced particles have diameters ranging from 10 nm to 1500 nm, from 15 nm to 1500 nm, from 20 nm to 1500 nm, from 50 nm to 1500 nm, from 100 nm to 1500 nm, from 250 nm to 1500 nm, from 500 nm to 1500 nm, or from 1000 nm to 1500 nm.

It is often desirable to produce a population of particles that is relatively uniform in terms of size, shape, and/or composition so that each particle has similar properties. For example, at least 80%, at least 90%, or at least 95% of the particles produced using inventive microfluidic systems may have a diameter or greatest dimension that falls within 5%, 10%, or 20% of the average diameter or greatest dimension. In some embodiments, a population of particles may be heterogeneous with respect to size, shape, and/or composition.

Zeta potential is a measurement of surface potential of a particle. The zeta potential of particle is a contributing factor to particle biodistribution and cellular uptake. In some embodiments, produced particles have a zeta potential ranging between −300 mV and +300 mV. In some embodiments, produced particles have a zeta potential ranging between −250 mV and +250 mV. In some embodiments, produced particles have a zeta potential ranging between −200 mV and +200 mV. In some embodiments, produced particles have a zeta potential ranging between −150 mV and +150 mV. In some embodiments, produced particles have a zeta potential ranging between −100 mV and +100 mV. In some embodiments, produced particles have a zeta potential ranging between −50 mV and +50 mV. In some embodiments, produced particles have a zeta potential ranging between −25 mV and +25 mV. In some embodiments, produced particles have a zeta potential ranging between −10 mV and +10 mV. In some embodiments, produced particles have a zeta potential ranging between −5 mV and +5 mV. In some embodiments, produced particles have a substantially neutral zeta potential (i.e. approximately 0 mV).

In some embodiments, produced particles have a negative zeta potential. In some embodiments, produced particles have a zeta potential ranging between −300 mV and 0 mV. In some embodiments, produced particles have a zeta potential ranging between −250 mV and 0 mV. In some embodiments, produced particles have a zeta potential ranging between −200 mV and 0 mV. In some embodiments, produced particles have a zeta potential ranging between −150 mV and 0 mV. In some embodiments, produced particles have a zeta potential ranging between −100 mV and 0 mV. In some embodiments, produced particles have a zeta potential ranging between −95 mV and 0 mV. In some embodiments, produced particles have a zeta potential ranging between −90 mV and 0 mV. In some embodiments, produced particles have a zeta potential ranging between −85 mV and 0 mV. In some embodiments, produced particles have a zeta potential ranging between −80 mV and 0 mV. In some embodiments, produced particles have a zeta potential ranging between −75 mV and 0 mV. In some embodiments, produced particles have a zeta potential ranging between −70 mV and 0 mV. In some embodiments, produced particles have a zeta potential ranging between −65 mV and 0 mV. In some embodiments, produced particles have a zeta potential ranging between −60 mV and 0 mV. In some embodiments, produced particles have a zeta potential ranging between −55 mV and 0 mV. In some embodiments, produced particles have a zeta potential ranging between −50 mV and 0 mV. In some embodiments, produced particles have a zeta potential ranging between −45 mV and 0 mV. In some embodiments, produced particles have a zeta potential ranging between −40 mV and 0 mV. In some embodiments, produced particles have a zeta potential ranging between −30 mV and 0 mV. In some embodiments, produced particles have a zeta potential ranging between −25 mV and 0 mV. In some embodiments, produced particles have a zeta potential ranging between −20 mV and 0 mV. In some embodiments, produced particles have a zeta potential ranging between −15 mV and 0 mV. In some embodiments, produced particles have a zeta potential ranging between −10 mV and 0 mV. In some embodiments, produced particles have a zeta potential ranging between −5 mV and 0 mV.

In some embodiments, produced particles have a zeta potential ranging between −50 mV and −5 mV. In some embodiments, produced particles have a zeta potential ranging between −50 mV and −10 mV. In some embodiments, produced particles have a zeta potential ranging between −50 mV and −15 mV. In some embodiments, produced particles have a zeta potential ranging between −50 mV and −20 mV. In some embodiments, produced particles have a zeta potential ranging between −25 mV and −30 mV. In some embodiments, produced particles have a zeta potential ranging between −50 mV and −35 mV. In some embodiments, produced particles have a zeta potential ranging between −50 mV and −40 mV. In some embodiments, produced particles have a zeta potential ranging between −50 mV and −45 mV.

In some embodiments, produced particles have a positive zeta potential. In some embodiments, produced particles have a zeta potential ranging between 0 mV and +50 mV. In some embodiments, produced particles have a zeta potential ranging between 0 mV and +25 mV. In some embodiments, produced particles have a zeta potential ranging between 0 mV and +10 mV. In some embodiments, produced particles have a zeta potential ranging between 0 mV and +5 mV.

In some embodiments, produced particles are spheres or spheroids. In some embodiments, produced particles are flat or plate-shaped. In some embodiments, produced particles are cubes or cuboids. In some embodiments, produced particles are ovals or ellipses. In some embodiments, produced particles are cylinders, cones, or pyramids.

In some embodiments, particles produced using inventive microfluidic systems are microparticles (e.g. microspheres). In general, a "microparticle" refers to any particle having a diameter of less than 1000 μm. In some embodiments, produced particles are nanoparticles (e.g. nanospheres). In general, a "nanoparticle" refers to any particle having a diameter of less than 1000 nm. In some embodiments, produced particles are picoparticles (e.g. picospheres). In general, a "picoparticle" refers to any particle having a diameter of less than 1 nm. In some embodiments, produced particles are liposomes. In some embodiments, produced particles are micelles.

Particles produced by inventive microfludic systems can be solid or hollow and can comprise one or more layers (e.g. nanoshells, nanorings). In some embodiments, each layer has a unique composition and unique properties relative to the other layer(s). To give but one example, particles may have a core/shell structure, wherein the core is one layer and the shell is a second layer. Particles may comprise a plurality of different layers. In some embodiments, one layer may be substantially cross-linked, a second layer is not substantially cross-linked, and so forth. In some embodiments, cross-linking may involve a separate cross-linking step. In some embodiments, one, a few, or all of the different layers may comprise one or more therapeutic agents. In some embodiments, one layer comprises a therapeutic agent, a second layer does not comprise a therapeutic agent, and so forth. In some embodiments, each individual layer comprises a different agent or set of therapeutic agents.

In certain embodiments of the invention, produced particles are porous, by which is meant that the particles contain holes or channels, which are typically small compared with the size of the particle. In some embodiments, produced particles are not porous.

Particles produced using inventive microfluidic systems may have a coating layer. Use of a biocompatible coating layer can be advantageous, e.g. if the particles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, other nanoparticles that can be associated with inventive nanoparticles etc. Coatings may be applied after particle production or assembled in a variety of ways such as by dipping, using a layer-by-layer technique, conjugation, etc. In some embodiments, coatings may be applied to a particle by self-assembly. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties.

In some embodiments, particles produced using inventive microfluidic systems are biodegradable and biocompatible. In general, a biocompatible substance is not toxic to cells. In some embodiments, a substance is considered to be biocompatible if its addition to cells results in less than a certain threshhold of cell death. In some embodiments, a substance is considered to be biocompatible if its addition to cells does not induce adverse effects. In general, a biodegradable substance is one that undergoes breakdown under physiological conditions over the course of a therapeutically relevant time period (e.g. weeks, months, or years). In some embodiments, a biodegradable substance is a substance that can be broken down by cellular machinery. In some embodiments, a biodegradable substance is a substance that can be broken down by chemical processes. In some embodiments, a particle comprises a polymer, solvent, therapeutic agent, targeting moiety, and/or surfactant that is biocompatible and biodegradable. In some embodiments, a particle comprises a polymer, solvent, therapeutic agent, targeting moiety, and/or surfactant that is biocompatible, but not biodegradable. In some embodiments, a particle comprises a polymer, solvent, therapeutic agent, targeting moiety, and/or surfactant that is biodegradable, but not biocompatible. In some embodiments, a particle comprises a polymer, solvent, therapeutic agent, targeting moiety, and/or surfactant that is neither biodegradable nor biocompatible. In some embodiments, a particle comprises a polymer, solvent, targeting moiety, and/or surfactant that is biodegradable and/or biocompatible and a therapeutic agent that is not biodegradable and/or biocompatible.

Methods of Modifying Particle Characteristics

The present invention encompasses the recognition that there are many parameters that can be varied in order to change the properties of the resulting particles (see, e.g. Chacon et al., 1996, *Int'l J. Pharmaceutics*, 141:81). For example, polymer concentration, mixing conditions, and solvent to water ratio affect particle size. Other parameters such as receptor density and type of passivation—typically PEG with branched, unbranched, charged, uncharged chains—can also determine the pharmacokinetics and targeting efficiency of resulting particles. Examples 3-5 present examples of various ways in which adjusting particle production parameters can affect the characteristics of produced particles.

Microfluidic systems provided by the present invention are useful for engineering particles that have specific characteristics (e.g. polymer composition, therapeutic agent composition, particle size, particle charge, etc.). By adjusting any of the parameters described herein (e.g. flow rate, channel size, mixing apparatus size, polymer selection and concentration, solvent and non-solvent selection concentration, therapeutic agent selection and concentration, surfactant, targeting moiety, mixing time, etc.), particles having specific or desirable characteristics can be engineered.

In some embodiments, the characteristics of the particles may be modified by adjusting the composition of at least one fluid stream (e.g. polymeric stream, non-solvent stream, and/or inlet stream). In some embodiments, the characteristics of the particles may be modified by adjusting the concentration of polymer in the polymeric solution (see, e.g. Example 4).

In some embodiments, the characteristics of the particles may be modified by adjusting the concentration of a therapeutic agent in the polymeric stream or in the non-solvent stream.

In some embodiments, the characteristics of the particles may be modified by adjusting the concentration of a targeting moiety in the polymeric stream or in the non-solvent stream. In general, these concentrations fall within solubility limits. In some embodiments, the concentration of a targeting moiety in the polymeric stream or in the non-solvent stream ranges from 0.1 mg/ml to 100 mg/ml. In some embodiments, the concentration of a targeting moiety in the polymeric stream or in the non-solvent stream is approximately 0.1 mg/ml, approximately 1.0 mg/ml, approximately 10 mg/ml, or approximately 100 mg/ml.

In some embodiments, the characteristics of the particles may be modified by adjusting the non-solvent to solvent ratio of the fluid in the mixing apparatus. In some embodiments, the non-solvent to solvent ratio of the fluid in the mixing apparatus can be controlled by adjusting the flow rates of the polymeric stream(s) and the non-solvent stream(s). In some embodiments, the solvent to non-solvent ratio ranges from 10:1 to 1:30. In some embodiments, the solvent to non-solvent ratio is approximately 10:1, approximately 5:1, approximately 1:1, approximately 1:5, approximately 1:10, approximately 1:15, approximately 1:20, approximately 1:25, or approximately 1:30. In some embodiments, the solvent to non-solvent ratio can be greater than 10:1 or smaller than 1:30. In specific embodiments, the solvent to non-solvent ratio is approximately 1:20. In general, for hydrodynamic focusing, a larger ratio of solvent flow rate to non-solvent flow rate may yield particles that are more monodispersed than particles produced by a smaller ratio of solvent flow rate to non-solvent flow rate (see, e.g., Example 3).

In some embodiments, the characteristics of the particles may be modified by adjusting the flow rate of at least one fluid stream (e.g. polymeric stream, non-solvent stream, and/or inlet stream). In certain embodiments, the flow rate of a fluid stream may be zero. In some embodiments, the flow rate may range from 0.001 μl/min to 1.0 ml/min. In some embodiments, the flow rate is approximately 0.01 μl/min, approximately 0.1 μl/min, approximately 0.5 μl/min, approximately 1.0 μl/min, approximately 5 μl/min, approximately 10 μl/min, approximately 50 μl/min, approximately 100 μl/min, or approximately 1.0 ml/min. In specific embodiments, the flow rate is approximately 10 μl/min for aqueous solutions (e.g. a non-solvent such as water). In specific embodiments, the flow rate is approximately 0.5 μl/min for polymeric solutions. In some embodiments, adjusting the flow rate of one or more of the streams containing a component of the particle and/or the polymeric stream results in modifying the composition of the fluid in the mixing apparatus.

In some embodiments, adjusting the mixing time of the streams results in modifying the composition of the fluid in the mixing apparatus. In general, slower mixing times may yield particles that are larger and more monodispersed than particles produced by faster mixing.

In some embodiments, including more than one polymer (e.g. including PLGA and PLGA-PEG) in the polymeric solution may yield particles that are larger than, smaller than, or the same size as particles produced in the presence of only one polymer (see, e.g., Example 5).

As discussed herein, various parameters such as polymer concentration, therapeutic agent concentration, excipient concentration, mixing conditions, solvent identity, solvent to water ratio, surfactant, temperature, etc. can affect particle characteristics (e.g. composition, size, charge, etc.). The present invention encompasses the recognition that microfluidics may provide a way to optimize these properties by enabling large-scale combinatorial screening of conditions and by providing insight into how different parameters affect the resulting particle. Two ways in which combinatorial synthesis may be achieved are serial and parallel combinatorial syntheses (deMello, 2006, *Nature*, 442:394). Serial combinatorial synthesis is suitable for screening reactions that occur on relatively short timescales, since short timescales enable many different reaction conditions to be screened serially in a relatively manageable timescale. The present invention encompasses the recognition that conditions (e.g. solvent to water ratio, polymer concentration, drug concentration, rate of mixing, temperature, etc.) can be varied in real time in microfluidic synthesis and that a large parameter space may be explored using small samples and in an automated setup.

In some embodiments, multiple preparations of particles with varying conditions are performed sequentially. In some embodiments, at least 5 preparations, at least 10 preparations, at least 25 preparations, at least 50 preparations, at least 100 preparations, at least 500 preparations, at least 1000 preparations, at least 500 preparations, or more preparations are performed sequentially.

The present invention provides methods for scaling up nanoparticle synthesis comprising multiple inventive microfluidic devices operating in parallel (e.g. parallel scale-out; deMello, 2006, *Nature*, 442:394). These parallel reactors can enable precise control over reaction conditions yielding high-quality nanoparticles; at the same time they would produce enough nanoparticles (~g/hr quantities) to be useful in the context of industrial scale synthesis. An exemplary system for nanoparticle synthesis comprising multiple inventive microfluidic devices operating in parallel is shown in FIG. 6. In some embodiments, at least 5 devices, at least 10 devices, at least 25 devices, at least 50 devices, at least 100 devices, at least 500 devices, at least 1000 devices, at least 5000 devices, or more devices can be operating in parallel.

Another way of increasing the throughput of each microfluidic device is by appropriately scaling up the capacity of one device. For example, with metal structures, high throughput may be achieved by increasing the flow rate and using an appropriate mixer. A variety of mixer designs (Nguyen and Wu, 2005, *J. Micromechan. Microeng.*, 15:R1) are available for operation in different flow regimes ranging from low throughput low Reynolds number flows to high throughput high Reynolds number flows, as described in more detail above.

The present invention provides methods in which composition of the polymeric stream or non-solvent streams is changed in order to vary nanoprecipitation conditions and characteristics of the produced nanoparticles. This can be done in a serial combinatorial fashion by adding multiple inlet streams that converge together and mix and are subsequently used as the polymeric stream, as described above. The mixing element may be a microfluidic channel, or some other microfluidic mixing element, as described in further detail above. By controlling the flow rates of each inlet stream, the composition of the polymeric stream can be changed. Similarly, the composition of the non-solvent streams may be adjusted. FIGS. 4 and 5 present a design for a microfluidic device that mixes three inlet streams, and uses the resulting stream as the polymeric stream for nanoprecipitation using hydrodynamic flow focusing.

Figure 7:
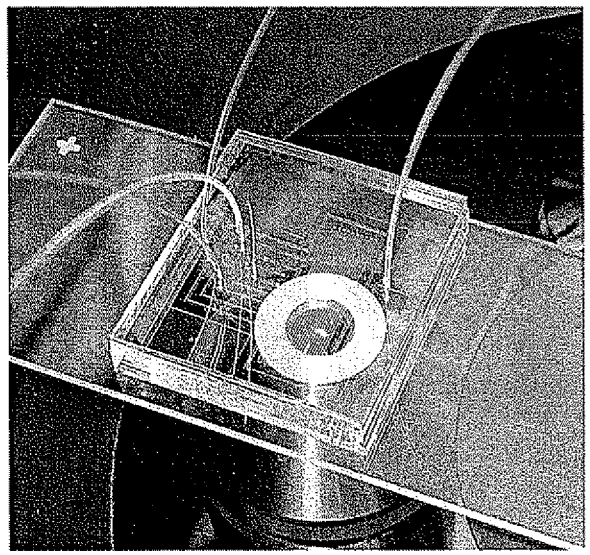
FIG. 7: An exemplary microfluidic device for mixing three precursor streams and subsequently mixing the resulting stream with a water stream for nanoprecipitation.

FIG. 7 illustrates a realization of the concept of combinatorial synthesis in FIGS. 4 and 5. The microfluidic chip has three precursor stream inlets, one water inlet, and one outlet. Two precursor streams were used-PLGA-PEG at 50 mg/ml and acetonitrile. By varying the flow ratios of these two streams, the polymer concentration was varied. Nanoparticles were synthesized in one experiment sequentially by simply varying the flow rates and collecting nanoparticles in different cuvettes. Adding multiple inlet streams and varying the mixing parameters is an extension of this setup contemplated by the present invention. Such methods can be used to produce libraries of particles having a spectrum of characteristics.

EXEMPLIFICATION

The following examples are only intended to provide illustrations of specific embodiments contemplated by the present invention. The examples are not intended in any way to be limiting.

Example 1

Fabrication of a Microfluidic Device

Two methods were employed in order to fabricate microfluidic devices. In the first method, a photocurable epoxy (SU-8, Microchem Inc.) was spun onto a glass (pyrex) wafer to a thickness of 40 μm-100 μm. After standard lithography procedures, microchannels were obtained on the wafer. Holes were drilled in the wafer and another wafer was bonded to the first wafer to form enclosed microchannels. Connections were made from syringes to the device using tubing and sealing the tubing to the device using epoxy. This device had microchannels made of glass and SU-8.

In the second method, standard procedures of soft lithography were used to make the devices from polydimethylsiloxane (PDMS). The device was obtained by first making a master mold using SU-8 lithography followed by silane treatment. PDMS pre-polymer and curing agent (Sylgard 184, Dow Corning) were mixed in the ratio prescribed by the manufacturer, poured on the master mold and cured. PDMS was peeled off, holes were drilled, and it was bonded to a glass slide using oxygen plasma treatment in order to obtain microfluidic devices.

Example 2

Synthesis of PLGA-PEG Nanoparticles in a Microfluidic Device

Figure 8:
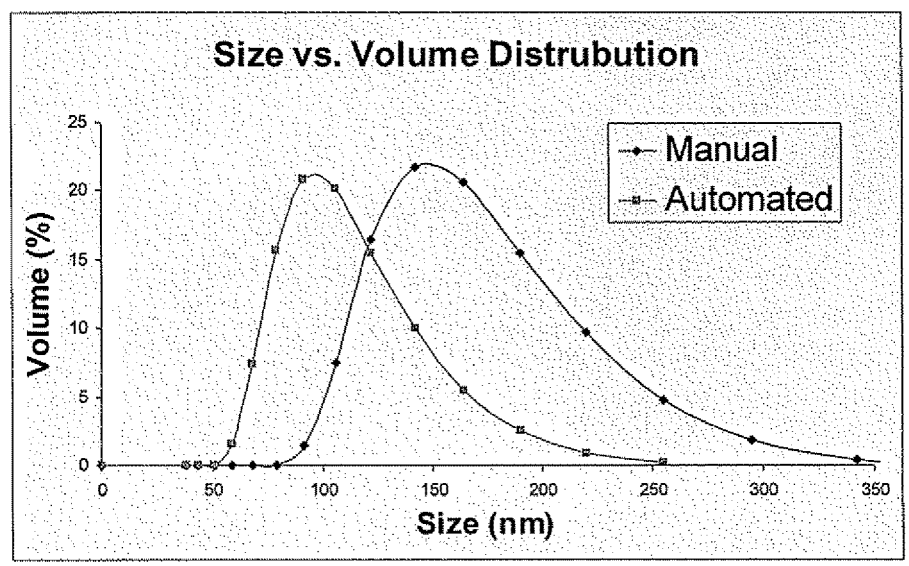
FIG. 8: Comparison of nanoparticles synthesized manually and those synthesized using automated hydrodynamic flow focusing in a microfluidic device.

PLGA-PEG nanoparticles were synthesized by nanoprecipitation using the devices described in Example 1. 50 mg/ml PLGA-PEG solution in acetonitrile was injected in the polymeric stream using a syringe pump at varying flow rates. The outer two streams were water. Nanoparticles that were formed in the microfluidic device were collected and characterized in a Zeta-PALS system. As a control, the same amount of nanoparticles was formed by adding the same amount of polymeric solution into the same quantity of water by hand using a pipette. FIG. 8 shows nanoparticle distributions for nanoparticles formed using the microfluidic device and the nanoparticles synthesized manually. It is seen that the nanoparticles synthesized using the microfluidic device are highly monodisperse in size as compared to those synthesized manually. Without wishing to be bound by any one theory, this may be due to the highly controlled nanoprecipitation in the microfluidic device using hydrodynamic flow focusing.

Example 3

Effect of Flow Ratio on Nanoparticle Size

Figure 9:
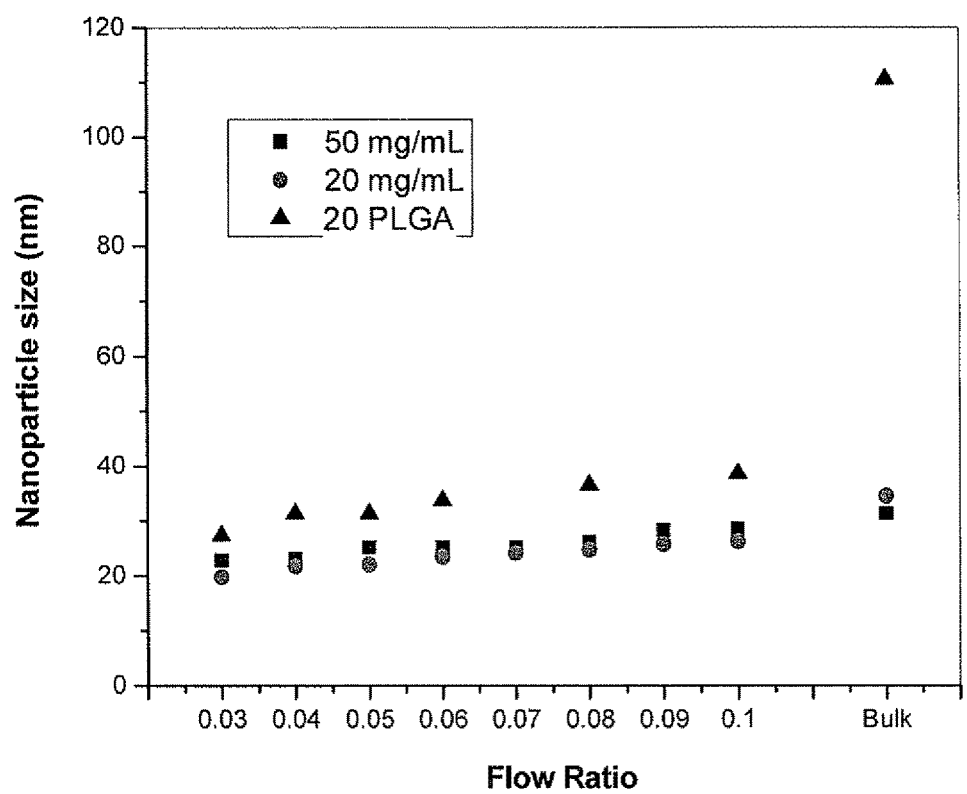
FIG. 9: Effect of flow ratio on nanoparticle size. Increasing the flow ratio (polymeric solution flow rate as a fraction of water flow rate) results in increase of mixing time and increase of the size of produced nanoparticles. Three polymeric solutions—PLGA-PEG in acetonitrile (square), PLGA-PEG in acetonitrile (circle), and a mixture of PLGA-PEG and PLGA (triangles)—exhibit the same trend. Nanoparticles prepared by bulk nanoprecipitation are consistently larger than those prepared using microfluidics. This effect is increased for 20% PLGA, where the nanoparticles prepared using bulk method are nearly three times larger than those prepared using microfluidics.

The term "flow ratio" refers to the polymeric solution flow rate as a fraction of water flow rate. Increasing the flow ratio results in increase of mixing time and increase of the size of produced particles. Three polymeric solutions—50 mg/mL PLGA-PEG in acetonitrile, 20 mg/mL PLGA-PEG in acetonitrile, and a mixture of 40 mg/mL PLGA-PEG and 10 mg/mL PLGA (20% PLGA)—exhibit the same trend (FIG. 9). PLGA-PEG copolymer consisted of ~74 kDa PLGA block and ~3.4 kDa PEG block, while PLGA was ~74 kDa. Water flow rate was maintained at 10 µl/min.

Nanoparticles that were prepared by addition of 3 µl polymeric solution to 60 µl using a pipette (Bulk) are seen to be consistently larger than those prepared using microfluidics. However, this effect is dramatically increased for 20% PLGA, where the nanoparticles prepared using bulk method are nearly three times larger than those prepared using microfluidics (FIG. 9). Volume-averaged particle size was measured using dynamic light scattering (Malvern Zetasizer Nano ZS, Malvern Instruments).

Example 4

Effect of Polymeric Solution Composition on Nanoparticle Size

Figure 10:
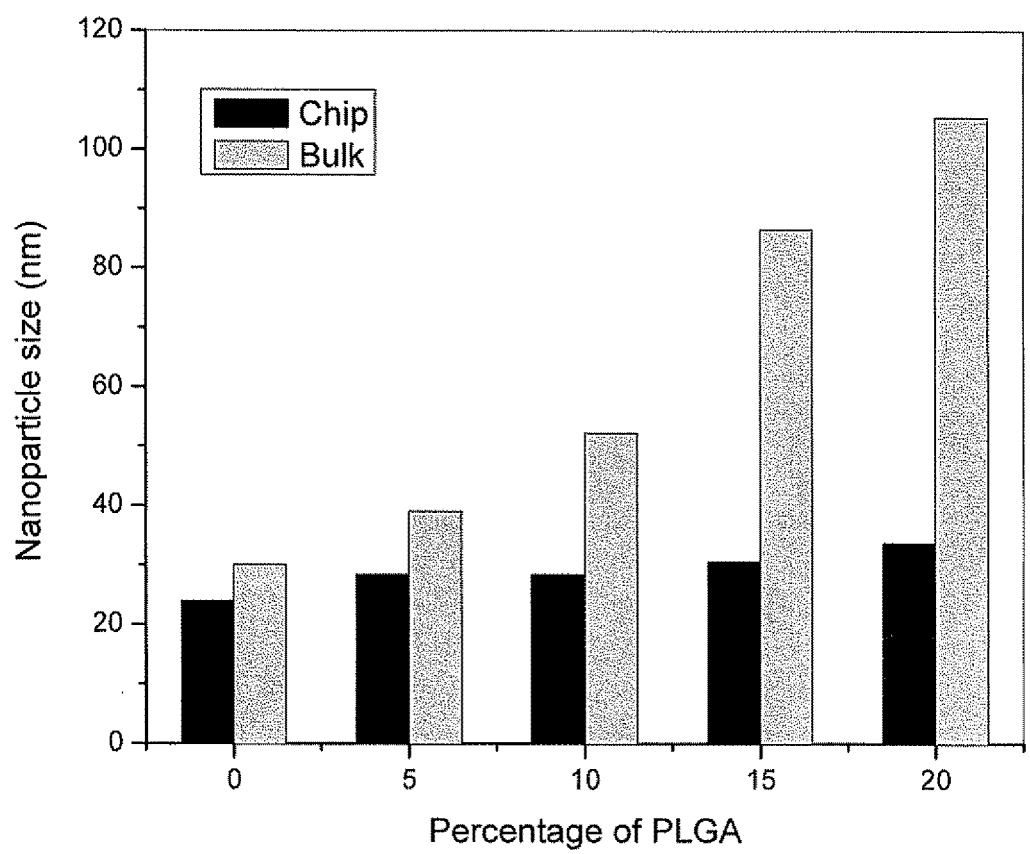
FIG. 10: Effect of polymeric solution composition on nanoparticle size. Polymeric solutions containing different percentages of PLGA and PLGA-PEG were precipitated using hydrodynamic focusing and in bulk. Nanoparticles prepared using bulk method are consistently larger than those prepared using microfluidics.
Figure 11:
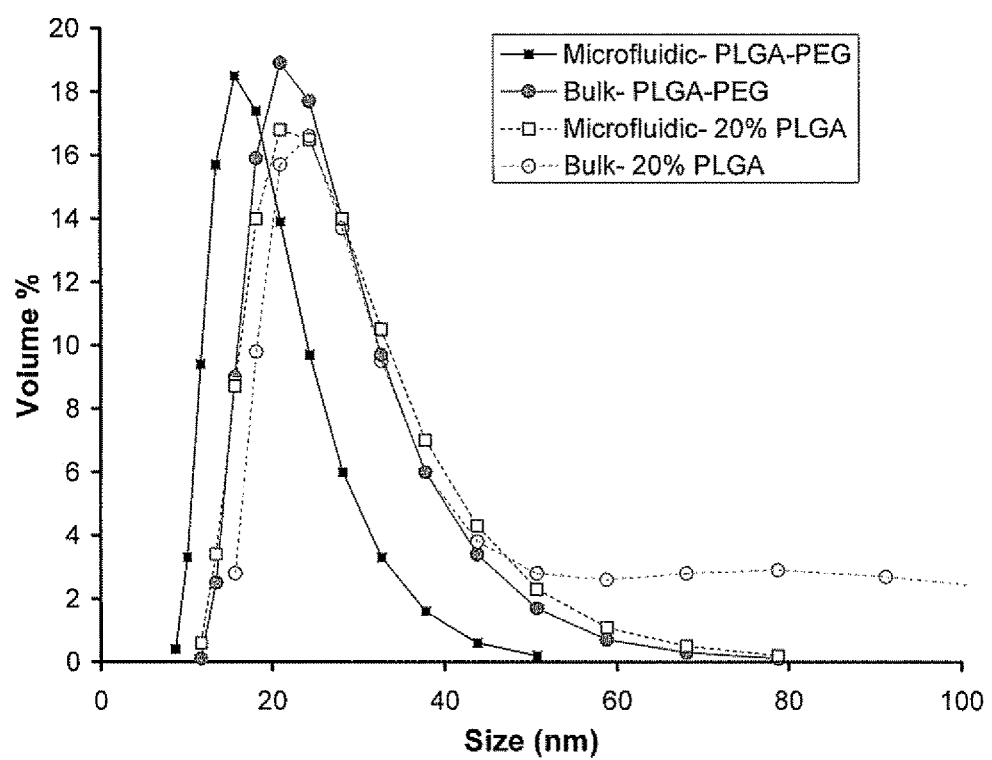
FIG. 11: Size distributions of produced particles. Size distributions for particles produced by microfluidics and by nanoprecipitation in bulk were measured. For PLGA-PEG nanoparticles, microfluidic method results in smaller particle size and narrower distribution. For 20% PLGA nanoparticles, bulk synthesis yields a long "tail" of larger nanoparticles that is absent in microfluidic synthesis.

Polymeric solutions containing different percentages of PLGA and PLGA-PEG were precipitated using hydrodynamic focusing and precipitated in bulk. Total polymeric concentration was 50 mg/ml (10% PLGA solution had 5 mg/ml PLGA and 45 mg/ml PLGA-PEG). Flow rates for hydrodynamic focusing were 10 µl/min (water, a non-solvent) and 0.5 µl/min (polymeric solution in acetonitrile). For bulk samples, 3 µl of polymeric solution was added to 60 µl of water. Volume-averaged particle size was measured using dynamic light scattering (Malvern Zetasizer Nano ZS, Malvern Instruments). Nanoparticles prepared using bulk method are consistently larger than those prepared using microfluidics (FIG. 10).

Example 5

Size Distribution of Produced Particles

Size distributions for particles produced by microfluidics and by nanoprecipitation in bulk were measured using dynamic light scattering (Malvern Zetasizer Nano ZS, Malvern Instruments). Nanoparticles were prepared as described in Examples 3 and 4. Polymeric concentration was 50 mg/ml, and flow rate for microfluidic synthesis was 10 µl/min (water), 0.3 µl/min (PLGA-PEG), and/or 0.5 µl/min (20% PLGA). For PLGA-PEG nanoparticles, microfluidic method results in smaller particle size and narrower distribution. For 20% PLGA nanoparticles, bulk synthesis yields a long "tail" of larger nanoparticles that is absent in microfluidic synthesis.

Example 6

Creating a Particle Library

A library of particles is produced using a microfluidic device such as the one depicted in FIG. 4. The first inlet stream contains 50 mg/ml PLGA in acetonitrile. The second inlet stream contains 50 mg/ml PLGA-PEG in acetonitrile. The third inlet stream contains 50 mg/ml PLGA-PEG-A9 aptamer in acetonitrile. The fourth inlet stream contains 50 mg/ml PLGA-PEG-A10 aptamer in acetonitrile. The fifth inlet stream contains a solution of docetaxel (a chemotherapeutic agent) in acetonitrile. The present invention contemplates the use of more or less than 5 inlet streams to generate libraries of particles.

A library of particles is generated by doubling the flow rate of one stream so that it is 10 µl/min while keeping the flow rate of the other four streams constant at 5 µl/min. Aliquots of produced particles are collected every 15 seconds, and the contents of the produced particle populations are analyzed. Some properties of the produced particles are depicted in Table 1. The column labeled "Stream 1" depicts the properties of the resulting particles when the flow rate of stream 1 is doubled; the column labeled "Stream 2" depicts the properties of the resulting particles when the flow rate of stream 2 is doubled; and so forth.

|  | Stream 1 | Stream 2 | Stream 3 | Stream 4 | Stream 5 |
| --- | --- | --- | --- | --- | --- |
| mg particles produced per min | 5 mg/min | 10 mg/min | 5 mg/min | 5 mg/min | 8 mg/min |
| mean particle diameter | 25 nm | 50 nm | 50 nm | 50 nm | 30 nm |
| % (wt) PLGA | 40% | 19% | 19% | 19% | 23.5% |
| % (wt) PLGA-PEG | 19% | 40% | 19% | 19% | 23.5% |
| % (wt) PLGA-PEG-A9 | 19% | 19% | 40% | 19% | 23.5% |
| % (wt) PLGA-PEG-A10 | 19% | 19% | 19% | 40% | 23.5% |
| % (wt) docetaxel | 3% | 3% | 3% | 3% | 6% |

Table 1 shows that simply adjusting one parameter at a time (flow rate of one stream) in one manner (by doubling the rate) yields five different types of particles. The present invention contemplates simultaneously adjusting multiple parameters in a multitude of ways in order to generate up to thousands, millions, or more types of particles. In the present example, the flow rate of multiple streams may be adjusted simultaneously. Alternatively or additionally, the flow rate of the streams may be adjusted in multiple manners (e.g. by gradually varying the flow rate over time from 0.01 µl/min to 100 µl/min).

Any parameter can be varied in order to add diversity to the library of produced particles. Concentration of the polymer or therapeutic agent in one or more inlet streams may be varied. The identity of the polymer, solvent, targeting moiety, or therapeutic agent may be adjusted in one or more inlet streams. As more parameters are simultaneously varied in multiple ways, the diversity of the library of produced particles increases.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a nanoparticle" includes a plurality of such nanoparticle, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polymer, any solvent system, any produced particle, any therapeutic agent, any targeting moiety, any particle library, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A microfluidic system for producing organic particles comprising
   a device comprising a mixing apparatus and at least a center channel and an outer channel, and each channel has a cross-section independently selected from the group consisting of circular, oval, ovaloid, elliptical, and ellipsoid shapes, that converge into the mixing apparatus, wherein the width and height of each channel is between approximately 1 μm and approximately 1000 μm, and
   at least one polymer solution not containing particles, and a non-solvent fluid for each polymer not containing particles, wherein the polymer solution forms polymeric particles in the non-solvent fluid upon mixing,
   wherein the at least center and outer channels are positioned so that the polymer solution and non-solvent fluid flowing through each channel are directed at one another within the mixing apparatus, and
   wherein the position of the channels can be varied to alter the direction of the polymer solution or non-solvent fluid into the mixing apparatus,
   the device further comprising means for controlling the flow rates through the channels either using pumps or applying pressure to focus the polymer solution into a narrow stream having a width which is smaller than the channel width within the mixing apparatus, or
   wherein the mixing apparatus is selected from the group consisting of chaotic advection mixers, zigzag mixers, droplet mixers, shear superposition mixers, T-mixers, mixers based on Tesla structures, and active mixers,
   wherein the polymer solution forms polymeric particles in the mixing apparatus.

2. The microfluidic system of claim 1, wherein the system comprises a central channel and at least one outer channel, wherein the central channel is the mixing apparatus, wherein the at least one outer channel joins the central channel at an angle, whereby the polymer solution and non-solvent fluid move by laminar flow through the channel, and whereby particles are produced by nanoprecipitation using hydrodynamic flow focusing.

3. The microfluidic system of claim 1, wherein the polymer solution forms organic polymeric particles.

4. The microfluidic system of claim 1, wherein the mixing apparatus is selected from the group consisting of a chaotic advection mixer, a herringbone mixer, a zigzag mixer, a droplet mixer, a mixer based on Tesla structures, and an active mixer.

5. The microfluidic system of claim 1, further comprising an outlet channel from the mixing apparatus.

6. The microfluidic system of claim 1, wherein the width or height of each channel is between approximately 1 µm and approximately 100 µm.

7. The microfluidic system of claim 1, wherein the channels are arranged in one plane relative to one another.

8. The microfluidic system of claim 1, comprising means for applying pressure to each channel.

9. The microfluidic system of claim 1, comprising a plurality of inlet channels which converge into the central channel.

10. The microfluidic system of claim 9, comprising at least three inlet channels.

11. The microfluidic system of claim 9, comprising at least five inlet channels.

12. The microfluidic system of claim 1, wherein the channels are composed of a material suitable for the flow of a polymer solvent and a polymer non-solvent fluid.

13. The microfluidic system of claim 12, wherein the polymer is selected from the group consisting of polyethylenes, polycarbonates, polyanhydrides, polyhydroxyacids, polypropylfumarates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polyureas, polystyrenes, polyamines, derivatives thereof, combinations thereof, and copolymers thereof.

14. The microfluidic system of claim 12, wherein the polymer is selected from the group consisting of polyethylene glycol (PEG); poly(lactic acid-co-glycolic acid); copolymers of poly(lactic acid-co-glycolic acid) and PEG; poly(lactide-co-glycolide); copolymers of poly(lactide-co-glycolide) and PEG; polyglycolic acid; copolymers of polyglycolic acid and PEG; poly-L-lactic acid; copolymers of poly-L-lactic acid and PEG; poly-D-lactic acid; copolymers of poly-D-lactic acid and PEG; poly-D,L-lactic acid; copolymers of poly-D,L-lactic acid and PEG; poly-L-lactide; copolymers of poly-L-lactide and PEG; poly-D-lactide; copolymers of poly-D-lactide and PEG; poly-D,L-lactide; copolymers of poly-D,L-lactide and PEG; poly(ortho ester); copolymers of poly(ortho ester) and PEG; poly(caprolactone); copolymers of poly(caprolactone) and PEG; polylysine; copolymers of polylysine and PEG; poly(ethylene imine); copolymers of poly(ethylene imine) and PEG; polyhydroxyacids; polyanhydrides; poly(L-lactide-co-L-lysine); poly(serine ester); poly(4-hydroxy-L-proline ester); poly[α-(4-aminobutyl)-L-glycolic acid]; derivatives thereof, combinations thereof, and copolymers thereof.

15. The microfluidic system of claim 12, wherein the polymer solvent is selected from the group consisting of 1,4 dioxane, tetrahydrofuran (THF), acetone, acetonitrile, dimethyl sulfoxide (DMSO), dimethylformamide (DMF), acids, and alcohols.

16. The microfluidic system of claim 12, wherein the polymer non-solvent fluid is an aqueous solution or water.

17. The microfluidic system of claim 12, wherein the polymeric solution further comprises at least one therapeutic agent to be encapsulated in the particles.

18. The microfluidic system of claim 1, wherein the channels are composed of a material selected from the group consisting of a metal, a polymer, photocurable epoxy, polydimethylsiloxane, glass, silicon, combinations thereof.

19. The microfluidic system of claim 1, wherein the channels are formed by lithography, embossing, or molding of a polymeric surface.

20. The microfluidic system of claim 1, the device further comprising an apparatus for controlling the temperature.

21. A method of producing particles in a microfluidic system comprising at least a central and an outer channel, each channel having a cross-section independently selected from the group consisting of circular, oval, ovaloid, elliptical, and ellipsoid shapes, that converge into a mixing apparatus, wherein the width and height of each channel is between approximately 1 µm and approximately 1000 µm, and means for controlling the flow rates through the channels either using pumps or applying pressure to focus the polymer solution into a narrow stream having a width which is smaller than the channel width within the mixing apparatus, or wherein the mixing apparatus is selected from the group consisting of chaotic advection mixers, zigzag mixers, droplet mixers, shear superposition mixers, T-mixers, mixers based on Tesla structures, and active mixers; comprising the steps of:
  flowing a polymeric solution not containing particles through the central channel, wherein the solution comprises at least one polymer and a solvent;
  flowing a non-solvent fluid not containing particles for the polymer through at least one outer channel; and
  mixing the polymeric solution with the polymer non-solvent in the mixing apparatus to form polymer particles.

\* \* \* \* \*